(12) United States Patent
Shaunak et al.

(10) Patent No.: US 8,058,344 B2
(45) Date of Patent: Nov. 15, 2011

(54) GLYCODENDRIMERS HAVING BIOLOGICAL ACTIVITY

(75) Inventors: Sunil Shaunak, London (GB); Elisabetta Gianasi, Bologna (IT); Ruth Duncan, Cardiff (GB)

(73) Assignee: Imperial Innovations Ltd, London (GB)

( * ) Notice: Subject to any disclaimer, the term of this patent is extended or adjusted under 35 U.S.C. 154(b) by 1396 days.

(21) Appl. No.: 10/511,317

(22) PCT Filed: Mar. 18, 2003

(86) PCT No.: PCT/GB03/01133
§ 371 (c)(1),
(2), (4) Date: May 31, 2005

(87) PCT Pub. No.: WO03/089010
PCT Pub. Date: Oct. 30, 2003

(65) Prior Publication Data
US 2005/0214247 A1   Sep. 29, 2005

(30) Foreign Application Priority Data

Apr. 19, 2002   (GB) .................................. 0209022.3

(51) Int. Cl.
*A61K 31/785* (2006.01)
*C08G 63/48* (2006.01)
*C08G 63/91* (2006.01)
(52) U.S. Cl. .................................... 525/54.2; 424/78.27
(58) Field of Classification Search .......................... None
See application file for complete search history.

(56) References Cited

U.S. PATENT DOCUMENTS

| | | | |
|---|---|---|---|
| 5,338,532 A | 8/1994 | Tomalia et al. | |
| 5,527,524 A | 6/1996 | Tomalia et al. | |
| 5,560,929 A | 10/1996 | Hedstrand et al. | |
| 5,714,166 A | 2/1998 | Tomalia et al. | |
| 6,177,414 B1 | 1/2001 | Tomalia et al. | |
| 6,190,650 B1 | 2/2001 | Matthews et al. | |
| 6,312,679 B1 | 11/2001 | Tomalia et al. | |
| 2003/0114418 A1* | 6/2003 | Pulaski et al. ................... 514/62 |
| 2010/0173871 A1 | 7/2010 | Poupot et al. | |

FOREIGN PATENT DOCUMENTS

| | | |
|---|---|---|
| WO | WO 88/01178 | 2/1988 |
| WO | WO 91/11172 | 8/1991 |
| WO | WO 94/02518 | 2/1994 |
| WO | WO 95/24221 | 9/1995 |
| WO | WO 95/34595 | 12/1995 |
| WO | WO 98/55148 | 12/1998 |
| WO | WO98/56353 | 12/1998 |
| WO | WO 02/00196 | 1/2002 |
| WO | WO 03/089010 | 10/2003 |
| WO | WO2007/045009 | 4/2007 |
| WO | WO2007/045010 | 4/2007 |
| WO | WO2007/048190 | 5/2007 |
| WO | WO2007/082331 | 7/2007 |
| WO | WO2008/017122 | 2/2008 |
| WO | WO 2008/017125 | 2/2008 |
| WO | WO2009/004639 | 1/2009 |
| WO | WO 2009/103123 | 8/2009 |

OTHER PUBLICATIONS

Cloninger, Curr Opin Chem Biochem, 6:742-748. 2002.*
Rockendorf et al. (Topics in Current Chemistry, 217: 2001.*
Lam et al., J. Polym, Res., vol. 6 (4): 203-210, 1999.*
Zanini and Roy, "Novel Dendritic α-Sialosides: Synthesis of Glycodenrimers Based on a 3,3'-Iminobis(propylamine) Core", Journal of Organic Chemistry, vol. 61, pp. 7348-7354; 1996.
Brewer, "Lectin Cros-Linking Interactions with Multivalent Carbohydrates", In "The Molecular Immunology of Complex Carbohydrates—2", editor Wu, Kluwer Academic/Plenum Publishers, 2001.
Tomalia et al., Angewandte Chemie-International Edition in English, 1990, vol. 29, pp. 138-175.
Newkome et al., Journal of Organic Chemistry, 1992, vol. 57, pp. 358-362.
Jansen et al., Science, 1994, vol. 266, pp. 1226-1229.
Page and Roy, Bioconjugate Chemistry, 1997, vol. 8, pp. 714-723.
Ashton et al., Chemistry A European Journal, 1997, vol. 3, pp. 974-984.
Malik et al., Journal of Controlled Release, 2000, vol. 65, pp. 133-148.
Tsutsumiuchi et al. Polymer Journal, 1999, vol. 31, pp. 935-941 (Abstract only).
Shaunak et al. Nature Biotechnology, 2004, vol. 22, pp. 977-984, Supl. pp. 1-10.
Aghezedeh-Habashi et al, J Pharm Pharmaceut Sci 5(2):181-184, 2002 Single Dose Pharmacokinetics and Bioavailability of Glucosamine in the Rat.
Atala A et al., MRS Bulletin Aug. 2010; 35: 597-606, Wound healing versus regeneration: Role of the tissue environment in regenerative medicine.
Ashton PR et al, Chem. Eur. J. 1997; 3(6): 974-984, Synthesis of glycodendrimers by modification of poly(propylene imine) dendrimers.
Balan et al, Bioconjugate Chem. 2007, 18 61-76, Site-Specific PEGylation of Protein Disulfide Bonds Using a Three-Carbon Bridge.
Bauer J et al, Cellular Physiology 1992 153: 437-449, In vitro model of angiogenesis using human endothelium derived from permanent cell line.

(Continued)

*Primary Examiner* — James D Anderson
*Assistant Examiner* — Bong-Sook Baek
(74) *Attorney, Agent, or Firm* — Nixon & Vanderhye P.C.

(57) ABSTRACT

The present invention relates to new anionic glycodendrimers having new biological activity, processes for preparing them and their use in medicine including veterinary medicine.

3 Claims, 55 Drawing Sheets

OTHER PUBLICATIONS

Figure 1A:
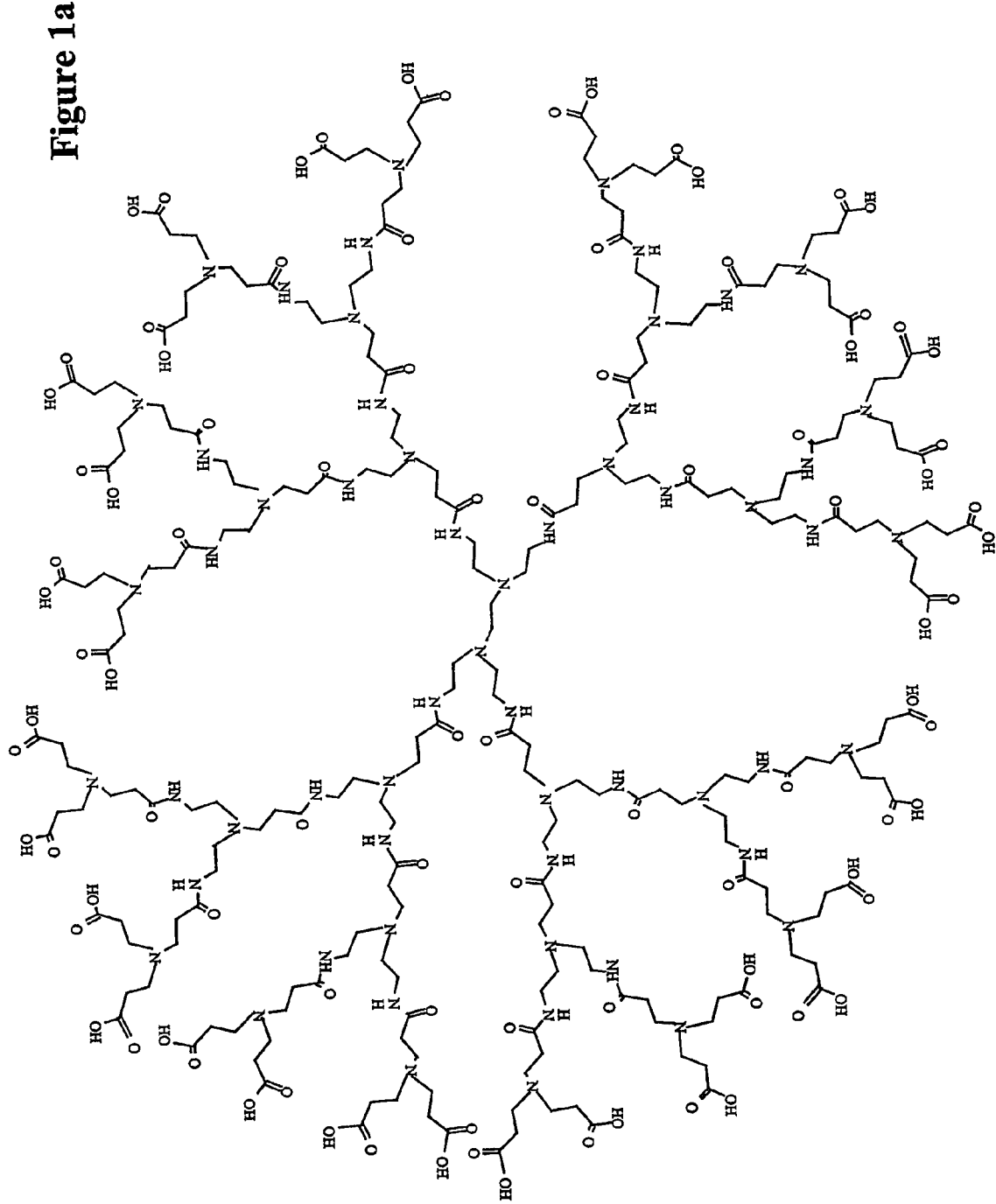

Brewer et al, The Molecular Immunology of Complex Carbohydrates—2 Editor Wu, Kluwer Academic/Plenum Publishers, 2001, Lectin Cross-Linking Interactions with Multivalent Carbohydrates.

Boyd BJ et al, Mol Pharm 2006;3 No. 5, 614-627, Cationic Poly-L-lysine Dendrim.

Brandtzaeg et al, J. Exp. Med. vol. 184 Jul. 1996 51-60, Net Inflammatory Capacity of Human Septic Shock Plasma Evaluated by a Monocyte-based Target Cell Assay: Identification of Interleukin-10 as a Major Functional Deactivator o f Human Monocytes.

Bryant et al, Nature Reviews Microbiology vol. 8 Jan. 2010, The molecular basis of the host response to lipopolysaccharide.

Chang et al, Survey of Ophthalmology vol. 45 No. 1 Jul.-Aug. 2000, The Role of the Immune System in Conjunctival Wound Healing After Glaucoma Surgery.

Chen et al, J. Am. Chem. Soc 2004, 126, 10044-10048, Cytotoxicity, Hemolysis and Acute in Vivo Toxicity of Dendrimers Based on Melamine, Candidate Vehicles for Drug Delivery.

Chouai A et al, J. Organic Chemistry 2008; 73(6): 2357-2366, Kilogram-Scale Sythesis of a Second-Gneration Dendrimer Based 1,3,5-Triazine Using Green and Industrially Compatible Methods with a Single Chromatographic Step.

Choy et al, N Engl J Med, vol. 344, No. 12 Mar. 22, 2001, Cytokine Pathways and Joint Inflammation in Rheumatoid Arthritis.

Cloninger, Current Opinion in Chemical Biology 2002, 6:742-748, Biological applications of dendrimers.

Cordeiro et al, Investigative Opthamology and Visual Science 1999 40 2225-34, Human Anti-Transforming Growth Factor-b2 Antibody: A New Glaucoma Anti-Scarring Agent.

Duncan, Nature Reviews Drug Discovery vol. 2 May 2003 347-60, The Dawning Era of Polymer Therapeutics.

Flo et al, The Journal of Biological Chemistry vol. 277, No. 38, pp. 35489-35495, 2002, Involvement of Toll-like Receptor (TLR) 2 and TLR4 in Cell Activation by Mannuronic Acid Polymers.

Fukasawa et al, Journal of Surgical Research 1989, 46(2), 166-71, Modulation of proline and glucosamine incorporation into tissue repair cells by peritoneal macrophages.

Garcia-Ramallo et al, The Journal of Immunology 2002;169;6467-6473, Resident Cell Chemokine Expression Serves as the Major Mechanism for Leukocyte Recruitment During Local Inflammation.

Gaspar et al, Advance Drug Delivery Reviews 61 (2009) 1220-1231, Polymeric carriers: Preclinical safety and the regulatory implications for design and development of polymer therapeutics.

Girard & Springer, Immunology Today 1995 16(9) 449-57, High endothelial venules (HEVs): specialized endothelium for lymphocyte migration.

Gordon, Cell, vol. 111, 927-930, Dec. 27, 2002, Pattern Recognition Receptors: Doubling Up for the Innate Immune Response.

Hollink E et al, Org Lett 2006;8:2293-2295, A Divergent Route to Diversity in Macromolecule.

Hourani et al, Macromol. Rapid Commun. 2010; 31: 947-974, Advances in the elegance of chemistry in designing dendrimers.

Hoshino et al, *J. Immunol.* 1999;162;3749-3752, Cutting Edge: Toll-Like Receptor 4 (TLR4)-Deficient Mice Are Hyporesponsive to Lipopolysaccharide: Evidence for TLR4 as the *Lps* Gene Product.

Jansen JFGA, Science Nov. 18, 1994:vol. 266. No. 5188, pp. 1226-1229, Encapsulation of guest molecules into a dendritic Box.

Jayamurugan G et al, Tetrahedron 62 (2006) 9582-9588, Sythesis of large generation poly(propyl ehter imine) (PETIM) dendrimers.

Jerala R, International Jounral of Medical Microbiology 297 (2007) 353-363, Structural Biology of the LPS recognition.

Jevprasesphant et al, *Pharmaceutical Research*, vol. 20, No. 10, Oct. 2003, Engineering of Dendrimer Surfaces to Enhance Transepithelial Transport and Reduce Cytotoxicity.

Jiang Z et al, Nat Immunol 2005;6:565-569, CD12 is required for MyD88-independent LPS signalling.

Johnson et al, *J. Immunol.* 2004;172;20-24, Cutting Edge: An Endogenous Pathway to Systemic Inflammatory Response Syndrome (SIRS)-Like Reactions through Toll-Like Receptor 4.

Kagan et al, Nature Immunology vol. 9 No. 4 Apr. 2008, TRAM couples endocytosis of Toll-like receptor 4 to the induction of interferon-beta.

Karlsson et al, Infection and Immunity May 2004 p. 2671-2678, Paterrn of Cytokine Responses to Gram-Positive and Gram-Negative Commensal Bacteria Is Profoundly Changed when Monocytes Differentiate into Dendritic Cells.

Khaw et al, Ophthalmology. Mar. 1993;100(3):367-72, Effects of intraoperative 5-fluorouracil or mitomycin C on glaucoma filtration surgery in the rabbit.

Kopf et al, Nature Reviews Drug Discovery vol. 9 Sep. 2010 703, Averting inflammation by targeting the cytokine environment.

Koyanagi et al, Biochemical Pharmacology 65 2003 173-9, Oversulfation of fucoidan enhances its anti-angiogenic and antitumor activities.

Krishna T et al, J. Org Chem 2003, 68, 9694-9704, Synthesis of Poly(propyl ether imine) Dendrimers and Evaluation of Their Cytotoxic Properties.

Krishna T et al, Tetrahedron 2005; 61: 4281-4288, Synthesis and biological evaluation of 3-amino-propanol-1-ol based poly(ether imine) dendrimers.

Kubota et al, The Journal of Cell Biology, vol. 107, Oct. 1988 1589-1598, Role of Laminin and Basement Membrane in the Morphological Differentiation of Human Endothelial Cells into Capillary-like Structures.

Lam et al, J. Polym, Res., vol. 6 (4): 203-210, 1999, Preparation and characterization of covalently bonded biopolymer-polypyrrole hybrid materials.

Liaw & Schwartz, American Journal of Pathology 1993, 143: 937-948, Microtubule disruption stimulates DNA synthesis on bovine endothelial cells and potentiates cellular responses to basic fibroblast growth factor.

Lalwani S et al, Macromolecules 2009; 42: 3152-3161, Electrophoretic Behaviour of Anionic Triazine in PAMAM Dendrimers.

Lalwani S et al, Macromolecules 2009; 42: 6723-6732, Mimicking PAMAM Dendrimers with Amphoteric, Hybrid Triazine Dendrimers.

Lehto & Jarvinen, *Eur Surg Res* 1985;17:179-185, Collagen and Glycosaminoglycan Synthesis of Injured Gastrocnemius Muscle in Rat.

Le Naour et al, *The Journal of Biological Chemistry* vol. 276, No. 21, pp. 17920-17931, 2001, Profiling Changes in Gene Expression during Differentiation and Maturation of Monocyte-derived Dendritic Cells Using Both Oligonucleotide Microarrays and Proteomics.

Li et al, *J. Immunol.* 2003;170;3369-3376, IL-8 Directly Enhanced Endothelial Cell Survival, Proliferation, and Matrix Metalloproteinases Production and Regulated Angiogenesis.

Lim J et al, Org Lett 2010;12:1148, Synthesis of Odd Generation Triazine Dendrimers Using a Divergent Macromonomer Approach.

Lundin et al, The Journal of Biological Chemistry vol. 275, No. 32, pp. 24653-24660, 2000 Selectively Desulfated Heparin Inhibits Fibroblast Growth Factor-induced Mitogenicity and Angiogenesis.

Malik N et al, J Cont Release 2000;65:133-148, Dendrimers: Relationship between structure and biocompatibility in vitro, and preliminary studies on the biodistribution of 125I-labelled polyamidoamine dendrimers in vivo.

Mamman et al, Angew. Chem. Int. Ed. 1998, 37, 2754-2794, Polyvalent Interactions in Biological Systems: Implications for Design and Use of Multivalent Ligands and Inhibitors.

Mead et al, Investigative Ophthalmology & Visual Science, Aug. 2003, vol. 44, No. 8 3394-401, Evaluation of Anti-TGF-$\beta$2 Antibody as a New Postoperative Anti-scarring Agent in Glaucoma Surgery.

Meng J et al, J Biol Chem 2010;285:8695-8702, MD-2 mediated Ionic Interactions between Lipid A and TLR4 Are Essential for Receptor Activation.

Menjoge AR et al, Drug Discovery Today 2010;15:171-185, Dendrimer-based drug and imaging conjugates: design considerations for nanomedical applications.

Neerman MR et al, Int J Pharm 2004;281:129-132, In vitro and in viv evalutation of a melamine dendrimer as a vehicle for drug delivery.

Newkome et al, Journal of Organic Chemistry 1992 57, 358-362, Chemistry of micelle series 22 cascade polymer synthesis and characterisation of 4-directional spherical dendritic macromolecules based on admanate.

Norrby-Teglund A, European Journal of Immunology, 2000; 30: 3247-3255, Host variation in cytokine responses to superantigens determine the severity of invasive group A streptococcal infection.
Page et al, Bioconjugate Chemistry, American Chemical Society, vol. 8, No. 5, Sep. 1, 1997 714-723, Synthesis and Biological Properties of Mannosylated Starburst Poly(Amidoamine) Dendrimers.
Park BS et al, Nature 2009; 458: 1191-1195, The structural basis of lipopolysaccharide recognition by the TLR4-MD-2 complex.
Paterson et al, *J. Immunol.* 2003;171;1473-1483, Injury Primes the Innate Immune System for Enhanced Toll-Like Receptor Reactivit.
Pathan N et al, Lancet 2004;363:203, Role of interleukin 6 in myocardial dysfunction of meningococcal septic shock.
Perdomo et al, J. Exp Med. vol. 180 Oct. 1994 1307-1319, Acute Inflammation Causes Epithelial Invasion and Mucosal Destruction in Experimental Shigellosis.
Prasad et al, MRS Bulletin vol. 35 Aug. 2010 571-577, Engineering Materials for Regenerative Medicine.
Pye et al, The Journal of Biological Chemistry vol. 273, No. 36, pp. 22936-22942, 1998, Heparan Sulfate Oligosaccharides Require 6-*O*-Sulfation for Promotion of Basic Fibroblast Growth Factor Mitogenic Activity.
Raqib R et al, J Infect Dis 1995; 171: 376, Cytokine secretion in acute shigellosis is correlated to disease activity and directed more to stool than to plasma.
Roberts et al, Journal of Biomedical Materials Research, vol. 30, 53-65 (1996), Preliminary biological evaluation of polyamidoamine (PAMAM) StarburstTM dendrimers.
Rockendorf, Topics in Current Chemistry 217 2001, Glycodendrimers.
Roy, Topics in Current Chemistry, 1997, vol. 187/1997, 241-274, Recent developments in the rational design of multivalent glycoconjugates.
Sansonetti PJ et al, J Clin Invest 1995;96:884-892, Role of Interleukin-1 in the Pathogenesis of Experimental Shigellosis.
Schlessinger et al, Molecular Cell, vol. 6, 743-750, Sep. 2000, Crystal Structure of a Ternary FGF-FGFR-Heparin Complex Reveals a Dual Role for Heparin in FGFR Binding and Dimerization.
Schmidt et al, J Pharm Pharmacol. Nov. 1989;41(11):781-4, Biocompatibility of wound management products: the effect of various monosaccharides on L929 and 2002 fibroblast cells in culture.
Setnikar & Rovati, Arzneimittelforschung. Sep. 2001;51(9):699-725, Absorption, distribution, metabolism and excretion of glucosamine sulfate. A review.
Setnikar et al, Pharmatherapeutica. 1984;3(8):538-50, Absorption, distribution and excretion of radioactivity after a single intravenous or oral administration of [14C] glucosamine to the rat.
Sgouras & Duncan, Journal of Materials Science: Materials in Medicine I (1990) 61-68, Methods for the evaluation of biocompatibility of soluble synthetic polymers which have potential for biomedical use: 1—Use of the tetrazolium-based colorimetric assay (MTT) as a preliminary screen for evaluation of in vitro cytotoxicity.
Shaunak S et al, Nature Biotechnology 2004; 22: 977-985, Polyvalent dendrimer glucosamine conjugates prevent scar tissue formation.
Shaunak et al, Nat. Chem Bio. vol. 2 No. 6 Jun. 2006 312-313, Site Specific PEGylation of native disulfide bonds in therapeutic proteins.
Shipley et al, Comparative Medicine vol. 60 No. 1 Feb. 2010, A Challenge Model for Shigella dysenteriae 1 in Cynomolgu Monkeys.
Siriwardena et al, Ophthalmology vol. 109, No. 3, Mar. 2002 427-3, Human Antitransforming Growth Factor β2 Monoclonal Antibody—A New Modulator of Wound Healing in Trabeculectomy: *A Randomized Placebo Controlled Clinical Study*.
Simanek E et al, Proc. R. Soc. A. 2010; 466 (2117); 1445-1468, The 8 year thicket of triazine dendrimers: strategies, targets and applications.
Simanek E, Molecular Pharmaceutics 2010; vol. 7, No. 4, 921, Polymers for Biomedical Applications.
Slivka PF et al, 1ChemBioChem 2009;10:645-649, A Peptide Antagonist of the TLR4-MD2 Interaction.

Smiley et al, *The Journal of Immunology*, 2001, 167: 2887-2894, Fibrinogen Stimulates Macrophage Chemokine Secretion Through Toll-Like Receptor 4.
Spinks et al, *J Neurophysiol 90:1324-1332*, 2003, Problem of Dural Scarring in Recording From Awake, Behaving Monkeys: A Solution Using 5-Fluorouracil.
Svenson S et al, Adv Drug Delivery Rev 2005;57:2106, Dendrimers in biomedical applications-reflections on the field.
Sweeney et al, Blood, Jan. 1, 2002 vol. 99, No. 1 44-51, Sulfated polysaccharides increase plasma levels of SDF-1 in monkeys and mice: involvement in mobilization of stem/progenitor cells.
Takaoka A et al, Nature 2005;434:243-249, Integral role of IRF-5 in the gene induction programme activated by Toll-like receptors.
Takeuchi et al, Immunity, vol. 11, 443-451, Oct. 1999, Differential Roles of TLR2 and TLR4 in Recognition of Gram-Negative and Gram-Positive Bacterial Cell Wall Components.
Termeer et al, J. Exp. Med. vol. 195, No. 1, Jan. 7, 2002 99-111, Oligosaccharides of Hyaluronan Activate Dendritic Cells via Toll-like Receptor 4.
Thornton et al, Antimicrobial Agents and Chemotherapy, Oct. 1999, p. 2528-2533, Anti-Kaposi's Sarcoma and Antiangiogenic Activities of Sulfated Dextrins.
Tomalia DA et al, (1990)Angewandte Chemie-International Edition, 29, 138-175, Starburst dendrimers: molecular level control of size, shape, surface chemistry, topology and flexibility from atoms to macroscopic matter.
Tsutsumiuchi et al, Polymer Journal, 1999, vol. 31 pp. 935-941 (abstract only), Globular carbohydrate macromolecule "sugar balls" IV. Synthesis of dendritic nanocapsules with molecular recognition sites on periphery.
Tumpey T M, J Virol 1998, 72, 3705-3710, Absence of Macrophafe Inflammatory Protein-1alpha Precvents the Development of Blinding Herpes Stromal Keratitis.
Turnbull WB et al, Reviews in Molecular Biotechnology. 2002; 90: 231-255, Design and synthesis of glycodendrimers.
Van Duijvenbode et al, Macromolecules, vol. 33, 2000, pp. 46-52, Synthesis and protonation behavior of carboxylated-functionalized poly(propyleneimine) dendrimers.
Viriyakosol S et al, J. Biological Chemistry 2001; 276(41): 38,044-38,051, MD2 binds to bacterial lipopolysaccharide.
Vogte F et al, Dendrimer chemistry—concepts, synthesis, properties and applications. 2009 Publisher Wiley. Chapter 8: Special properties and potential applications. pp. 289-324 and also Figure 2, Chapter 1, pp. 1-22.
Von der Lieth-W et al, Reviews in Molecular Biotechnology 2002; 90: 311-337, Molecular dynamics simulations of glycoclusters and glycodendrimers.
Wang Z M, J Biol Chem 2000, 275, 20260-20267, Chemokines Are the Main Proinflammatory Mediators in Human Monocytes Activated by *Staphylococcus aureus*, Peptidoglycan and Endotoxin.
Wells A P, Opthalmology 2003, 110, 2192-2197, Cystic Bleb Formation and Related Complications in Limbus versis Fornix Based Conjunctival Flaps in Pediatric and Young Adult Trabeculectomy with Mitomycin C.
West NP et al, Science 2005;307:1313, Optimization of Viulence Functions Through Glucosylation of Shigella LPS.
Zhang P et al, J Immunol 2006;177:4002-4011, Role of N-Acetylglucosamine within Core Lipopolysaccharide of Several Species of Gram-Negative Bacteria in Targeting the DC-SIGN (CD209).
Zloh et al, Nature Protocols 2007 vol. 2 No. 5 p. 1070-1083, Identification and insertion of 3-carbon bridges in protein disulfide bonds: a computational approach.
Zuany-Amorim C et al, Nature Reviews Drug Discovery 2002; 1: 797-807, Toll-like receptors as potential therapeutic targets for multiple diseases.

* cited by examiner

PD-10 column of dendrimers gen 2.5-glucosamine after synthesis [D gen 2.5-G (0 d)] and after 30 days of storage [D gen 2.5-G (30 d)]

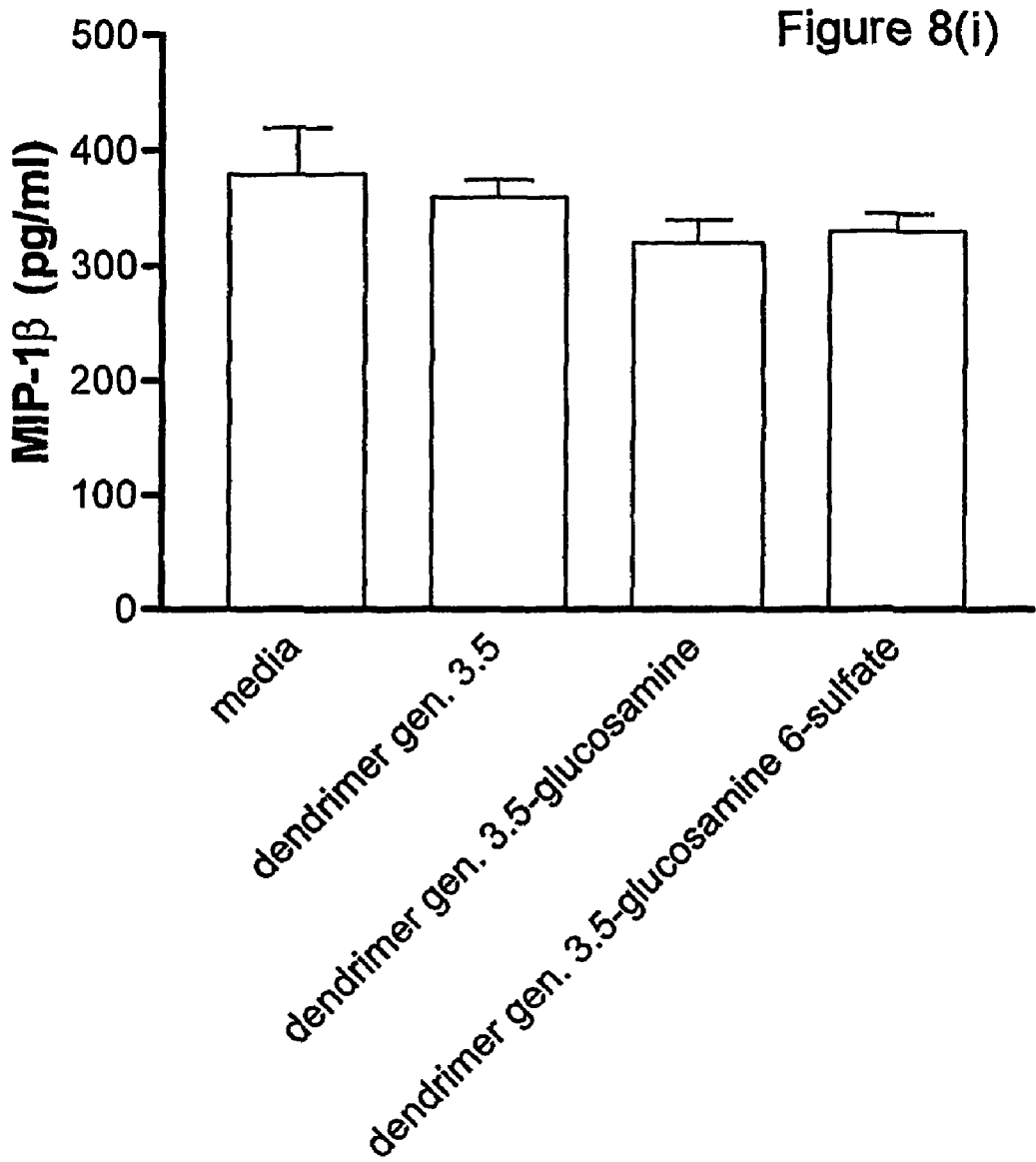
- n = 3. Results shown as mean ± sem. p = ns.
- single donor PBMN cells.
- all compounds used at 50 µg/ml.
- culture supernatants harvested for MIP-1β at 36 h.

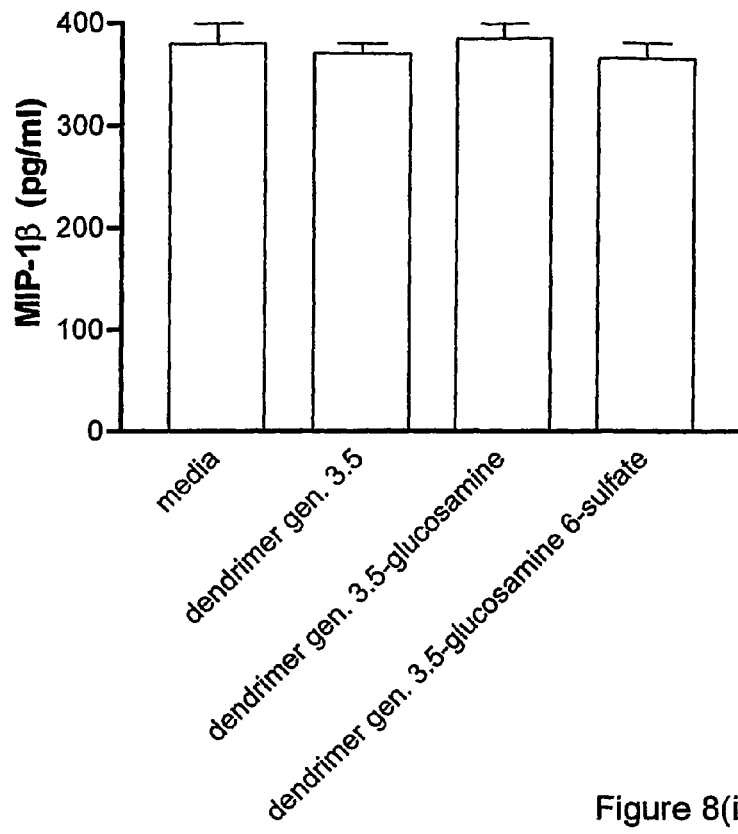
p = ns
Figure 8(ii)
Figure 8(iii)
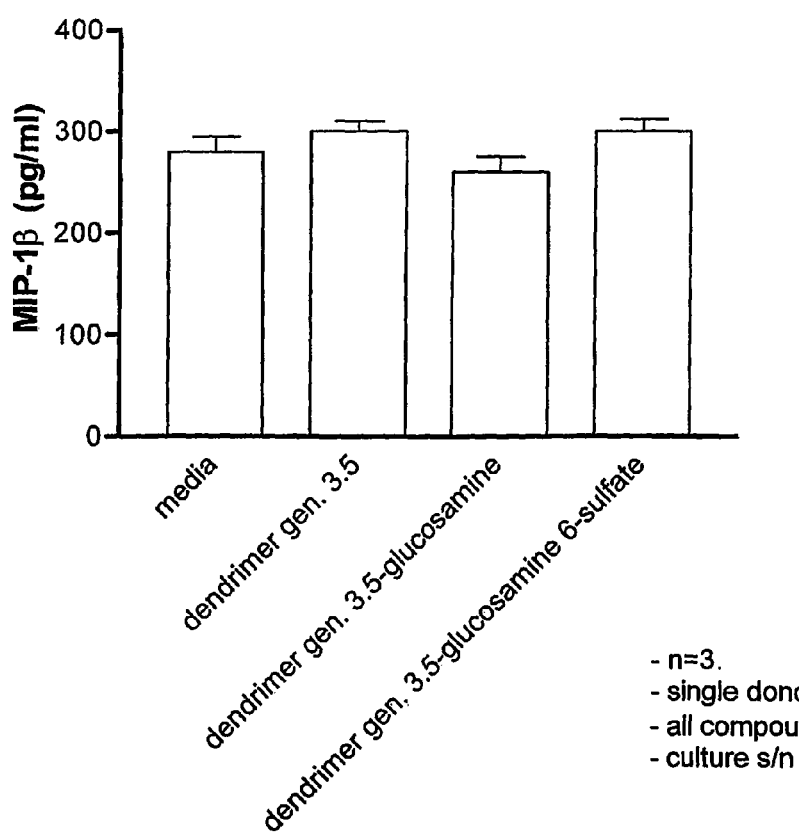
p = ns
- n=3.
- single donor MDMs.
- all compounds used at 50 μg/ml.
- culture s/n harvested at 36 h.

p = ns

- n = 3.
- single donor MDMs.
- all compounds used at 50 µg/ml.
- culture supernatants harvested for MIP-1β after 36 h.

p = ns

- n = 3.
- single donor peritoneal macrophages.
- all compounds used at 25 μg/ml.
- culture supernatants harvested at 36 h.

Figure 10I:
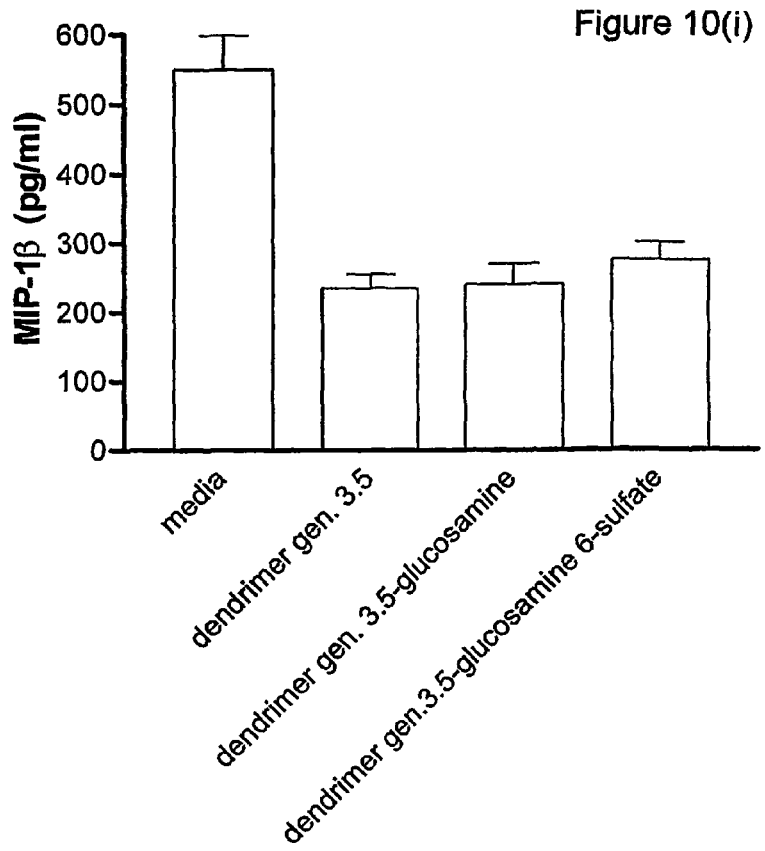
Figure 10:
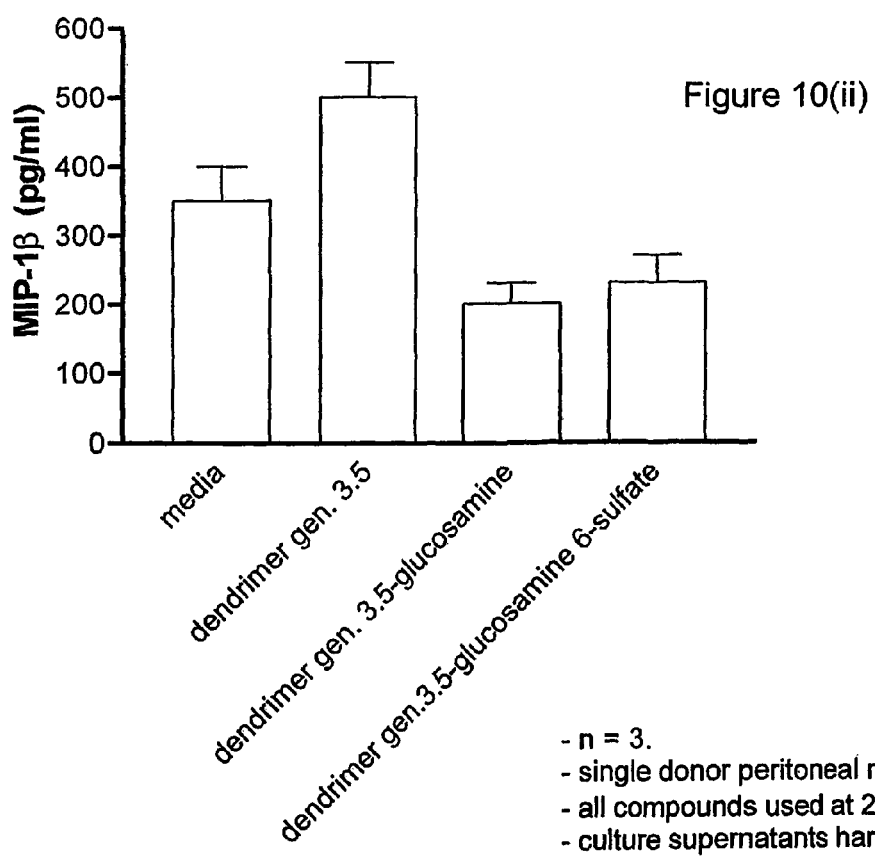

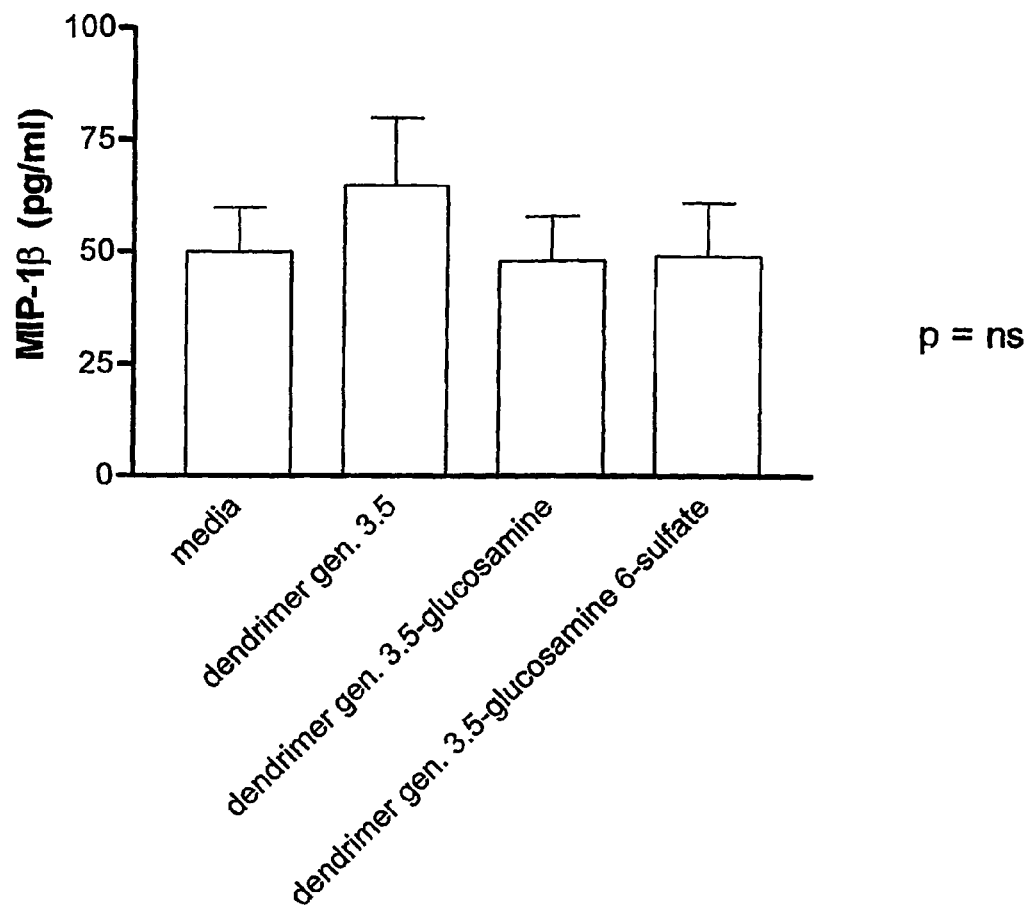
Figure 10(iii)
p = ns
- n = 3.
- single donor peritoneal macrophages.
- all compounds used at 25 μg/ml.
- culture supernatants harvested for MIP-1β at 72 h.

p = ns

- n = 3.
- single donor peritoneal macrophages.
- all compounds used at 50 μg/ml.
- culture supernatants harvested at 36 h.

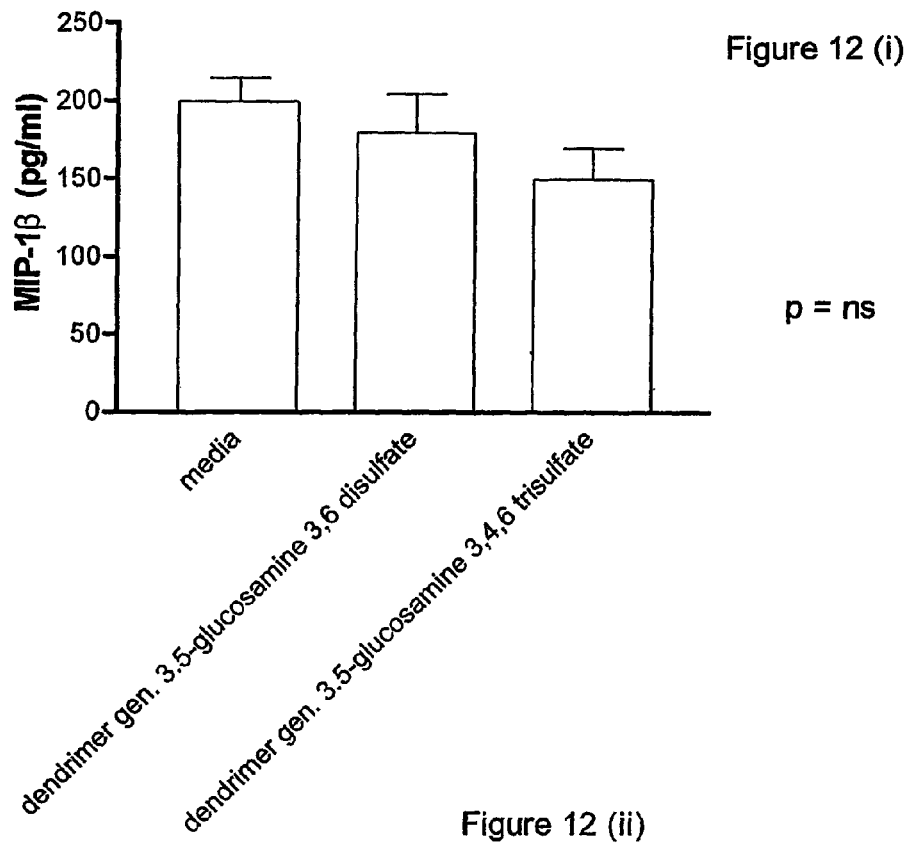
Figure 12 (i)
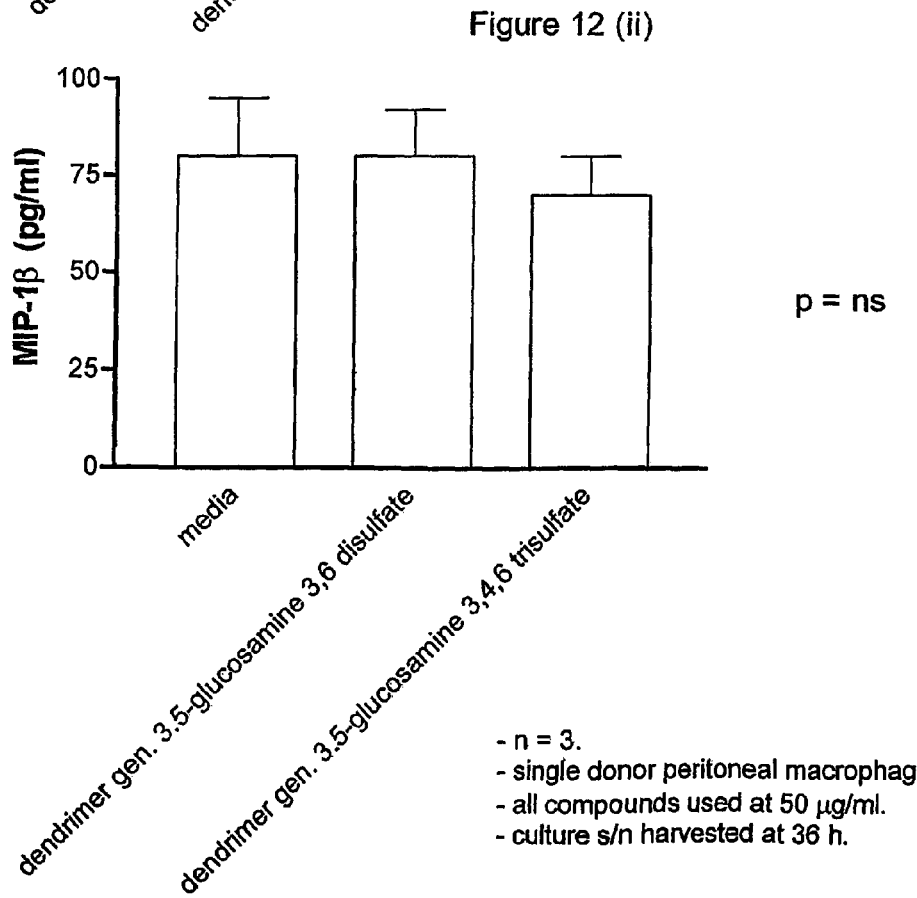
Figure 12 (ii)
- n = 3.
- single donor peritoneal macrophages.
- all compounds used at 50 μg/ml.
- culture s/n harvested at 36 h.

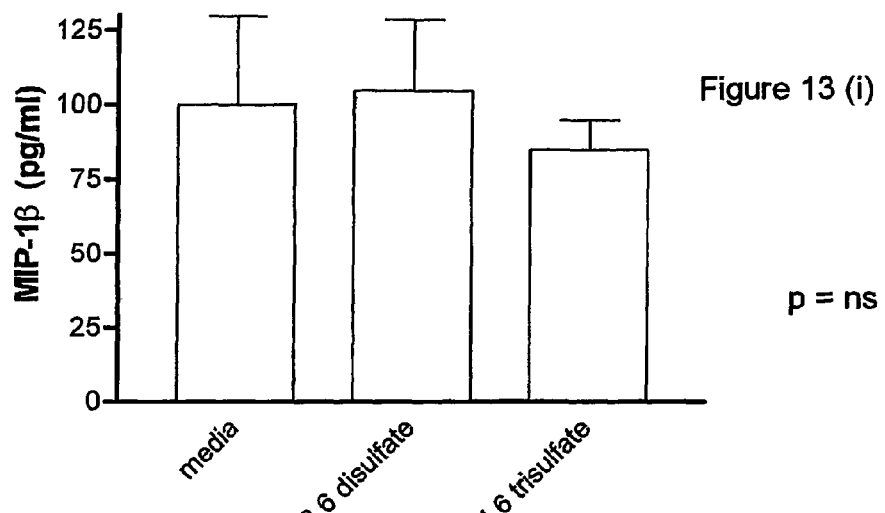
Figure 13 (i)
p = ns
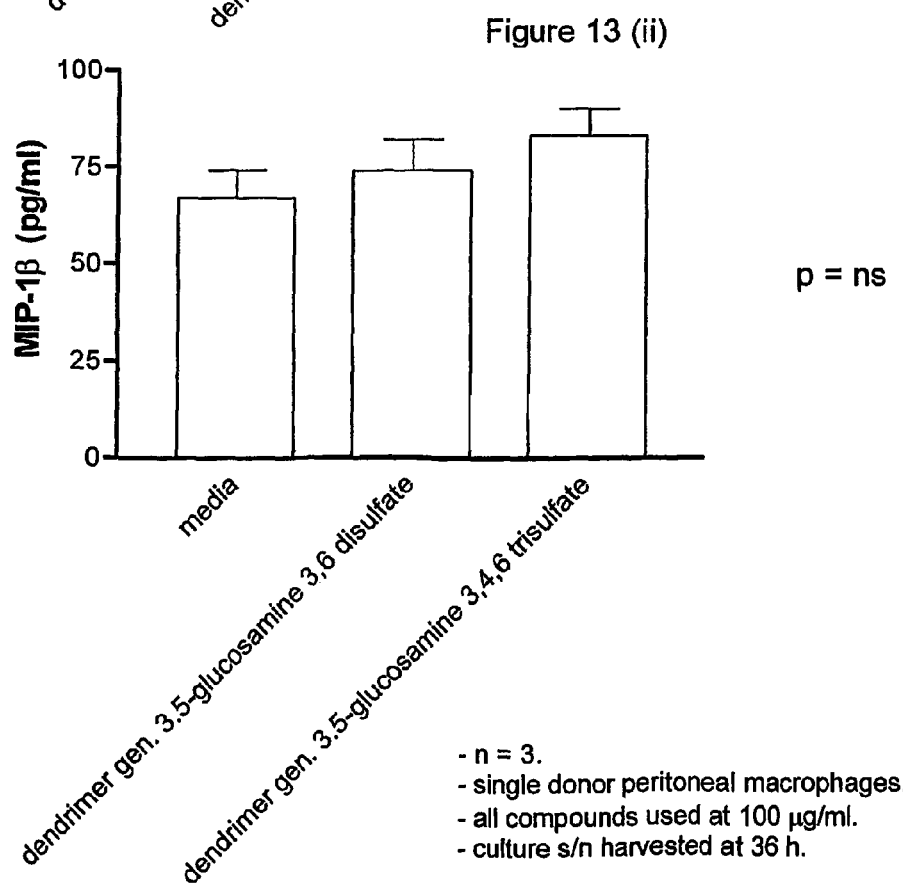
Figure 13 (ii)
p = ns
- n = 3.
- single donor peritoneal macrophages.
- all compounds used at 100 µg/ml.
- culture s/n harvested at 36 h.

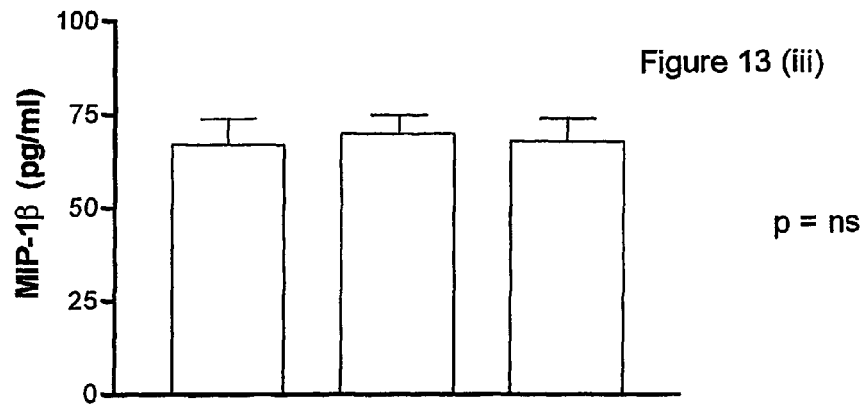
Figure 13 (iii)
p = ns
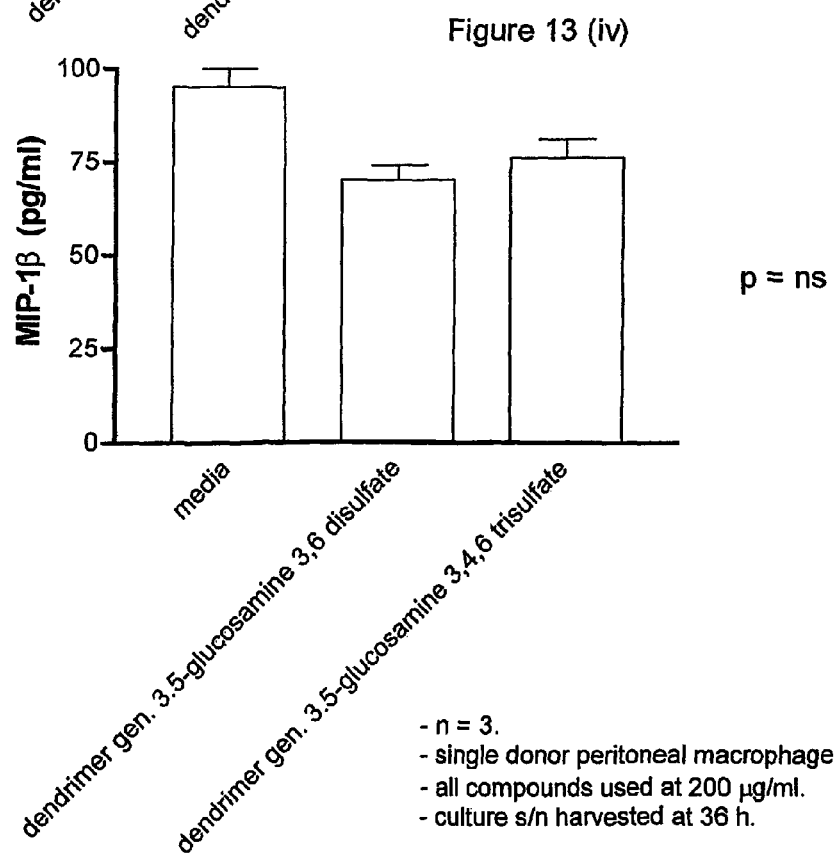
Figure 13 (iv)
p = ns
- n = 3.
- single donor peritoneal macrophages.
- all compounds used at 200 μg/ml.
- culture s/n harvested at 36 h.

- n = 3.
- single donor MDMs.
- MTT assay.

- n = 3.
- HUVECs.
- MTT assay.

Time course of the release of MIP-1β into cell free culture supernatants after the addition of LPS at a final concentration of 5 ng/ml & 10 ng/ml.

Figure 16I:
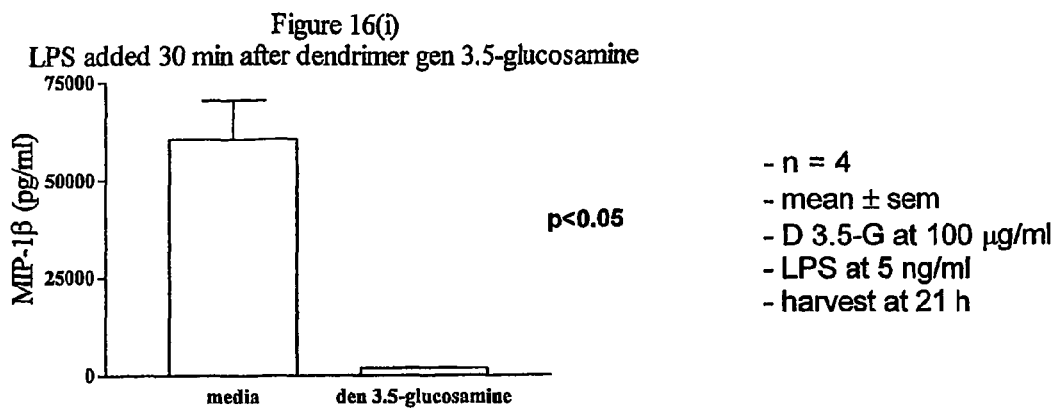
Figure 16:
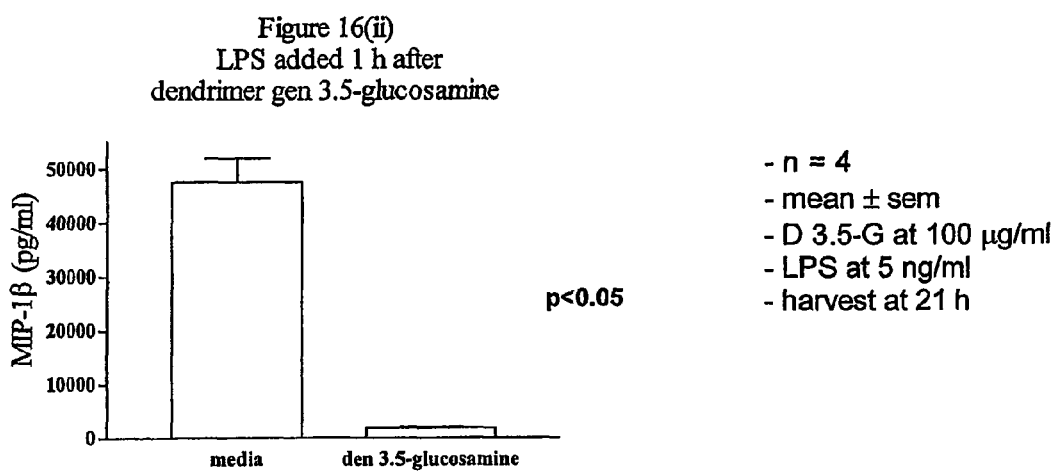
Figure 16:
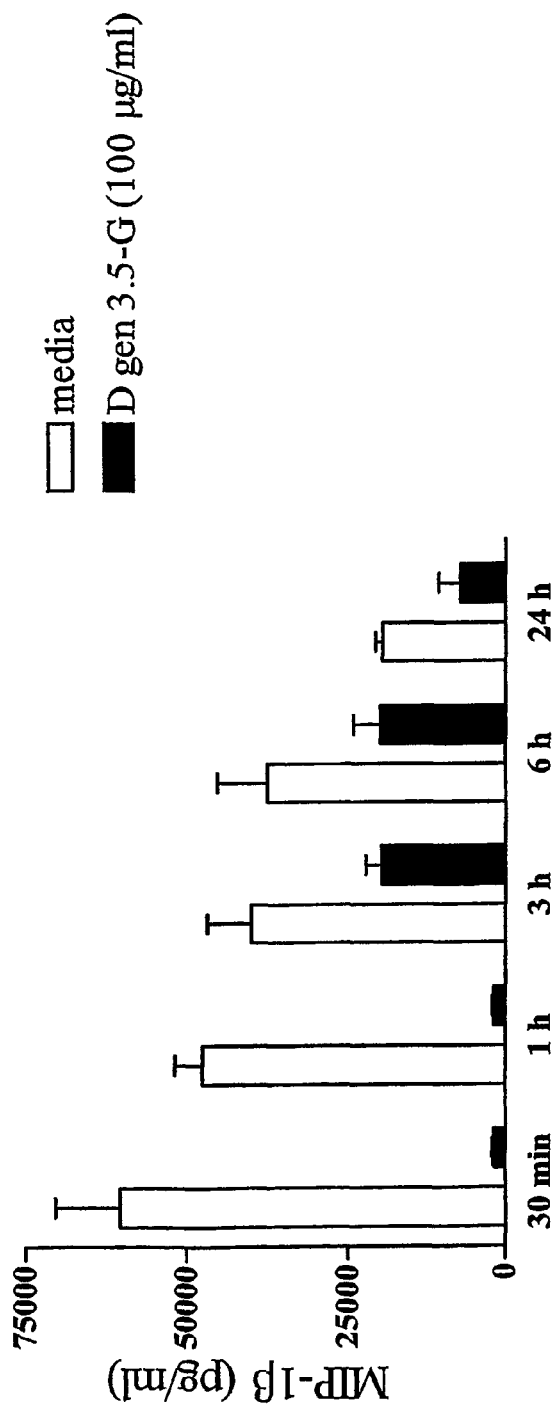

LPS added 30 min after dendrimer gen 3.5-glucosamine
- n = 4
- mean ± sem
- D 3.5-G at 100 µg/ml
- LPS at 5 ng/ml
- harvest at 21 h
LPS added 1 h after dendrimer gen 3.5-glucosamine
- n = 4
- mean ± sem
- D 3.5-G at 100 µg/ml
- LPS at 5 ng/ml
- harvest at 21 h
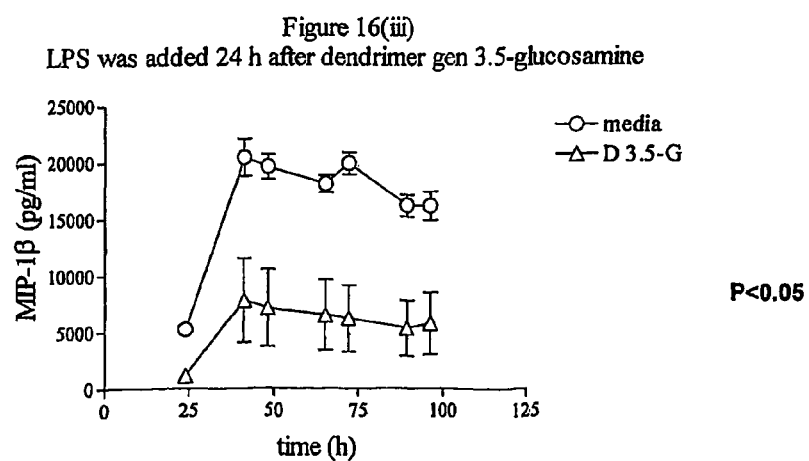
Figure 16(iii)
LPS was added 24 h after dendrimer gen 3.5-glucosamine
P<0.05

- Release of MIP-1β from single donor PBMN cells. n = 4.
- LPS (5 ng/ml) was added at various time points ranging from 30 min to 24 h after dendrimer gen. 3.5-glucosamine (100 µg/ml).
- Culture supernatants harvested 21 h after the addition of LPS for MIP-1 β.

(D gen 3.5-G: dendrimer gen 3.5-glucosamine)

Time course of the release of TNF-α into cell free culture supernatants following the addition of LPS at a final concentration of 5 ng/ml and at 10 ng/ml.

LPS (5 ng/ml) was added 30 min after dendrimer gen 3.5-glucosamine (100 μg/ml) and culture supernatants harvested at 21 h.
($P<0.05$ for all 6 figures)

LPS (5 ng/ml) was added 30 min after dendrimer gen 3.5-glucosamine (200 µg/ml) and culture supernatants harvested at 25 h.
($P<0.05$ for all groups)

LPS (5 ng/ml) added 1 hour after dendrimer gen 3.5-glucosamine (200 µg/ml) and culture supernatants harvested at 25 h. ($p<0.05$ for all groups)

Figure 21I:
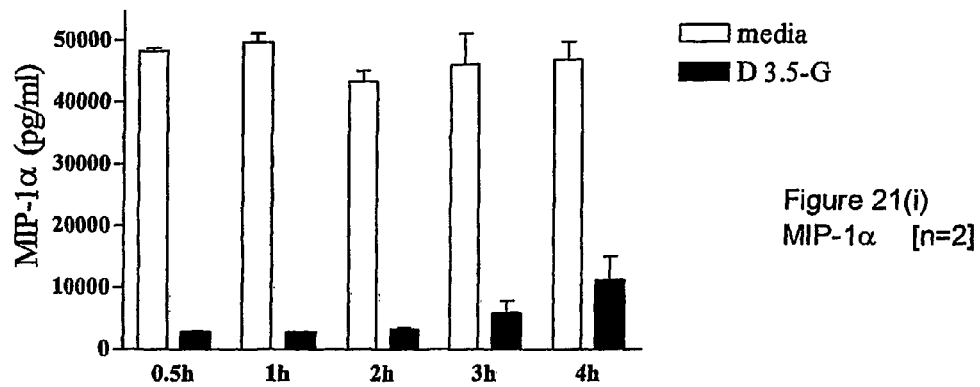

Figure 21(i): Dendrimer gen 3.5-glucosamine ((D 3.5 G at 100 µg/ml) added 30 min or 1 h or 2 h or 3 h or 4 h after LPS (5 ng/ml). Culture supernatants harvested at 21 h.
MIP-1α  [n=2]
MIP-1β  [n=4]
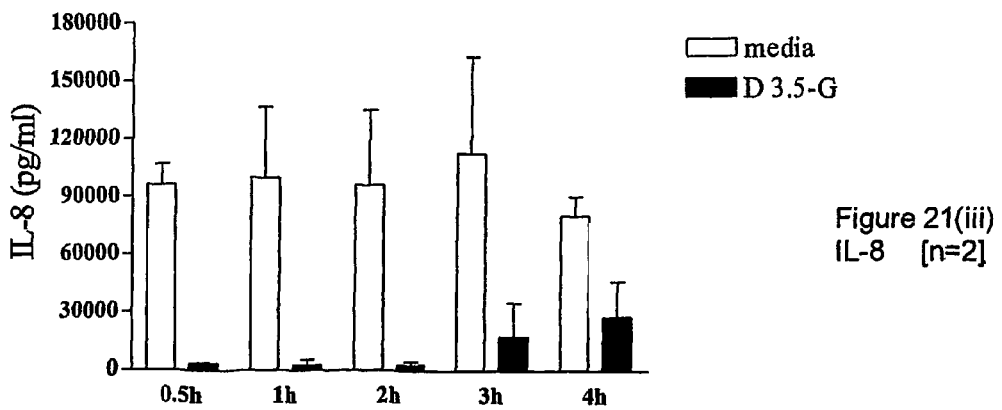
Figure 21(iii)
IL-8  [n=2]

Figure 21:
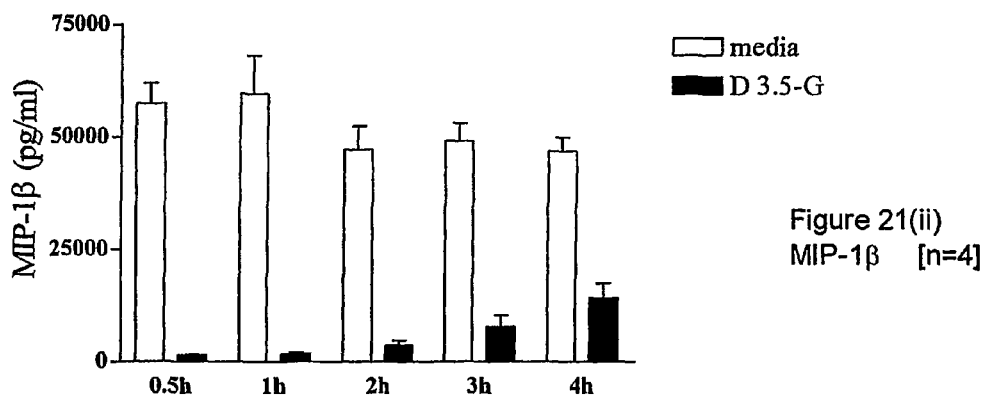
Figure 21:
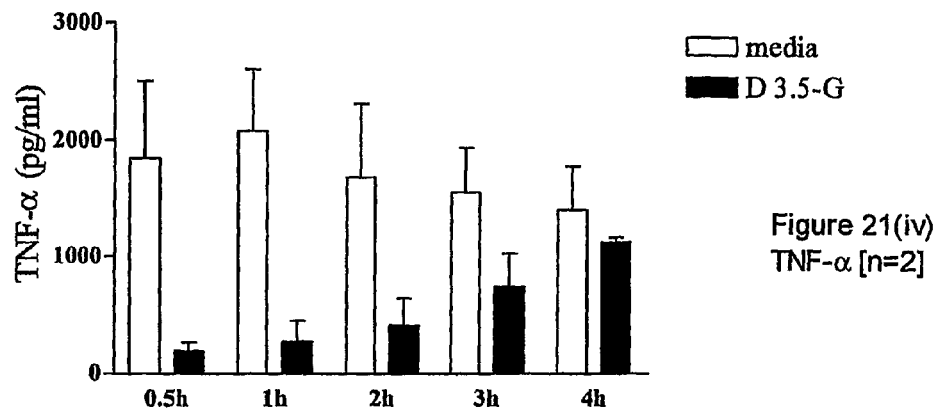

Figure 21(ii): Dendrimer gen 3.5-glucosamine (100 μg/ml) added 30 min or 1 h or 2 h or 3 h or 4 h after LPS (5 ng/ml). Culture supernatants harvested at 21 h.

TNF-α [n=2]

IL-1β [n=2]

IL-6 [n=2]

Release of MIP-1β from single donor PBMN cells. LPS (5ng/ml) was added 30 min after the dendrimer generation 3.5-glucosamine (3% loading) at a concentration of either 150 µg/ml or 300 µg/ml. Culture supernatants were harvested at 22 h (n=1).

Release of TNF-α from single donor PBMN cells. LPS (5ng/ml) was added 30 min after the dendrimer generation 3.5-glucosamine (3% loading) at a concentration of either 150 µg/ml or 300 µg/ml. Culture supernatants were harvested at 22 h (n=1).

PBMN cells from 3 donors mixed [n=2]

PBMN cells from 3 donors mixed [n=2]

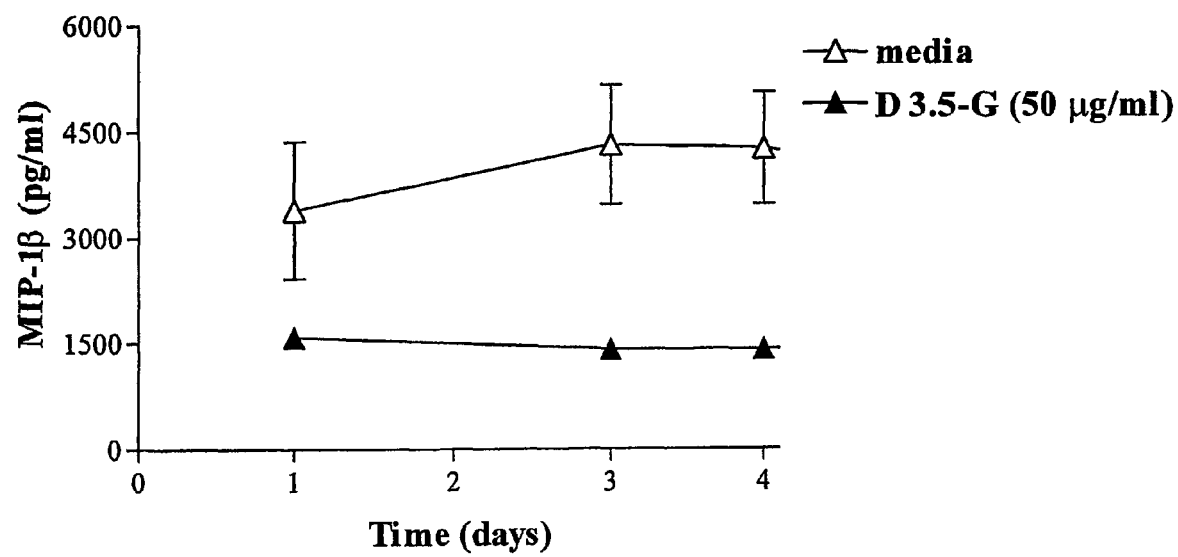

PBMN cells from 2 donors mixed [n=2]

—○— LPS + media

—●— LPS + dendrimer gen 3.5-glucosamine at 100 µg/ml

Donor PBMN cells from 2 individuals mixed, Dendrimer gen 3.5-glucosamine (100 µg/ml) followed immediately by LPS at 10 ng/ml).

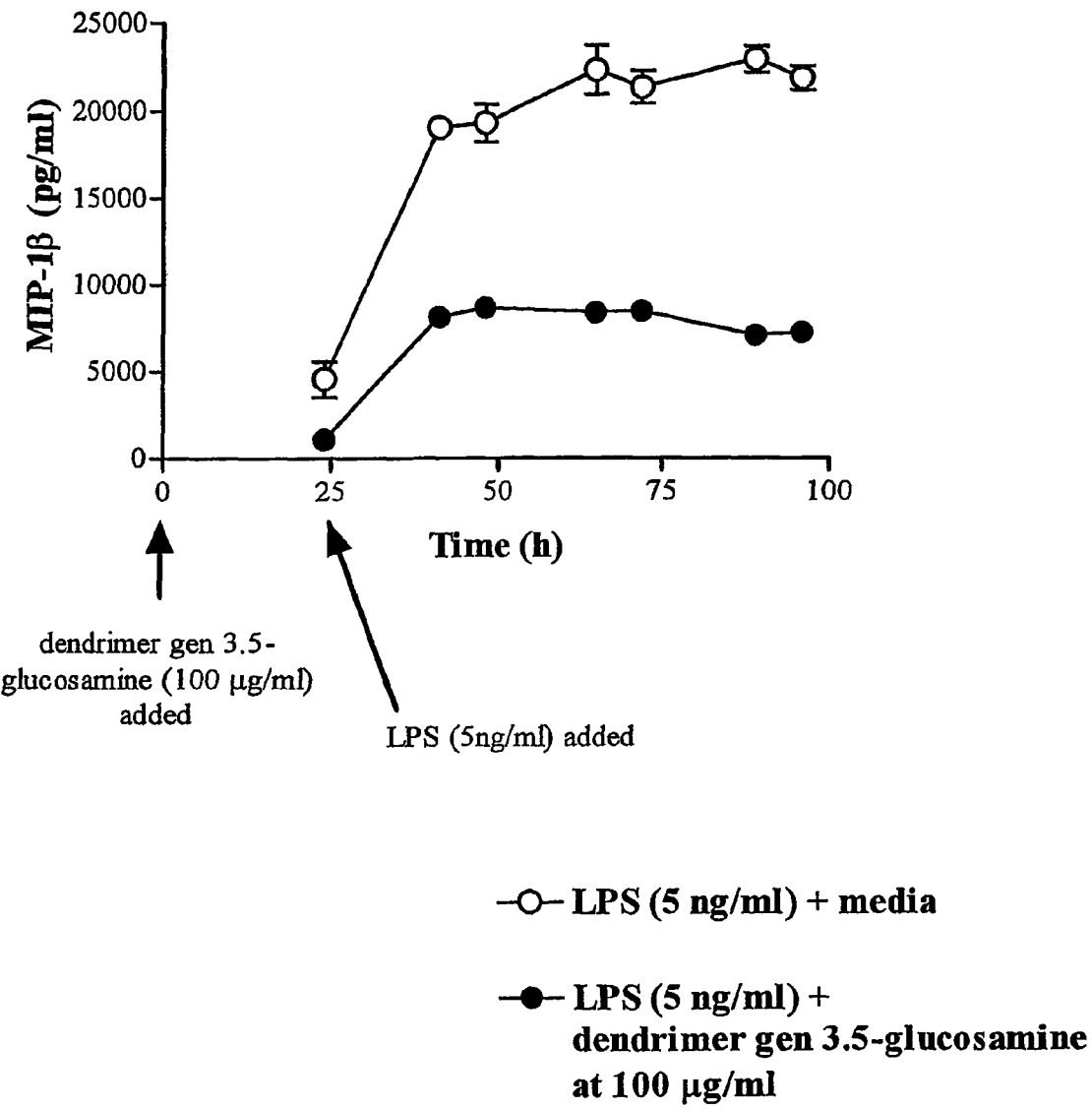

PBMN cell viability when cultured with compounds for up to 5 days.

- DG6S 50 µg/ml
- DG6S 150 µg/ml
- control

PBMN cell counts when cultured with compounds for up to 5 days.

- DG6S 150 µg/ml
- DG6S 50 µg/ml
- control

Cell viability of MDMs when cultured with
dendrimer gen 3.5-glucosamine 6-sulfate over a period of 5 days

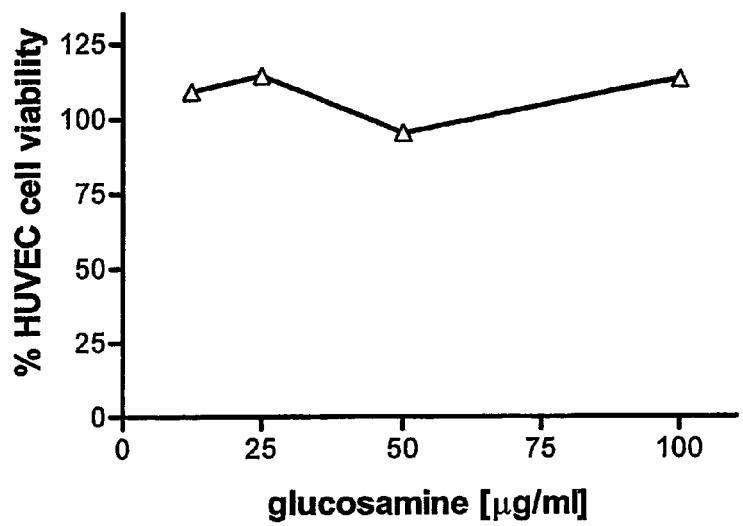
Figure 27 (i)
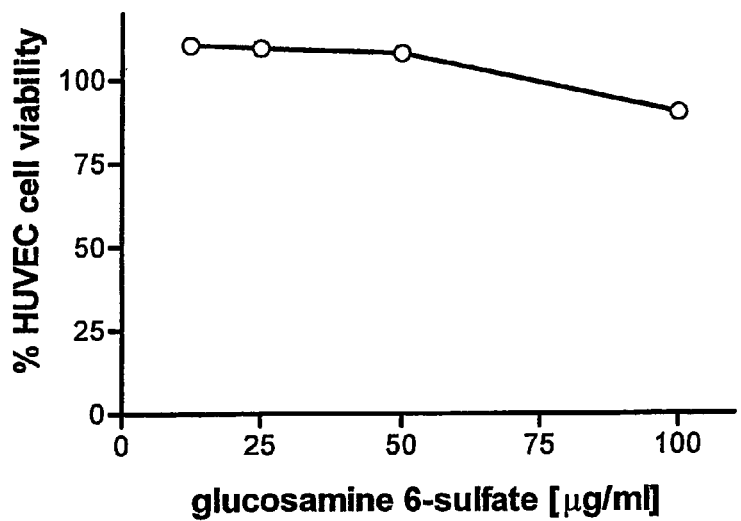
Figure 27 (ii)
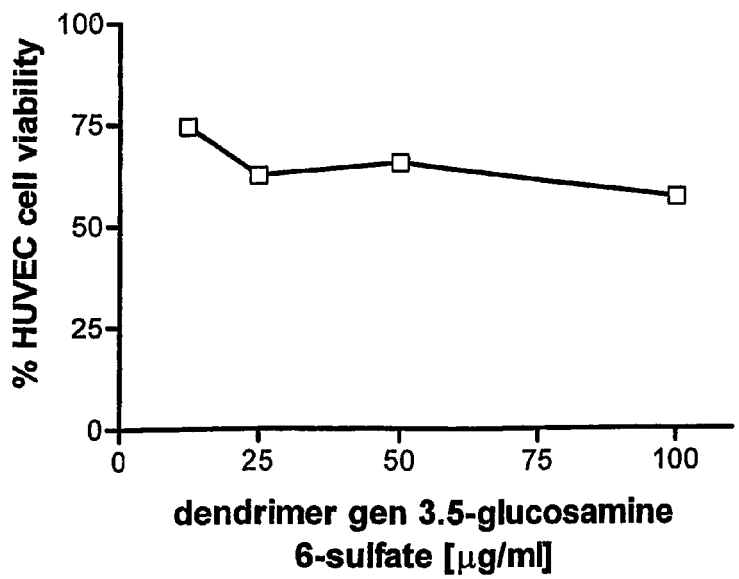
Figure 27 (iii)

MIP-1β release from single donor PBMN cells when treated with dendrimer gen 3.5-glucosamine 6-sulfate at 150 μg/ml or 200 μg/ml for 30 min before the addition of LPS at 5 ng/ml.

TNF-α release from single donor PBMN cells when treated with dendrimer gen 3.5–glucosamine 6-sulfate at 150 µg/ml or 200 µg/ml for 30 min before the addition of LPS at 5 ng/ml.

MDMs from four donors were pooled for 24 h and each of the compounds shown then added at a concentration of 125 μg/ml. Cell free culture supernatants were then harvested at 36 h for measurement of MIP-1β. A reduction in MIP-1β was seen when dendrimer gen 3.5 glucosamine or dendrimer gen 3.5-glucosamine 6-sulfate was present.

* $p<0.05$ compared to the media control

Figure 30:
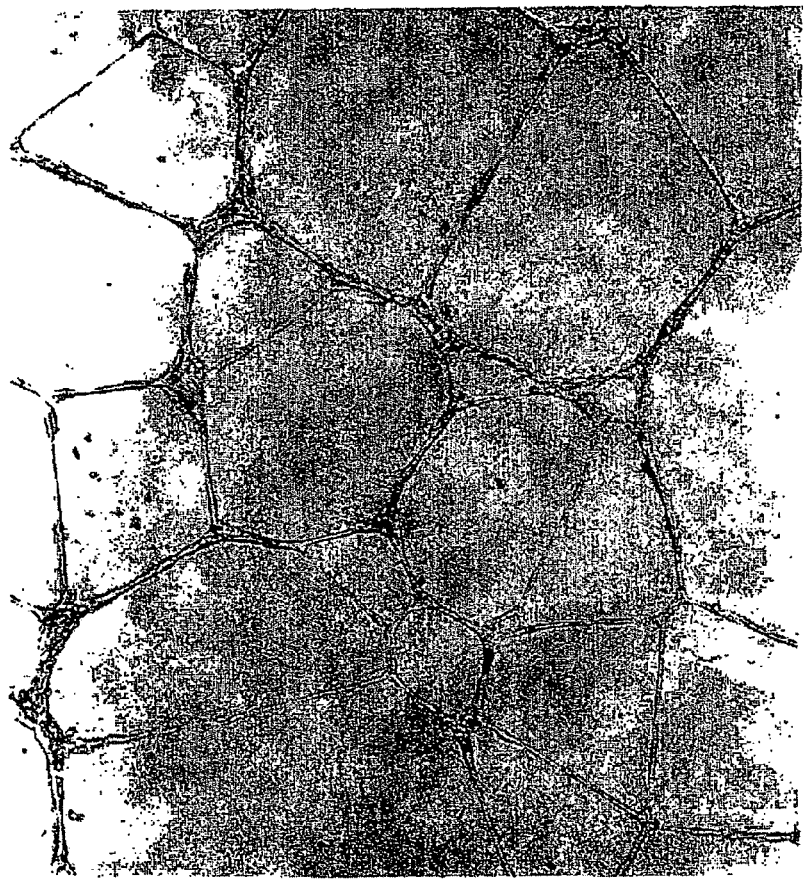

Figure 30: Endothelial microtubule formation by HUVECs on Matrigel (x 40 magnification).
A visual analogue scale was used to determine the extent of tube formation and scored on a scale from 0 (all cells remain single) to 4 (all cells involved in tubular structures) as described in the text.

Control well

Figure 31:
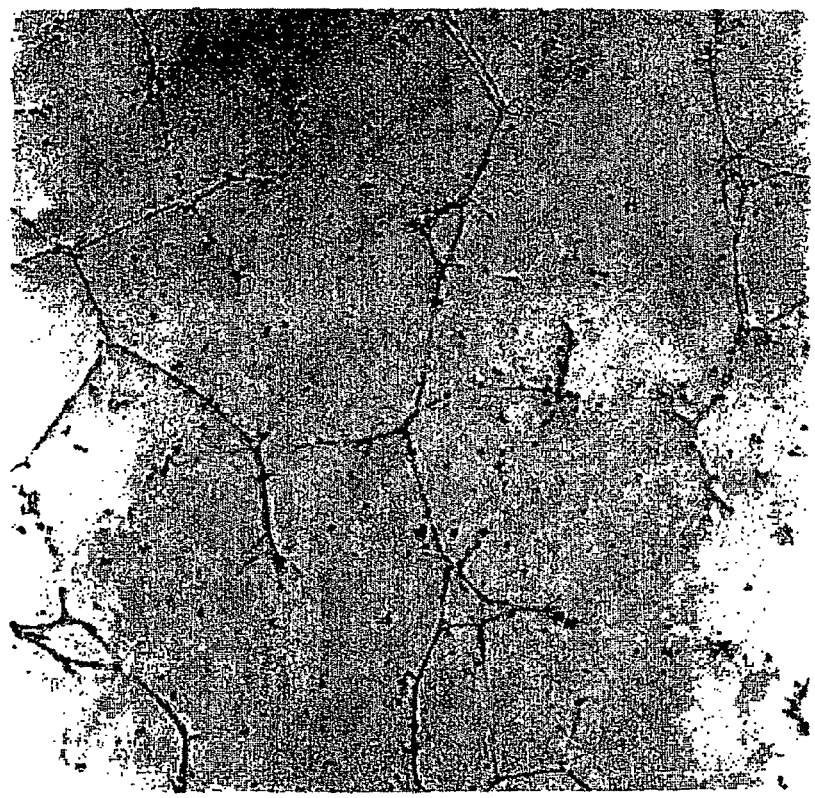

Figure 31: Endothelial microtubule formation by HUVECs on Matrigel (x 40 magnification).
A visual analogue scale was used to determine the extent of tube formation and scored on a scale from 0 (all cells remain single) to 4 (all cells involved in tubular structures) as described in the text.

Dendrimer gen. 3.5-glucosamine 6-sulfate at 12.5 μg/ml

Figure 32:
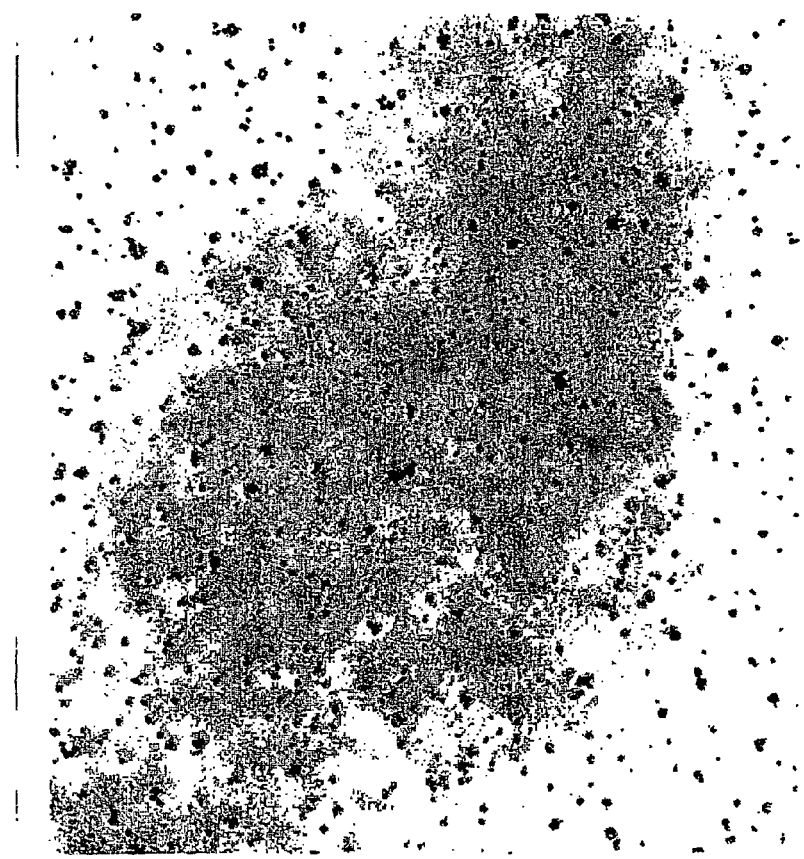

Figures 32: Endothelial microtubule formation by HUVECs on Matrigel (x 40 magnification).
A visual analogue scale was used to determine the extent of tube formation and scored on a scale from 0 (all cells remain single) to 4 (all cells involved in tubular structures) as described in the text.

Dendrimer gen 3.5-glucosamine 6-sulfate at 50 μg/ml

Figure 33:
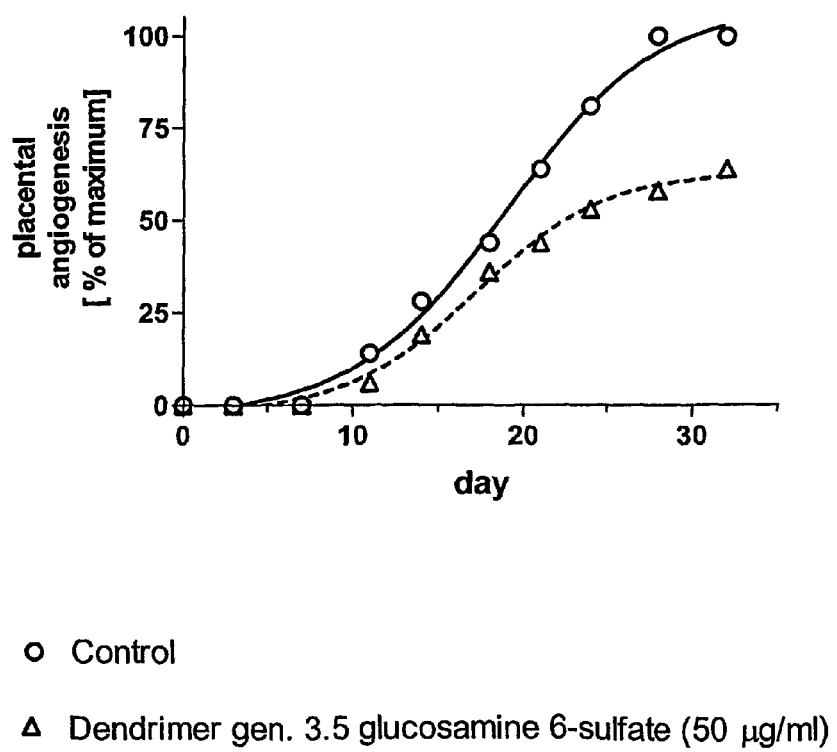
Figure 34:
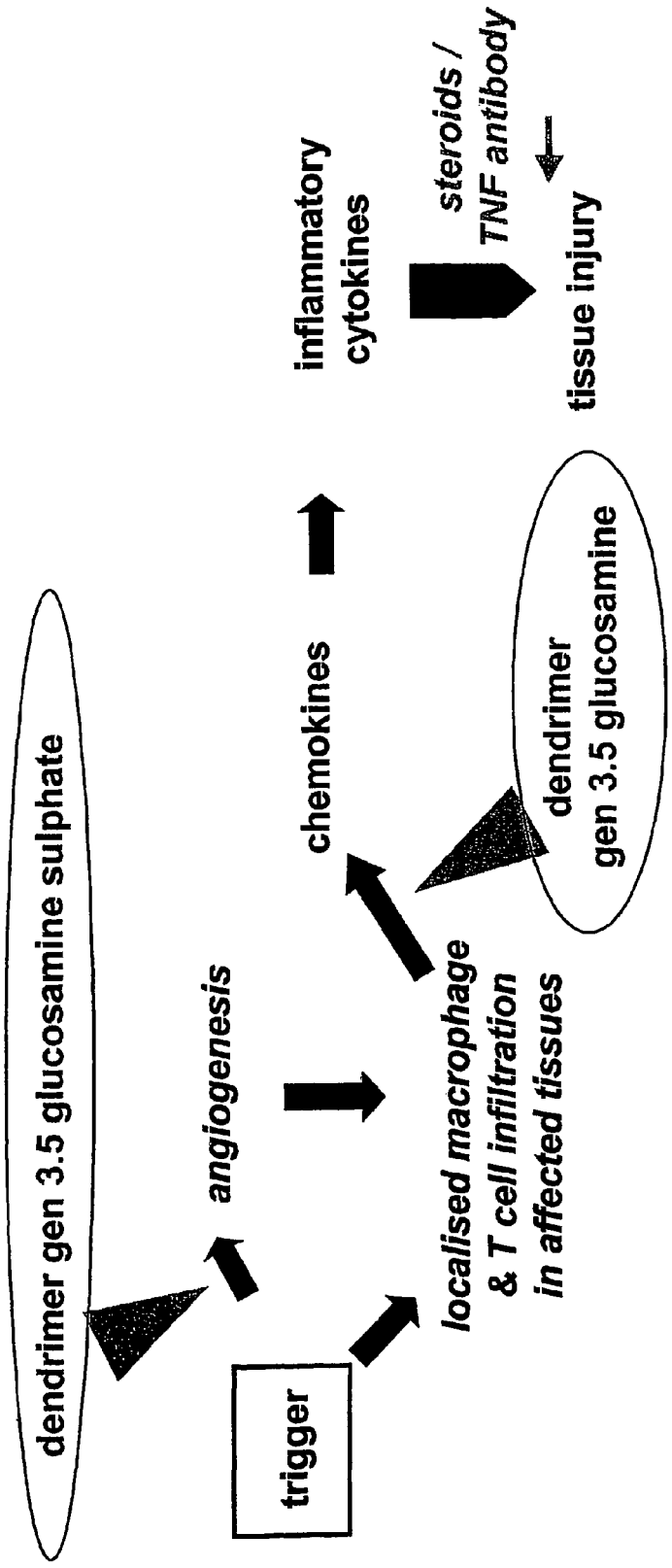

Figure 33: Dendrimer gen. 3.5 glucosamine 6-sulfate reduced the rate of new blood vessel formation in an *in vitro* human placental angiogenesis assay.

○ Control

△ Dendrimer gen. 3.5 glucosamine 6-sulfate (50 μg/ml)

Release of MIP-1β and TNF-α from single donor monocyte derived dendritic cells that were exposed to LPS (5 ng/ml) in the absence and the presence of dendrimer gen. 3.5 glucosamine (D 3.5-G) at 200 µg/ml.

Effect of dendrimer gen. 3.5-glucosamine (200 µg/ml) on the upregulation of CD 25, CD 80, CD 83 and CD 86 on monocyte derived dendritic cells by LPS (5 ng/ml).

▨ Media control
☐ LPS (5 ng/ml)
■ Dendrimer gen. 3.5-glucosamine (200 µg/ml) + LPS (5 ng/ml)

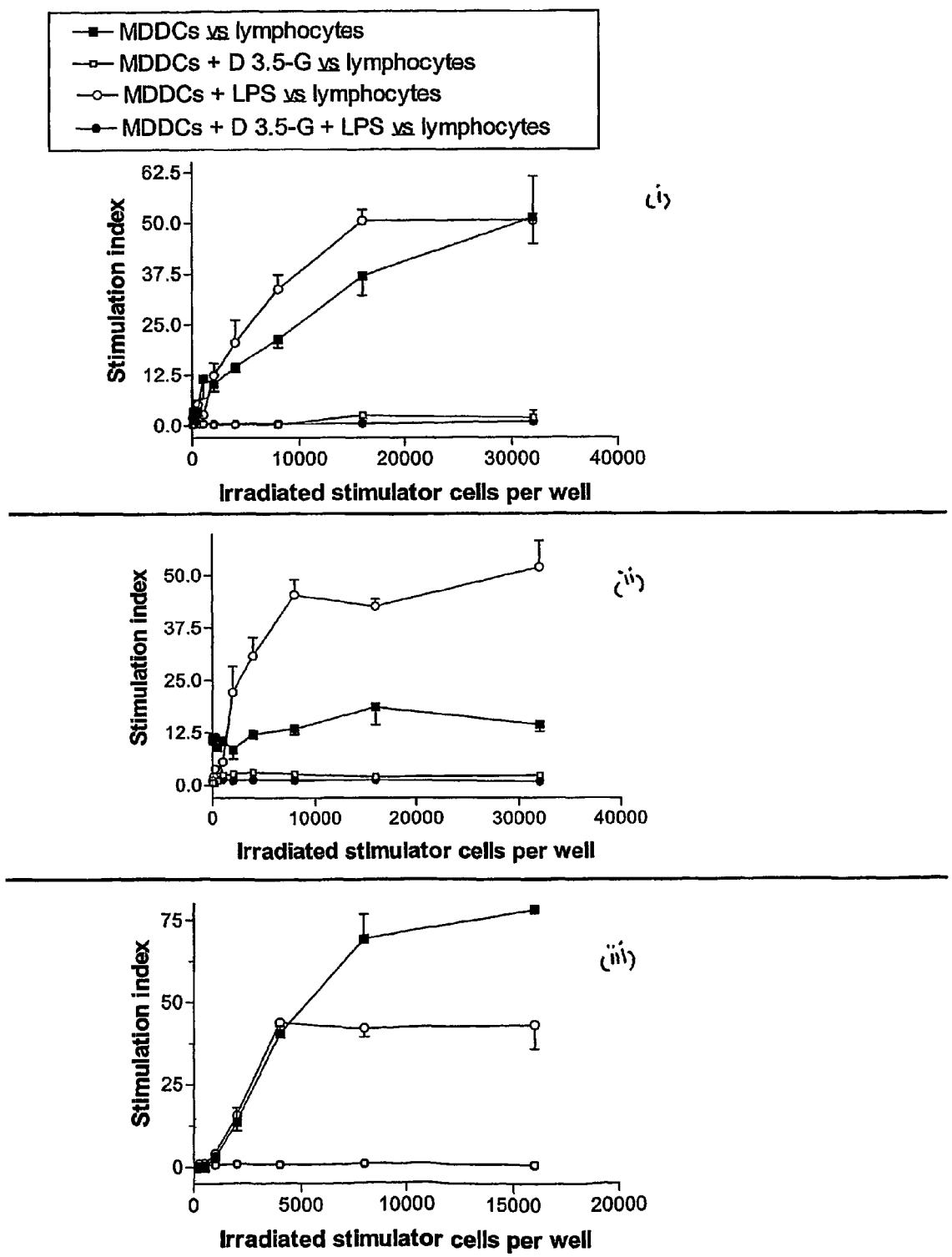
Figure 37: Effect of dendrimer gen. 3.5 glucosamine (D 3.5-G at 200 µg/ml) on the allogenic mixed lymphocyte reaction using monocyte derived dendritic cells (MDDCs) in the absence & the presence of LPS (5 ng/ml).

Figure 38: Effect of dendrimer gen. 3.5 glucosamine (D 3.5-G at 200 µg/ml) on the allogeneic mixed lymphocyte reaction using monocyte derived dendritic cells (MDDCs) in the absence and the presence of LPS (20 ng/ml).
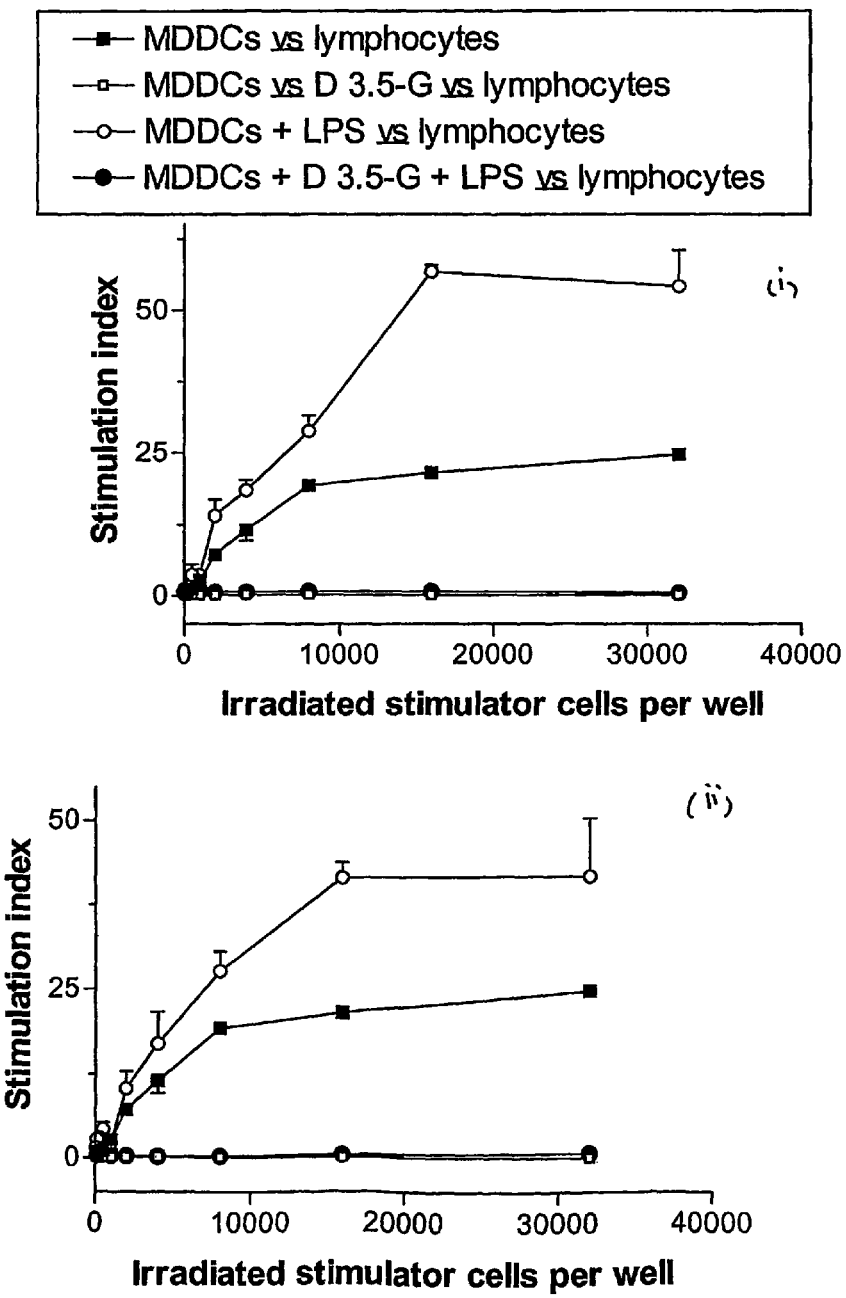

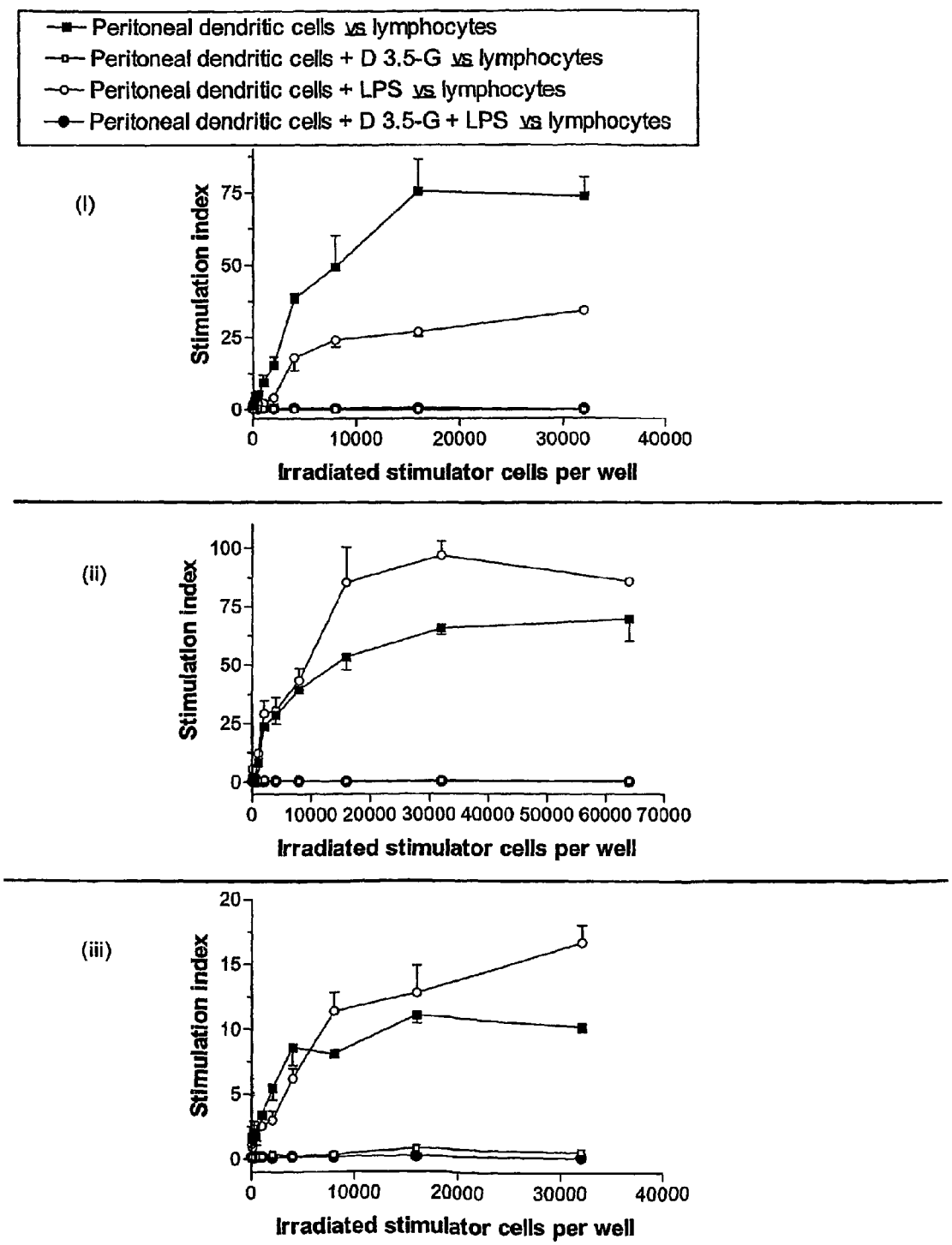
Figure 39: Effect of dendrimer gen. 3.5 glucosamine (D 3.5-G at 200 μg/ml) on the allogeneic mixed lymphocyte reaction using peritoneal dendritic cells in the absence & presence of LPS (5 ng/ml).

Figure 40: Effect of dendrimer gen. 3.5 glucosamine (D 3.5-G at 200 µg/ml) on the allogeneic mixed lymphocyte reaction using peritoneal dendritic cells in the absence and the presence of LPS (20 ng/ml).
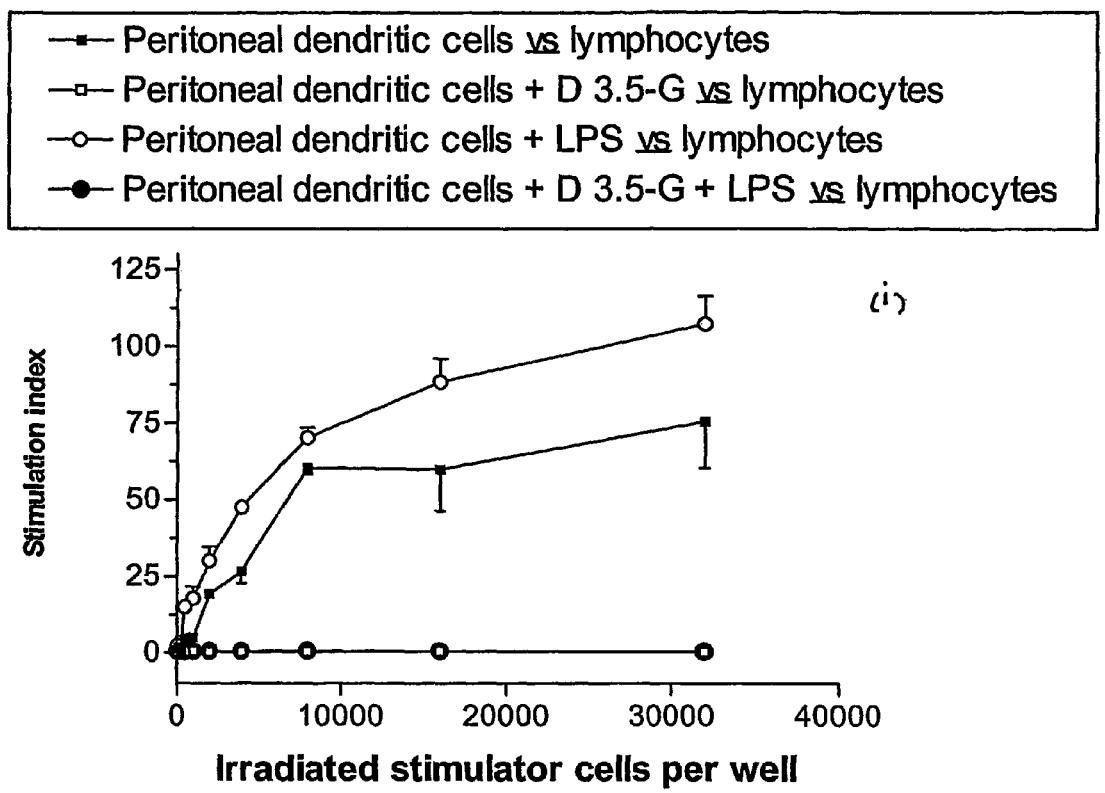
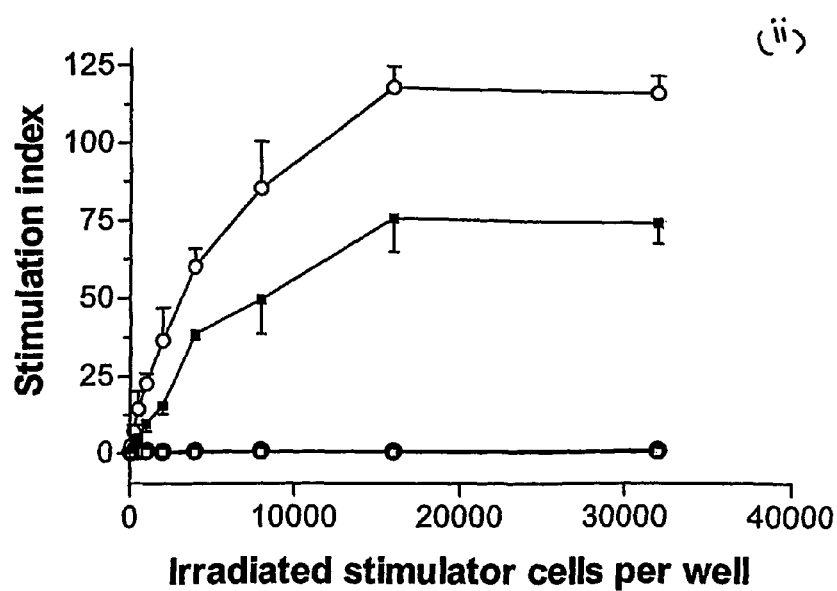

Figure 41:

(i)

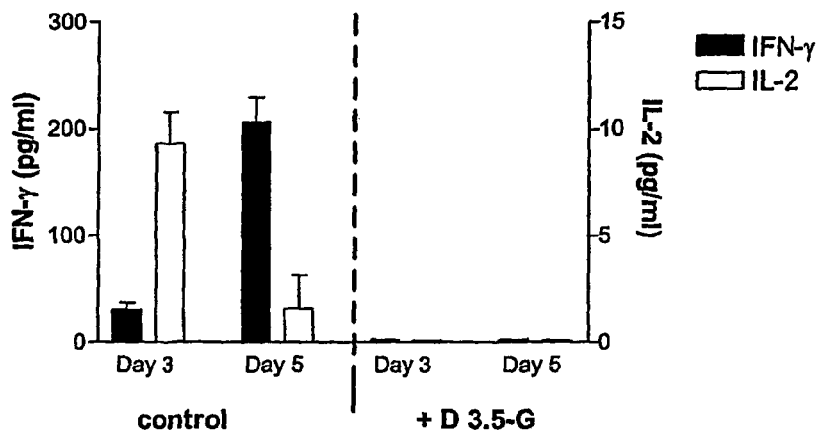

32,000 monocyte derived dendritic cells were stimulated with LPS (20 ng/ml) for 21 h, washed and incubated with 100,000 allogeneic lymphocytes. Cell free supernatants were then analysed at days 3 and 5. (D 3.5-G = dendrimer gen. 3.5 glucosamine)

(ii)

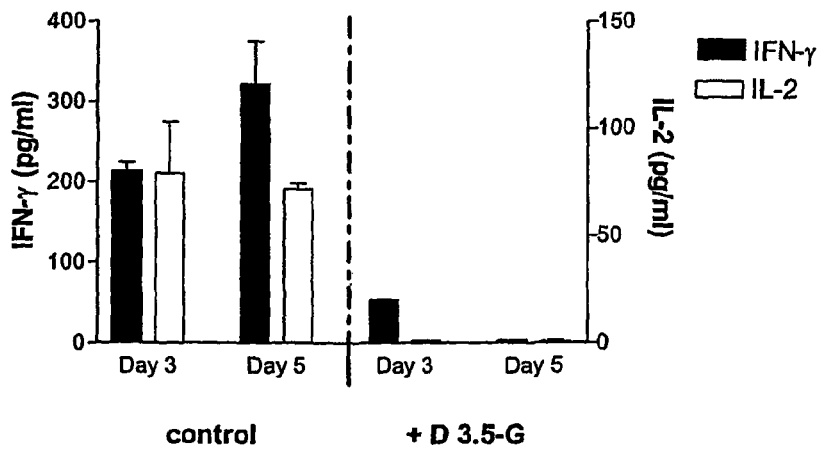

32,000 peritoneal dendritic cells were stimulated with LPS (20 ng/ml) for 21 h, washed and incubated with 100,000 allogeneic lymphocytes. Cell free culture supernatants were then analysed at days 3 and 5.

Release of MIP-1β and TNF-α from single donor PBMN cells that were exposed to SEB (100 ng/ml) in the absence and the presence of dendrimer gen 3.5 glucosamine (D 3.5-G) at 200 μg/ml.

GLYCODENDRIMERS HAVING BIOLOGICAL ACTIVITY

STATEMENT AS TO US GOVERNMENT SPONSORED RESEARCH

This invention was made, in part, with US Government funds from the National Institutes of Health (grant number: 1-R21-A1446901). The US Government has certain rights in the invention.

The present invention relates to new glycodendrimers having new biological activity, processes for preparing them and their use in medicine including veterinary medicine.

Figure 1B:
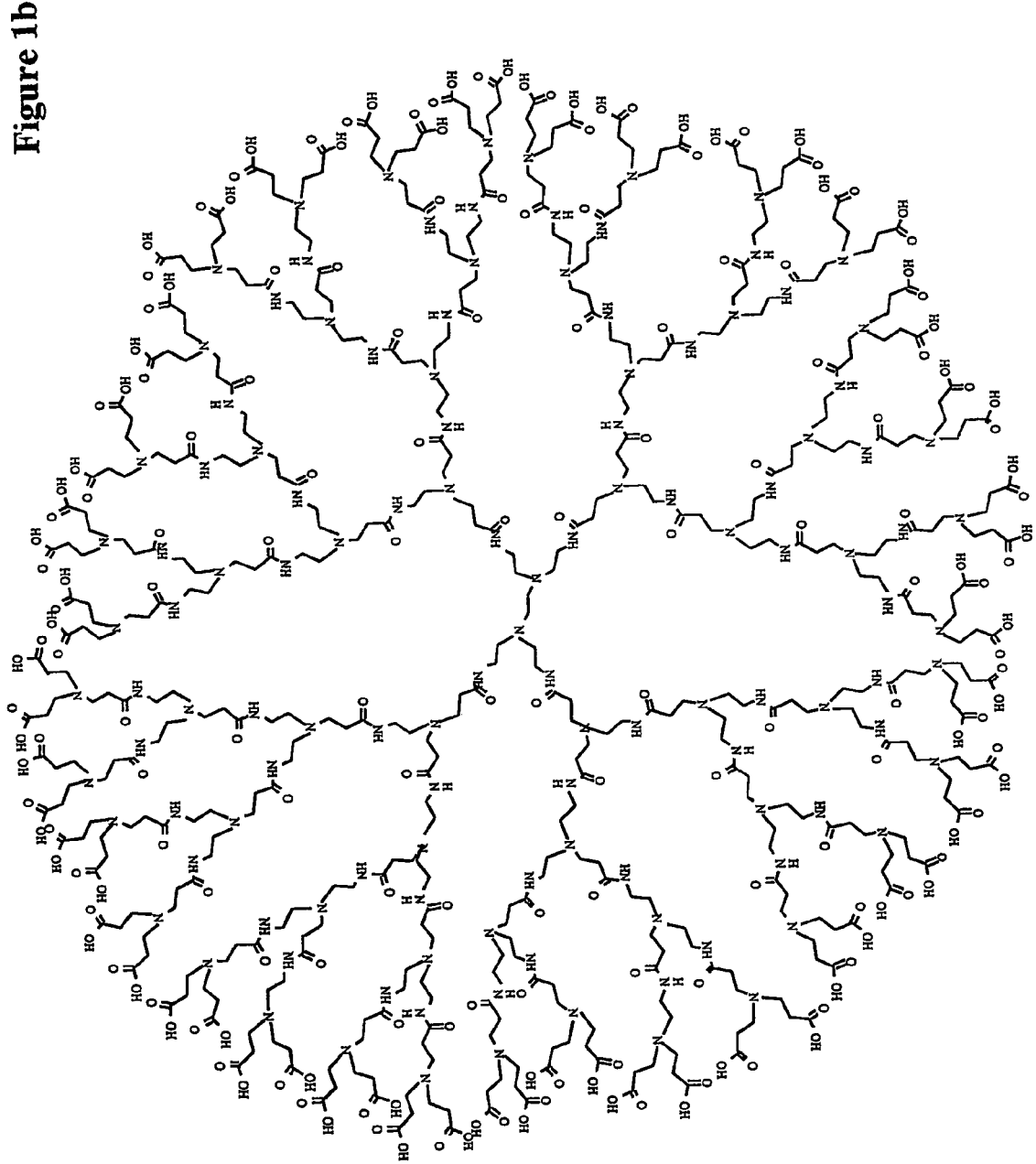

Dendrimers are a class of polymeric compounds that can be distinguished from conventional linear polymers by their highly branched, but circular and symmetrical architecture (FIG. 1a and FIG. 1b). They have a molecular structure that can be much more precisely defined than is possible for linear polymers (Tomalia D A, Naylor A M, Goddard III W A. (1990) Starburst dendrimers: molecular level control of size, shape, surface chemistry, topology and flexibility from atoms to macroscopic matter. Angewandte Chemie-International Edition in English 29, 138-175). STARBURST™ polymers (a trade mark of Dendritech Inc. Midland, Mich.) are dense star polymers. They are a particular type of dendrimer which is formed by the generational addition of branched layers from a core. Typically, they are available in generations 1.5, 2.5, 3.5, 5.5, 7.5, and 9.5. Generation is a term which relates to the way the molecules are synthesised and to their molecular weight. They have from 16 (gen 1.5) up to 4,096 (gen 9.5) terminal carboxylic acid groups.

WO 95/24221 [Dow Chemical Company] discloses dendritic polymer conjugates comprising dense star polymers complexed or conjugated with biological response modifiers.

The reactive end groups of dendrimers are present at the periphery of the molecule and these groups can be cationic or anionic (Newkome G R, Nayak A, Behera R K, Moorefield C N, Baker G R & Johnson A L. (1992) Chemistry of micelles series .22. cascade polymers—synthesis and characterization of 4-directional spherical dendritic macromolecules based on adamantane. Journal of Organic Chemistry 57, 358-362). End group modification is usually employed in dendrimers that have been prepared by the divergent approach:—i.e. poly (amidoamine) dendrimers (PAMAM dendrimers) and poly (propyleneimine) dendrimers (DAB dendrimers). Such modification of the functional groups on the outer surface of the dendrimer can significantly alter the biological properties of these molecules as a consequence of co-operative effects (Jansen J F G A, de Brabander-van de Berg E M M & Meijer E W. (1994) Encapsulation of guest molecules into a dendritic box. Science 266, 1226-1229). Compounds able to produce co-operative effects are very important in modulating biological control mechanisms in the immune system.

Previously it has not proved possible to covalently couple biological molecules to anionic dendrimers in order to make new compounds with novel and unique biological activity.

Figure 2:
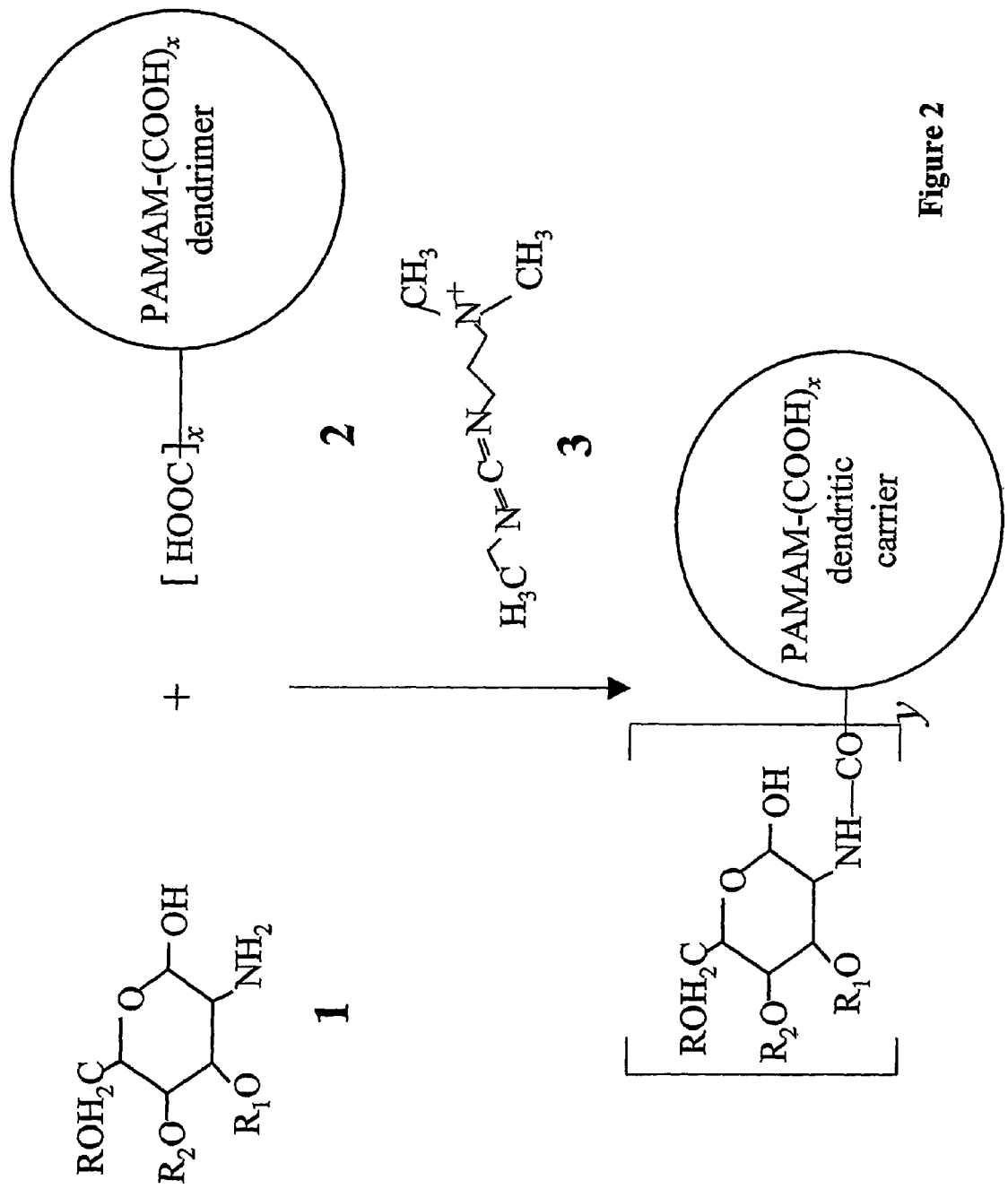

The present invention now provides a process to covalently link a molecule, for example, a biologically active molecule to an anionic dendrimer wherein the dendrimer is reacted with the biologically active molecule in the presence of a coupling agent, for example, a carbodiimide coupling agent, for example, 1-ethyl-3-(3-dimethylaminopropyl) carbodiimide hydrochloride (FIG. 2). The reaction is preferably carried out in an aqueous solvent. The molecule to be linked to the dendrimer, for example, a biologically active agents, includes drugs, nucleic acids (in particular DNA), proteins, peptides, carbohydrates and antibodies of natural or synthetic origin.

The process of the present invention has the advantages of comprising single step, water based chemistry, which can be performed at room temperature (i.e. typically below 40° C.). The process of the present invention has the further advantage that it avoids the need for organic solvents that are often toxic in vivo. Furthermore, organic solvents require additional, complicated and expensive purification of the product from the organic solvent. Conjugation, that is to say, covalent linkage of the components, in an aqueous environment facilitates the purification of the final product. This is important from an industrial, manufacturing perspective for the new drugs. A particular advantage of the process of the present invention is that conjugation can be carried out at ambient room temperature and does not require the application of an external energy source.

The process of the present invention is particularly useful for the preparation of anionic glycodendrimers.

In 1996, Roy defined glycodendrimers as "a new class of low molecular weight multiantennary carbohydrate containing biopolymers" (Page D & Roy R. (1997) Synthesis and biological properties of mannosylated Starburst poly(amidoamine) dendrimers. Bioconjugate Chemistry 8, 714-723). They were synthesised by convergent approaches with incorporation of various carbohydrate structures at the last step.

Glycodendrimers have been described by the manner in which saccharide residues are incorporated as complexes or conjugates into them as one of two types (Ashton P R, Boyd S E, Brown C L, Nepogodiev S A, Meijer E W, Peerlings H W I & Stoddart J F. (1997) Synthesis of glycodendrimers by modification of poly(propyleneimine) dendrimers. Chemistry a European Journal 3 (6), 974-98420):

(i) carbohydrate coated dendrimers characterised by the presence of saccharide residues attached to the end groups of the dendrimer.

(ii) fully carbohydrate dendrimers where the saccharides are used as multifunctional building blocks giving rise to dendrimers that are totally carbohydrate.

Although it is known that neoglycoconjugates can be prepared by linking saccharides to carriers, only those preformed dendrimers bearing primary amino groups on their periphery have been investigated as a macromolecular support for the attachment of carbohydrates (Ashton P R, Boyd S E, Brown C L, Nepogodiev S A, Meijer E W, Peerlings H W I & Stoddart J F. (1997) Synthesis of glycodendrimers by modification of poly(propyleneimine) dendrimers. Chemistry a European Journal 3 (6), 974-984). In these cases, the primary amine terminated dendrimers can be modified with relative ease with a variety of reagents. In contrast, it had not been possible to modify the carboxylic acid groups on the surface of carboxylic terminated, anionic dendrimers in order to give the dendrimer different functional activity. The biological problem that this has led to is that aminic terminated dendrimers are considerably more toxic than the carboxylic terminated dendrimers in vivo (Malik N, Wiwattanapatapee R, Klopsch R, Lorenz K, Frey H, Weener J W, Meijer E W, Paulus W & Duncan R. (2000) Dendrimers: Relationship between structure and biocompatibility in vitro, and preliminary studies on the biodistribution of $^{125}$I-labelled polyamidoamine dendrimers in vivo. Journal of Controlled Release 65, 133-148). Therefore it was important to develop new glycodendrimers that were based upon carboxylic terminated dendrimers as the starting material.

In a further aspect, the present invention now provides new anionic glycodendrimers comprising covalently linked carboxylic terminated dendrimers. A glycodendrimer of the present invention comprises a carbohydrate moiety covalently linked to an anionic dendrimer, in particular a carboxylic terminated dendrimer. The term 'a glycodendrimer' is used herein to include glycodendrimers that comprise more than one species of carbohydrate moiety covalently linked to one species of carboxylic terminated dendrimer, glycodendrimers that comprise one species of carbohydrate covalently linked to a mixture of species of carboxylic terminated dendrimer dendrimers, and glycodendrimers that comprise more than one species of carbohydrate moiety covalently linked to a mixture of species of carboxylic terminated dendrimers.

A carboxylic terminated dendrimer is, for example, a carboxylic terminated dendrimer from any of generations 1.5 to 9.5, for example, generation (gen) 2.5 or gen 3.5. A mixture of species of carboxylic terminated dendrimer is, for example, a mixture of carboxylic terminated dendrimers of different generations, for example, from gen (generation) 1.5 to gen 9.5. For example, a gen 2.5 or gen 3.5 dendrimer may be used alone or in combination with any one or more other generation denrimers.

The carboxylic terminated dendrimer may be, for example, a carboxy terminated poly(amidoamine) (PAMAM) dendrimer. For example, one or more PAMAM dendrimers from gen 1.5 to gen 9.5 may be used, for example, a mixture generations of PAMAM dendrimers from generation 1.5 to generation 9.5 may be used. For example, a dendrimer may be or may comprises a PAMAM dendrimer gen 2.5 or 3.5.

Preferably the dendrimers are PAMAM dendrimers; particularly preferred PAMAM dendrimers are generation 3.5, which have up to 64 terminal carboxylic acid groups.

A carbohydrate moiety is covalently linked to the carboxylic terminated dendrimer. The carbohydrate group may be, for example, a monosaccharide, disaccharide, trisaccharide, oligosaccharide or polysaccharide, or a combination of one or more thereof. The carbohydrate group generally comprises one or more amine groups.

The carbohydrate moiety is preferably an amino sugar or a sulphated amino sugar, which amino sugar or sulphated amino sugar may be modified, for example, acylated, for example, N-acylated. The carbohydrate group may be derived, for example, from glucose, mannose or galactose. The carbohydrate group is, for example, glucosamine, a glucosamine sulphate, N-acetyl glucosamine or an N-acetyl glucosamine sulphate group. A glucosamine sulphate may have one or more sulphate groups, for example, at any one or more of positions 3, 4 and 6. A glucosamine sulphate is, for example, glucosamine 6-sulphate, glucosamine 3,6-disulphate or glucosamine 3,4,6-trisulphate. A glusosamine sulphate may be acetylated, for example, N-acetylated. An N-acetyl glucosamine sulphate is, for example, N-acetyl glucosamine 6-sulphate, N-acetyl glucosamine 3,6-disulphate or N-acetyl glucosamine 3,4,6-trisulphate.

Mannosamine and galactosamine and derivatives thereof, for example, sulphated and/or acylated derivatives corresponding to the above glucosamine derivatives, for example, glucosamine sulphates and N-acylated glucosamine and N-acylated glucosamine sulphates may be used.

A glycodendrimer of the present invention is, for example, dendrimer gen. 3.5-glucosamine or dendrimer gen. 3.5-glucosamine 6-sulphate or dendrimer gen. 3.5-N-acetylglucosamine or dendrimer gen. 3.5-N-acetylglucosamine sulphate or dendrimer gen. 3.5-mannosamine or dendrimer gen. 3.5-mannosamine sulphate or dendrimer gen. 3.5-N-acetylmannosamine or dendrimer gen. 3.5-N-acetylmannosamine sulphate or any combination thereof.

Preferably, the dendrimers are covalently linked to compounds containing aminic groups, for example, amine groups, for example, primary amine groups, such as aminic sugars and sulphated sugars. Preferred sugars are glucosamine or sulphated glucosamine.

The one-step reaction of the present invention may be used for the covalent conjugation of PAMAM anionic dendrimers gen 2.5 to sugars containing aminic groups and to sulfated sugars containing aminic groups.

Linear molecules, that is molecules without a ring structure, can also be attached to the anionic PAMAM dendrimers using the same chemistry. This has been successfully achieved for 3-amino-1-propanesulfonic acid for example.

Typically the covalent linker bond is stable over a period of at least 90 days.

Subsequent purification of the products has also been made simple and straightforward. Until now, it has only been possible to covalently link molecules to cationic PAMAM dendrimers using multistep organic chemistry followed by a large number of purification steps.

Carboxylic acid terminated anionic PAMAM dendrimers have a remarkable lack of toxicity both in vitro and in vivo compared to cationic PAMAM dendrimers (Tsutsumiuchi K, Aoi K, & Okada M. (1999) Globular carbohydrate macromolecule "Sugar Balls" IV. Synthesis of dendritic nanocapsules with molecular recognition sites on periphery. Polymer Journal 31, 935-941). Cationic dendrimers cause red cell haemolysis at a concentration of 10 μg/ml whilst anionic dendrimers have no such effect even at 2,000 μg/ml. Anionic dendrimers have a longer circulation time in the systemic vascular circulation than cationic dendrimers, and this is associated with a lower degree of accumulation of the molecule in the liver. This inherent toxicity of higher generation cationic dendrimers means that they are unlikely to be suitable or safe for either high dose intravenous administration or for repeated intravenous administration (Malik N, Wiwattanapatapee R, Klopsch R, Lorenz K, Frey H, Weener J W, Meijer E W, Paulus W & Duncan R. (2000) Dendrimers: Relationship between structure and biocompatibility in vitro, and preliminary studies on the biodistribution of $^{125}$I-labelled polyamidoamine dendrimers in vivo. Journal of Controlled Release 65, 133-148).

In a preferred aspect of the present invention the attachment of molecules, for example, non-biologically active molecules, to anionic PAMAM dendrimers allows the effective manipulation of chemokines and, in turn cytokines, as well as new blood vessel formation even though dendrimers, and molecules such as glucosamine and glucosamine 6-sulphate, have no proven intrinsic anti-inflammatory or antiangiogenic activity.

Glucosamine is a sugar moiety that can be conjugated to the dendrimer core via the ability of the amine group to react with the carboxylate groups present on the surface of anionic dendrimers. This leads to the formation of a stable amide bond. Glucosamine containing various combinations of sulfate moieties at the 3', 4' and 6' positions of the glucan moiety were also suitable for attachment using the same chemistry. This resulted in the formation of a new anti-angiogenic glycodendrimer with immunomodulatory properties and antiangiogenic properties.

The number of molecules of sugar or sulfated sugar covalently bound to the surface of the dendrimer increases in proportion to the number of carboxylic groups that are present on the surface of the dendrimer. The amount of glucosamine linked to the dendrimers, expressed as a percentage of converted carboxylic groups may range, for example, from 1.5 to 10.1%. In the case of the sulfated dendrimers, the sulphur content increased in the following order: monosulfated sugar (2.79% m:m S); disulfated sugar (5.78% m:m S); trisulfated sugar (7.93% m:m S). The amount of sulfate present in the conjugate was 6% for glucosamine 6-sulfate, 11% for glucosamine 3,6-disulfate, and 15% for glucosamine 3,4,6-trisulfate.

The present invention also provides a glycodendrimer of the present invention for use as a medicament, and further provides methods of treatment of various diseases and conditions comprising administering an effective amount of a glycodendrimer of the invention to a subject, generally a human, in need of such treatment. For use as a medicament or in medical treatment, a glycodendrimer of the present invention is preferably produced according to the process of the present invention using an aqueous solvent. The term 'treatment' is used herein to mean treatment and/or prevention, as appropriate. The invention includes the use of the glycodendrimers of the invention in veterinary medicine.

These new anionic glycodendrimers downregulate the immune system by acting first and foremost on the release of chemokines, most notably macrophage inflammatory protein (MIP) 1β, MIP-1α and interleukin 8 (I0L-8. The compounds inhibit the release of pro-inflammatory chemokines which, in turn, inhibits the release of pro-inflammatory cytokines most notably tissue necrosis factor (TNF)-α, IL-1β and IL-6. The compounds of the invention also have antiangiogenic properties.

Accordingly, the present invention also provides a glycodenrimer of the present invention for use as a medicament for the treatment of a disease in which chemolines and cytokines are increased, and also provides a method of such treatment, and the use of a glycodendrimer of the present invention for the manufacture of a medicament for such treatment.

The compounds of the invention are particularly useful in the treatment of, for example, sepsis, severe sepsis, septic shock, the systemic inflammatory response associated with sepsis, rheumatological disease, eczema, psoriasis, contraction of tissues during wound healing, excessive scar formation during wound healing, transplant rejection, graft versus host disease and various conditions associated with angiogenesis in animals and man. A glycodendrimer of the iinvention may be used therapeutically or prophylactically.

Rheumatological and inflammatory conditions include rheumatoid arthritis, juvenile chronic arthritis, psoriatic arthritis, reactive arthritis occuring after an infection, active ankylosing spondylitis, arthritis associated with inflammatory bowel disease, Behcet's disease including Behcet's disease with panuveitis and/or retinal vasculitis, psoriasis, inflammatory bowel disease (Crohn's disease, ulcerative colitis).

Further conditions include allogeneic organ and tissue transplantation, graft versus host disease. A transplant may be a corneal, kidney, heart, lung, heart-lung, skin, liver, gut or bone marrow transplant. Diseases and conditions involving angiogenesis include diseases associated, with metastatic tumour cell growth, which includes many cancers, and diabetic retinopathy. In the case of transplantion, a glycodendrimer of the invention may be adminsitered to the recipient before the transplantation is carried out. Alternatively or in addition, a tissue or organ for transplantaion may be treated with a glycodendrimer of the invention in vitro before transplantation, for example, in the case of a corneal transplant, a glycodendrimer of the invention may be added to the solution in which the cornea is stored before transplantation.

The term 'sepsis syndrome' refers to sepsis plus impaired organ perfusion. The spectrum of clinical syndromes ranging from bacteremia to sepsis to severe sepsis to septic shock to refractory septic shock and to the systemic inflammatory response syndrome represents a continuum in which localised inflammation is at one end with a severe generalised inflammatory response leading to multi-organ failure being at the other end of the spectrum. In severe cases, death can occur within a few hours.

In a preferred aspect of the present invention, the compounds have activity against the systemic inflammatory response syndrome that is associated with bacterial or fungal infections. A glycodendrimer of the present invention may be used to treat sepsis caused by the lipopolysaccharide from gram negative bacteria, or a superantigen toxin from a gram positive bacterium, for example the severe sepsis, the septic shock or the systemic inflammatory response associated with sepsis caused by the lipopolysaccharide from gram negative bacteria, or a superantigen toxin from a gram positive bacterium.

In a further aspect, the present invention provides a pharmaceutical formulation comprising a glycodendrimers of the invention and optionally a pharmaceutically acceptable carrier.

The compounds and formulations of the invention are suitable for administration intravenously, orally, intraperitoneally, topically (skin), buccal, rectally, to the surface of the skin, transdermal (slow release preparation), subcutaneously, intramuscularly, intranasally, by aerosol, by pulmonary adminsitration, and directly to the eye.

Particularly preferred compounds according to the invention are dendrimer gen. 3.5-glucosamine and dendrimer gen 3.5-glucosamine 6-sulphate which have been proven to be useful.

For example in human cell lines, the dendrimer gen 3.5-glucosamine showed $IC_{50}$ toxicity values that ranged from 1,825 to 3,000 μg/ml, and the dendrirner gen 3.5-glucosamine 6-sulfate showed $IC_{50}$ toxicity values that ranged from 246-307 μg/ml. In freshly isolated, human peripheral blood mononuclear (PBMN) cells and in freshly isolated human monocyte-derived-macrophages (MDM), the $IC_{50}$ toxicity value for dendrimer gen 3.5-glucosamine was 340-360 μg/ml. In freshly isolated, human peripheral blood mononuclear cells and in freshly isolated human monocyte-derived macrophages, the $IC_{50}$ toxicity value for dendrimer gen 3.5-glucosamine 6-sulfate, the dendrimer gen 3.5-glucosamine 3,6-disulfate, and the dendrimer gen 3.5-glucosamine 3,4,6-trisulfate was 230-260 μg/ml.

Single donor MDMs were cultured with dendrimer gen 3.5-glucosamine up to a concentration of 150 μg/ml for 72 h. No reduction in cell viability was seen. Single donor HUVECs were cultured with dendrimer gen 3.5-glucosamine up to a concentration of 100 μg/ml for 72 h. No reduction in cell viability was seen. The dendrimer gen 3.5-glucosamine was not toxic to Wistar rats when injected intravenously at a concentration of up to 30 mg/kg.

Neither dendrimer gen 3.5-glucosamine nor dendrimer gen 3.5-glucosamine 6-sulfate affected the release of chemokines or cytokines from immune cells that were in their normal resting state. Activity of these two compounds was only seen when these compounds were cultured with cells that had been immunologically stimulated by an antigen in some way. Therefore, these two compounds do not interfere with the normal homeostatic control under which primary, human cells operate on a day-to-day basis. As such, they differ from all other sulphated polysaccharides.

When single donor PBMN cells are cultured with dendrimer gen 3.5-glucosamine at 100 μg/ml the release of macrophage inflammatory protein-1α (MIP-1α; chemokine), macrophage inflammatory protein-1β (MIP-1β; chemokine), Interleukin-8 (IL-8; chemokine), Tumor Necrosis Factor-α (TNF-α; cytokine), Interleukiln-1 (gLLP1; cytoline) and Interleukin-6 (IL6; cytokine) by lipopolysaccharide (LPS) at 5 ng/ml is significantly reduced. When single donor PBMN cells are cultured with dendrimer gen 3.5-glucosamine at 200 μg/ml the release of MIP-1α, MIP-1β, IL-8, TNF-α, IL-1β and IL-6 by LPS at 5 ng/ml is significantly reduced. When single donor PBMN cells are cultured with LPS at 5 ng/ml for 30 min, or 1 hour, or 2 hours, or 3 hours, or 4 hours before the addition of dendrimer gen 3.5-glucosamine at 100 μg/ml, the release of MIP-1α, MIP-1β, IL-8, TNF-α, IL-1β and IL-6 is significantly reduced. It has been shown that the dendrimer gen 3.5-glucosamine is not mediating its activity by binding to the LPS used in these experiments. It is believed that the dendrimer gen. 3.5-glucosamine and dendrimer gen. 3.5-glucosamine 6-sulphate mediate their effects by acting as polyvalent binding inhibitors of the immunoregulatory functions of dendritic cells and of lymphocytes. This action is mediated through toll like receptors, chemokines and cytokines.

When single donor PBMN cells are cultured with dendrimer gen 3.5-glucosamine at 300 μg/ml whose loading with glucosamine is only 3% (rather than the 7% used in all other experiments), the release of MIP-1α, MIP-1β, IL-8, TNF-α, IL-1β and IL-6 by LPS at 5 ng/ml is significantly reduced. When single donor PBMN cells from 2 or 3 individuals are mixed together and dendrimer gen 3.5-glucosamine is added at 50 μg/ml, there is a significant reduction in the release of MIP-1β and TNF-α. When single donor PBMN cells from 2 or 3 individuals are mixed together and dendrimer gen 3.5-glucosamine is added at 100 μg/ml, followed by LPS at 5 ng/ml or 10 ng/ml, there is a significant reduction in the release of MIP-1β.

None of the compounds described (ie: dendrimer gen 3.5-glucosamine, dendrimer gen 3.5-glucosamine 6-sulfate, dendrimer gen 3.5-glucosamine 3,6-disulfate, or dendrimer gen 3.5-glucosamine 3,4,6-trisulfate) has any anticoagulant activity as determined using the following in vitro assays:—kaolin partial thromboplastin time, prothrombin time, thrombin time and a Factor Xa assay. No anticoagulant activity was seen at the maximum concentration of 200 μg/ml that was analysed for all of the compounds tested. For dendrimer gen 3.5-glucosamine, this was also confirmed at a concentration of 300 μg/ml. The compounds of the present invention constitute the first group of sulphated polysaccharides that have been synthesised that have no anticoagulant activity. They are therefore particularly suitable for intravenous administration in animal and in man.

New vessel formation is inhibited by a direct effect of dendrimer gen 3.5-glucosamine 6-sulfate on normal endothelial cells. Its effect is to prevent endothelial cells coming together to form new endothelial vessels and to form new blood vessels. In contrast to all other sulphated polysaccharides that have been developed as anti-angiogenic compounds, the dendrimer gen 3.5-glucosamine 6-sulfate synthesised has no anticoagulant activity. The dendrimer gen 3.5-glucosamine 6-sulfate does not affect cell viability or the growth characteristics of PBMN cells or MDMs when present at a concentration of up to 150 μg/ml in cultures of these cells that are maintained for up to 5 days.

The dendrimer gen 3.5-glucosamine 6-sulfate construct is not toxic to HLJVECs when added to cultures of these cells up to a concentration of 100 μg/ml for up to 72 hours.

When single donor PBMN cells are cultured with dendrimer gen 3.5-glucosamine 6-sulfate at 150 μg/ml or at 200 μg/ml, the release of MIP-1β and TNF-α by LPS at 5 ng/ml is significantly reduced.

When single donor MDMs from 4 individuals are mixed and dendrimer gen 3.5-glucosamine or dendrimer gen 3.5-glucosamine 6-sulfate is added at 25 μg/ml, there is a significant reduction in the release of MIP-1β.

Using the human umbilical vein endothelial cell Matrigel assay as an in vitro model of angiogenesis, dendrimer gen 3.5-glucosamine 6-sulfate inhibits new vessel formation and prevents new blood vessel formation; ie: angiogenesis.

Using an in vitro angiogenesis assay based on the outgrowth of new blood vessels from human placentas, dendrimer gen 3.5-glucosamine 6-sulfate causes a reduction in the number of new vessels that are formed when it is present at 25 μg/ml. The effect is significantly greater at 50 μg/ml.

The compounds of the invention are suitable for reducing the severity of the sepsis syndrome in animals and in man. They can be administered intravenously, orally or intraperitoneally at a concentration ranging from 2.5 to 2,500 μg/ml. The preferred concentration is 25 μg/ml to 250 μg/ml.

In rheumatoid arthritis the compounds of the invention slow, abort or even prevent the acute-on-chronic tissue damage that is seen in this disease. The administration of the compounds in rheumatoid arthritis (especially early on in the course of the disease) would significantly reduce the release of the pro-inflammatory chemokines (MIP-1α, MIP-1β and IL-8) which, in turn, would reduce or abolish the release of the pro-inflammatory cytokines (TNF-α, IL-1β and IL-6).

The simultaneous administration of mixtures of two or more compounds of the invention to inhibit the release of pro-inflammatory chemokines and, in turn, inhibit the release of pro-inflammatory cytokines, and to concurrently inhibit angiogenesis is able to result in considerable synergy of action with minimal toxicity. For example the simultaneous administration of dendrimer gen 3.5-glucosamine and dendrimer gen 3.5-glucosamine 6-sulfate provides considerable synergy of action with lower doses and less frequent administration being possible.

The application of topical (ie: skin) preparations of the compounds of the invention to the active plaque lesions of psoriasis or eczema or excessive scar formation or the contraction of tissues during wound healing (especially early on in the course of the disease) results in the healing of these lesions by reducing or preventing endothelial cell proliferation and the angiogenic response.

The application of compounds of the invention to reduce or prevent new endothelial cell formation into vessels during its earliest stages is beneficial for the treatment of the skin lesions of psoriasis or eczema or excessive scar formation or the contraction of tissues that can occur during wound healing. In particular the administration of compounds such as dendrimer gen 3.5-glucosamine is suitable to reduce the release of the pro-inflammatory chemokines MIP-1α, MIP-1β and IL-8) and, in turn, the release of the pro-inflammatory cytokines (TNF-α, IL-1 and IL6).

The simultaneous administration of mixtures such as dendrimer glucosamine and dendrimer glucosamine 6-sulfate to inhibit angiogenesis and to inhibit the release of pro-inflammatory chemokines and, in turn, the release of the pro-inflammatory cytokines results in considerable synergy of action with minimal toxicity in psoriasis. In particular, this provides a therapeutic benefit to the treatment of dermatological and rheumatological conditions.

The compounds of the invention are suitable for administration intravenously, orally, buccal, intraperitoneally, into the joint space, rectally, to the surface of the slin, transdermal (slow release preparation), subcutaneously, intramuscularly, intranasally, to the eyes as eye drops, by intravitreal (i.e. into the eye) injection, or by aerosol (eg. topically to the lungs) at a concentration ranging from 2.5 to 2,500 μg/ml. The preferred concentration is 25 μg/ml to 250 μg/ml.

Crohn's Disease and Ulcerative Colitis are the major forms of inflammatory bowel disease. The oral or intravenous administration of compounds such as dendrimer gen. 3.5-glucosamine and dendrimer gen 3.5-glucosamine 6-sulfate are especially suitable early on in the course of the disease. The drug would accumulate in the tissues associated with the small bowel and the large bowel.

Intervention with a compound of the invention which reduces or prevents new endothelial cell formation into vessels (i.e.: neo-angiogenesis) during its earliest stages is beneficial for the treatment of inflammatory bowel disease.

Intervention with a compound of the invention which reduces or prevents new endothelial cell formation into vessels (i.e.: neo-angiogenesis) during its earliest stages could be beneficial for the prevention of the destructive arthritis that can develop in the clinical course of inflammatory bowel disease.

The administration of compounds of the present invention could significantly reduce the release of the pro-inflammatory chemokines (MIP-1$\alpha$, MIP-1$\beta$ and IL-8) and, in turn, the release of the pro-inflammatory cytokines (TNF-$\alpha$, IL-1 and IL-6) in inflammatory bowel disease.

The simultaneous administration of compounds such as dendrimer gen 3.5-glucosamine and dendrimer gen 3.5-glucosamine 6-sulfate to concurrently inhibit angiogenesis and to inhibit the release of pro-inflammatory chemokines and, in turn, the release of pro-inflammatory cytokines provides for considerable synergy of action with minimal toxicity.

The compounds will accumulate in the inflamed tissues that are central to the pathophysiology of rheumatoid arthritis, inflammatory bowel disease and psoriasis. The endothelial cells associated with areas of inflammation and the increased vascularity caused by the development of angiogenesis will facilitate the accumulation of the compounds into the areas of inflammation.

Particularly advantageous features of the present invention include: the inhibition of the release of chemolines and, in turn, cytokines that results in the rejection of autologous, allogeneic, syngeneic or xenogenic organ transplants, the inhibition of the release of chemokines and, in turn, cytokines, and the angiogenesis that results in the rejection of autologous, allogenic, syngeneic or xenogenic organ transplants, effective maintenance of the counter inflammatory environment that is required to prevent the rejection of the transplanted organ, and effective maintenance of the counter inflammatory environment that is required to prevent the development of graft versus host disease.

In a preferred aspect, the present invention also provides the use of dendrimer gen. 3.5-glucosamine and/or dendrimer gen. 3.5-glucosamine sulfate in any form of organ or tissue transplant. This includes corneal, kidney, heart, lung, liver, gut, skin and bone marrow transplantation.

Dendrimer gen 3.5-glucosamine 6-sulfate has a direct effect on normal endothelial cells which leads to the inhibition of new vessel formation. The administration of dendrimer gen 3.5-glucosamine 6-sulfate to patients provides a way of preventing the angiogenesis that is necessary for the establishment and the subsequent growth and development of a metastatic deposit of malignant cells into a tumour especially if administered early on in the course of the disease.

A drug like dendrimer gen 3.5-glucosamine 6-sulfate or a combination of dendrimer gen 3.5-glucosamine and dendrimer gen 3.5-glucosamine 6-sulfate which reduces or prevents the proliferation of endothelial cells and prevents neo-angiogenesis during the earliest stages of the growth of the metastatic lesion provides a way to abort or even prevent the development of the metastatic lesion.

A particularly preferred formulation for use in patients is dendrimer gen 3.5-glucosamine (7%) and dendrimer gen 3.5-glucosamine 6-sulfate (7%) which is being used at 100 to 200 µg/ml.

Particularly preferred polymers have glucosamine or sulfated glucosamine covalently linked to the anionic dendrimer. The dendrimer gen 3.5-glucosamine and dendrimer gen. 3.5-glucosamine 6-sulfate were found to downregulate the release of the chemokines macrophage inflammatory protein-1$\alpha$, macrophage inflammatory protein-1$\beta$, and interleukin-8, and, in turn, downregulates the release of the cytokines tumour necrosis factor-$\alpha$, interleukin-1$\beta$ and interleukin-6 from human peripheral blood mononuclear cells.

Compounds of the present invention such as dendrimer gen 3.5-glucosamine can also be used in combination with existing and accepted therapeutic approaches as adjuvant therapy. For example, in the sepsis syndrome they could be used with antibacterial drugs or antifungal drugs. In rheumatoid arthritis and related conditions, Behcet's disease, inflammatory bowel disease and psoriasis, they could be used with steroids and disease modifying drugs such as methotrexate or disease modifying therapeutic antibodies. In the treatment of cancer metastases, they could be used with anti-mitotic drugs. In the treatment of organ transplant rejection, and in graft versus host disease, they could be used with steroids and/or cyclosporin and/or FK506 and/or azathioprine and/or tacrolimus and/or sirolimus and/or basiliximab and/or daclizumab.

The dendrimer gen 3.5-glucosamine 6-sulfate has anti-inflammatory and anti-angiogenic properties. It is therefore useful as sole or as adjuvant therapy in rheumatoid arthritis and related conditions, Behcet's disease, inflammatory bowel disease, psoriasis, in the treatment of cancer metastases, rejection of organ transplants, and graft versus host disease. Alternatively, the dendrimer gen 3.5-glucosamine and the dendrimer gen 3.5-glucosamine 6-sulfate could be used in combination for the treatment of each of these disorders. The simultaneous administrations of dendrimer gen 3.5-glucosamine and dendrimer gen 3.5-glucosamine 6-sulfate offers considerable synergy of action with lower doses and less frequent administration being required and thereby reduce drug toxicity.

A further advantage of the glycodendrimers of the present invention is that they are large molecules. Tissue based sites of inflammation are more permeable to circulating molecules and cells than is healthy tissue, irrespective of what triggers the inflammatory response. Large molecules accumulate in areas of inflammation more rapidly that they do in normal tissue. The glycodendrimers of the present invention will therefore tend to accumulate at sites of inflammation.

The invention is further illustrated in the following examples.

A) CHEMISTRY AND TOXICITY

EXAMPLES A 1

Chemical Synthesis

Starburst PAMAM anionic dendrimers generation 2.5 and 3.5 (FIGS. 1a & b) synthesised by the divergent approach were used (Available from Dendritech Inc, Midland, ML USA or Sigma/Aldrich, Gillingham, Dorset, England, UK). D-glucosamine hydrochloride, D-glucosamine 6-sulfate hydrochloride, D-glucosamine 3,6-disulfate and D-glucosamine 3,4,6-trisulfate were used as the sodium salt. A known amount of the dendrimers (gen 1.5 or gen 2.5 or gen 3.5) stored as the sodium salt in methanol solution were evaporated under a nitrogen stream in order to obtain 1 mmol of dendrimer sodium salt. The dendrimers were then solubilised in double deionised water and the pH reduced with hydrochloric acid (HCl) in order to transform the surface groups from the non-reactive sodium carboxylated ($COO^-$ $Na^+$) to the reactive carboxylic acid (COOH). A known amount of glucosamine hydrochloride, glucosamine 6-sulfate, glucosamine 3,6-disulfate, or glucosamine 3,4,6-trisulfate was solubilised in double deionised water and the pH increased with triethylamine in order to obtain the reactive free base ($NH_2$). In the preparation of the dendrimer-glucosamine conjugates, the reaction was spiked with a known amount of $^{14}C$-glucosamine solution in double deionised water in order to follow the reaction and determine the amount of glucosamine attached to the dendrimers. The glucosamine and $^{14}C$-glucosamine aqueous solution or sulfated glucosamine solutions were then added to the dendrimer solution and an acid pH maintained with HCl. Subsequently, an excess of the condensing agent 1-ethyl-3-(3-dimethylaminopropyl)carbodiimide hydrochloride was solubilised in water and added to the reaction solution (FIG. 2). The reaction mixture was stirred at room temperature. Notably, the reaction can take place at ambient room temperature (i.e. <40° C.) and does not require the application of an external energy source.

Having prepared the dendrimer-glucosamine conjugates, some of the reaction mixture was passed through a PD-10 column and the fractions collected read on a β-counter to establish the presence of a high molecular weight conjugated compound. The reaction mixture was then purified in order to eliminate the unreacted glucosamine, the excess 1-ethyl-3-(3-dimethylaminopropyl)carbodiimide hydrochloride, and the urea formed during the reaction. In the case of dendrimers gen 3.5, the reaction mixture was dialysed against water and subsequently freeze-dried. In the case of the lower molecular weight generation dendrimers, the reaction mixture was freeze-dried, re-solubilised in deionised water and then passed through a Sephadex G15 column. The fractions at higher molecular weight containing the purified conjugate were collected, pooled together and freeze-dried.

After purification, a portion of the dendrimer-glucosamine conjugate was passed through a PD-10 column and the fractions collected read on a β-counter to monitor for the presence of unbound glucosamine. The total amount of glucosamine bound to the surface of the dendrimers was also determined using a β-counter. Characterisation and reproducibility of synthesis data for the dendrimer gen 3.5-glucosamine is shown in Table 1. In the case of the dendrimer-glucosamine sulfate conjugates, the amount of sulfated sugar attached to the polymer was determined by sulphur analysis: a known weight of the sample was combusted in an atmosphere of oxygen in a Schoniger oxygen flask. The products of combustion were washed into a 50 ml flask with double deionised water and made up to volume. This solution was analysed for sulphate content by ion chromatography using Dionex 100 ion chromatography. All of the prepared conjugates were also analysed by infrared spectroscopy. Characterisation and reproducibility of the synthesis data for the dendrimer gen 3.5-sulfated glucosamine constructs is shown in Table 2.

All of the conjugates were treated with activated carbon to remove endotoxin (i.e.: LPS) prior to their biological evaluation. Endotoxin could also be removed from the compounds synthesised using a column packed with polymixin B. The freeze-dried, purified, hygroscopic product was stored under airtight conditions. Endotoxin levels were determined using the *limulus amebocyte* lysate assay. All biological data was derived with batches of compounds whose endotoxin level was <0.1 EU/ml.

EXAMPLES A 2

Figure 3:
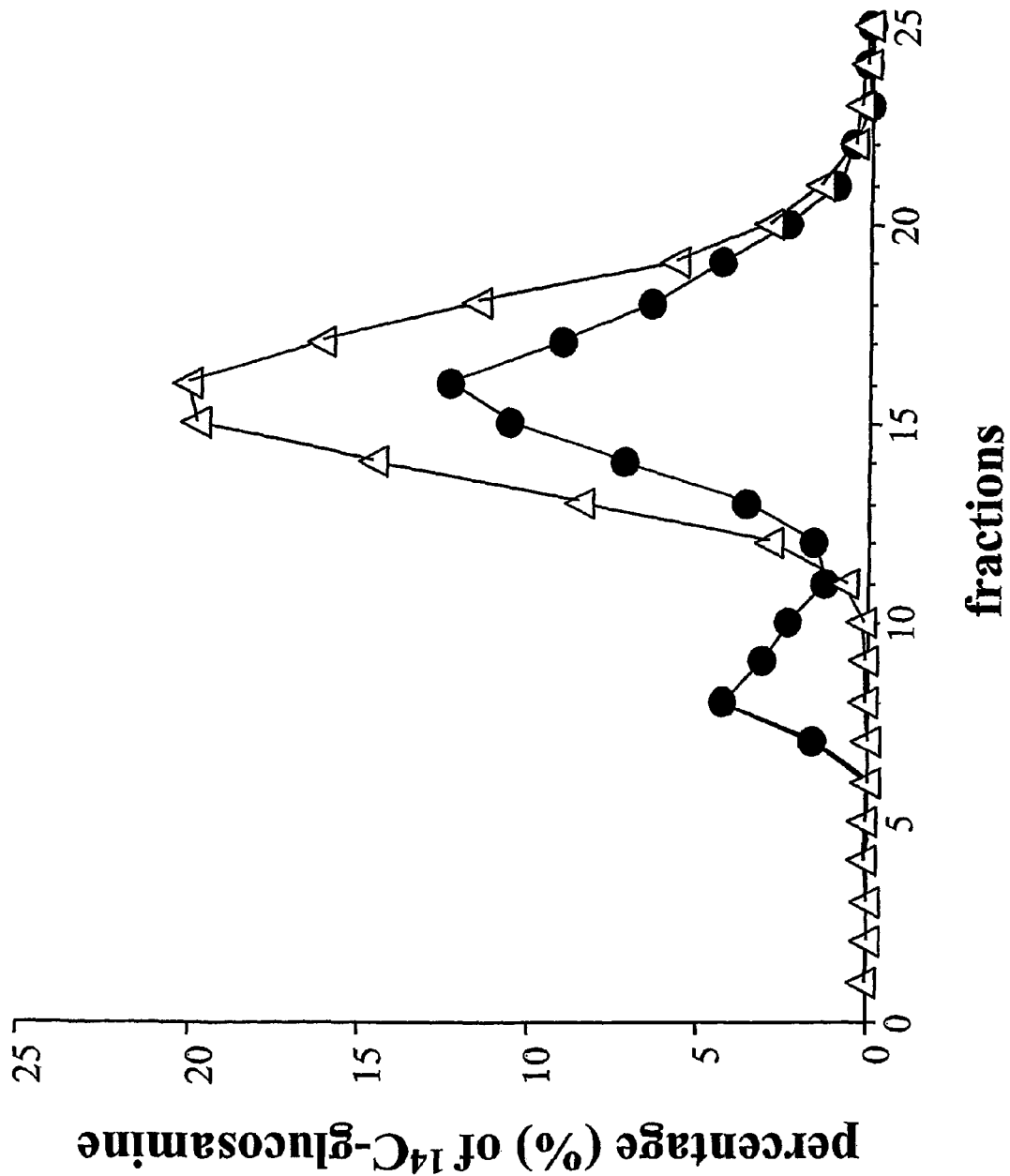
Figure 4:
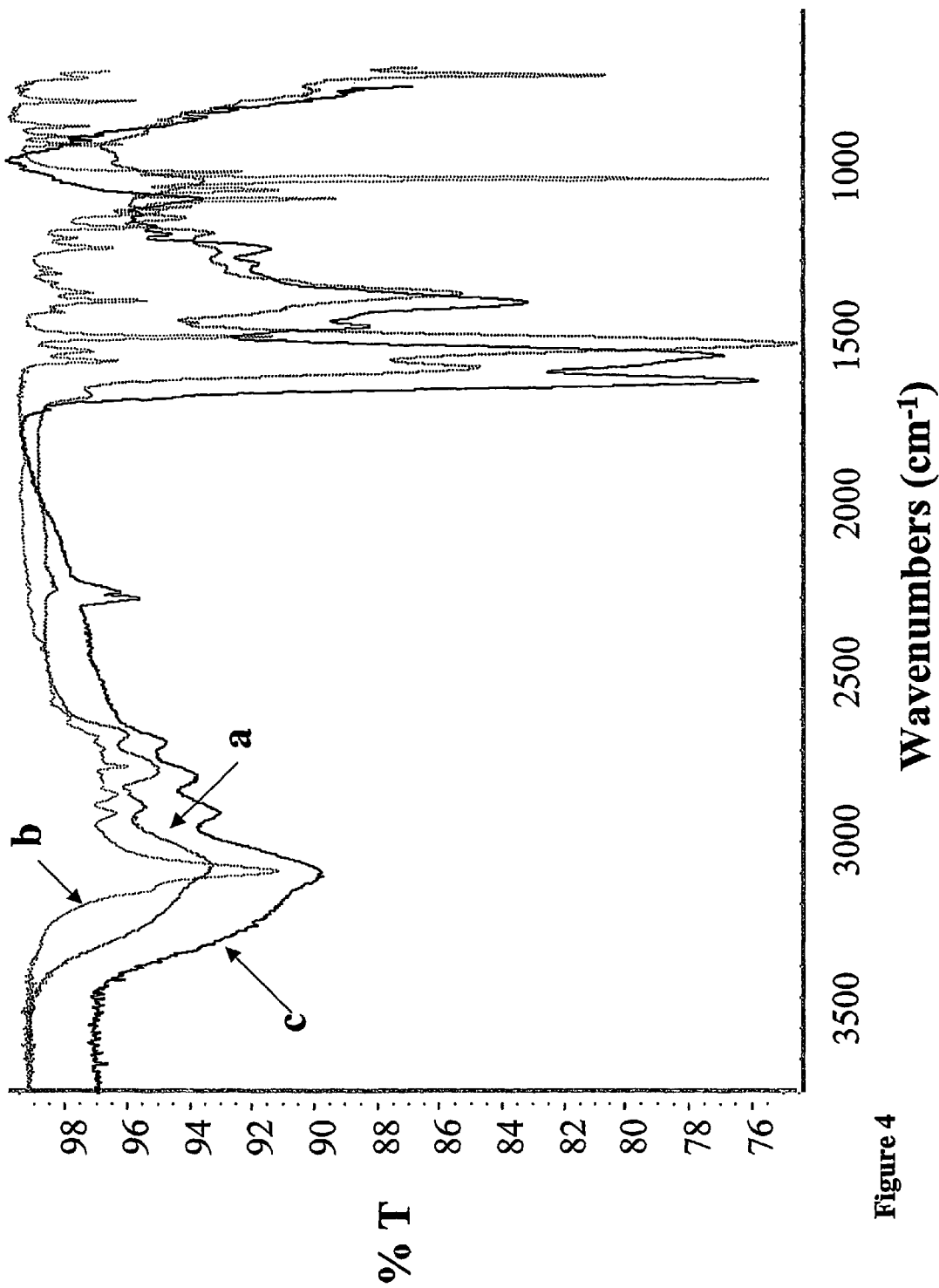
Figure 5:
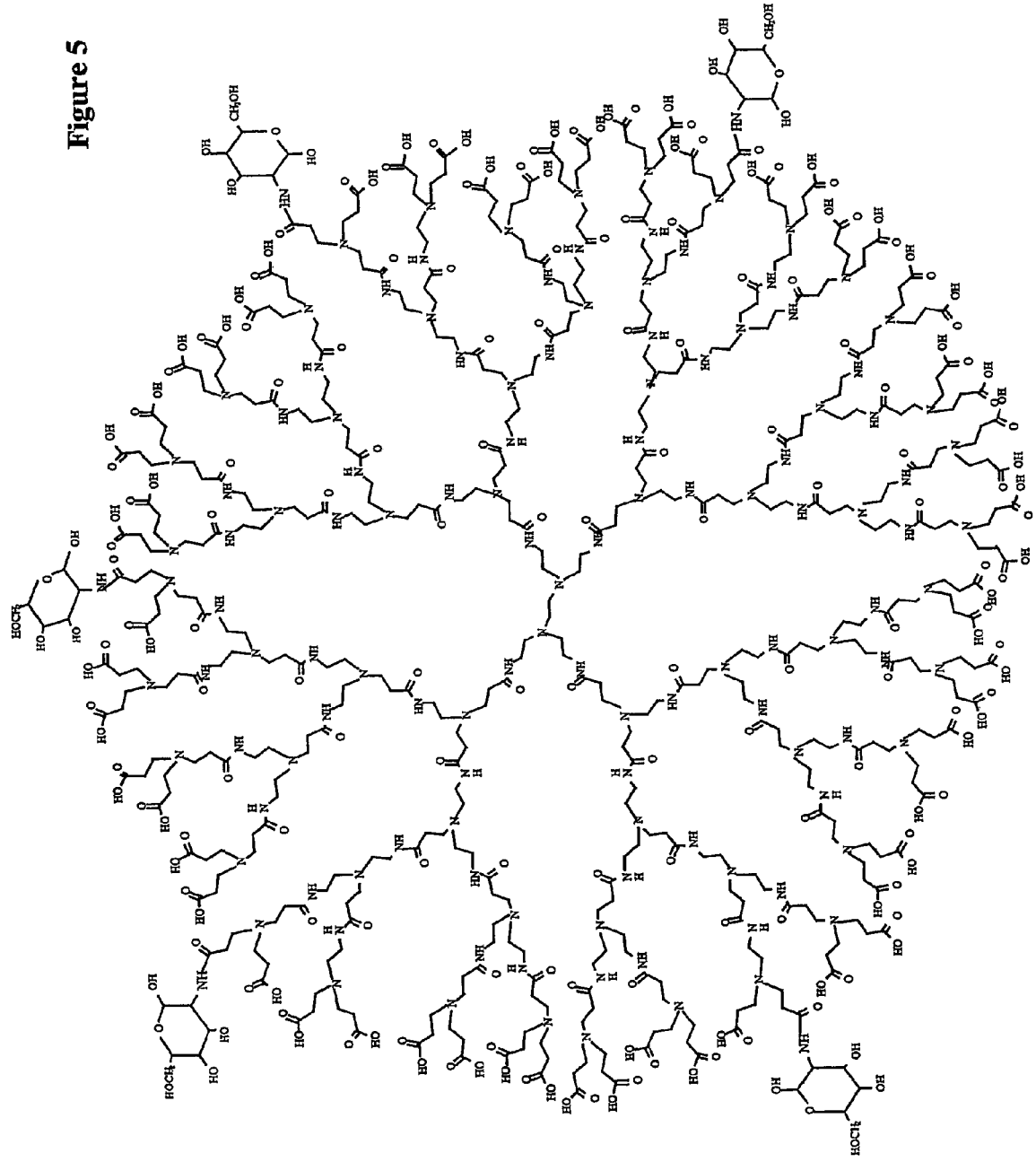

Chemical Characterisation of Dendrimer-Glucosamine and Dendrimer-sulfated Glucosamine Conjugates When glucosamine was conjugated to the dendrimers, the fractions collected by gel filtration (PD-10 column) of the reaction mixture and subsequently analysed at the β-counter showed a peak in fractions 7, 8, 9 & 10 collected (FIG. 3). This peak denotes the presence of a high molecular weight structure containing $^{14}C$-glucosamine confirming the formation of a dendrimer-glucosamine conjugate. FT-IR spectra peaks at 1640 $cm^{-1}$ and 1560 $cm^{-1}$, in conjugation with the peak at 3260 $cm^{-1}$ indicate the formation of the amide bond (FIG. 4 and FIG. 5). In the case of dendrimer-sulfated glucosamine conjugates, the further peak at 1210 $cm^{-1}$ (FIG. 6 for the dendrimer-glucosamine 6-sulfate conjugate) indicates the presence of sulfated glucosamine with prevention of loss of sulfuric acid during the conjugation.

The amount of glucosamine linked to the dendrimers, expressed as a percentage of converted carboxylic groups, ranged from 1.5 to 10.1%. In the case of the sulfated dendrimers, the sulphur content increased in the following order: monosulfated sugar (2.79% m:m S); disulfated sugar (5.78% m:m S); trisulfated sugar (7.93% m:m S). From the sulphur content, it was possible to calculate the amount of sulfate present in the conjugate as being 6% in the case of glucosamine 6-sulfate, 11% in the case of glucosamine 3,6-disulfate and 15% in the case of the glucosamine 3,4,6-trisulfate conjugate.

The one-step reaction was also investigated as a feasible method for the conjugation of:—a) PAMAM anionic dendrimers gen 2.5 to molecules containing aminic groups as well as to glucosamine 6-sulfate. The presence of characteristic peaks for the amide bond (3270 $cm^{-1}$, 1640 and 1550 $cm^{-1}$) indicated the formation of a conjugate between dendrimers and glucosamine or sulfated glucosamine as was seen with the generation 3.5 dendrimers.

Molecules described above, can be attached to the anionic PAMAM dendrimers using the same chemistry. This has been successfully achieved for 3-amino-1-propanesulfonic acid, 2-amino ethanesulfonic acid and aminomethane sulfonic acid as examples.

It is known that guest molecules can become trapped in the core of the dendrimer (Kempen H J M, Hoes C, van Boom J M, Spanjer H H, de Lange 3, Langendoen A & van Berkel T J C. (1984) A water-soluble cholesteryl-containing trisgalactoside—synthesis, properties, and use in directing lipid-containing particles to the liver. Journal Medicinal Chemistry 27, 1306-1312). Therefore it was important to determine the amount of unbound glucosamine inside the dendritic structure. This was undertaken by keeping a known amount of the conjugate in solution over a period of time and then determining the amount of unbound glucosamine present by gel filtration. FIG. 7(*i*) shows the gel filtration profiles of the conjugate stored in aqueous solution compared to free glucosamine; the amount of unbound glucosamine increased only slightly over time from 3.1 wt % at day 0 to 7.5 wt % after 90 days of storage at 4° C. Therefore, it was concluded that the covalent amide bond is stable and that there was no significant entrapment of free glucosamine within the dendrimer. Similar results were obtained from the dendrimer-glucosamine gen 2.5 after 30 days of storage under similar conditions (FIG. 7(ii)).

These observations allow a calculation of the number of molecules of glucosamine or sulfated glucosamine that have been linked to 1 molecule of dendrimer because all of the glucosamine or glucosamine sulfate molecules are linked to the outer surface of the dendrimer. The number of molecules of sulfated sugar linked to 1 molecule of dendrimer did not change with increasing numbers of sulfated groups attached to the glucosamine moiety, showing that the one-step reaction can be used as a standard method for conjugating sulfated glucosamine derivatives to dendrimers. The number of molecules of glucosamine or sulfated glucosamine linked to 1 molecule of dendrimer generation 2.5 is lower when compared to generation 3.5 because there are 32 carboxylic terminal groups in the former and 64 carboxylic acid groups in the latter. Therefore, due to the higher loading and the minimal toxicity of the generation 3.5 dendrimers, these conjugates were chosen as candidates for further biological investigation.

EXAMPLES A 3

Conjugation of Glucosamine to Dendrimer Gen 3.5 with DMSO as the Reaction Solvent A test tube was charged with PAMAM dendrimer gen 3.5 methanol solution and the solvent removed under a fast stream of nitrogen. The clear solid residue obtained was further dried in a vacuum oven for approximately 3 hours. The isolated solid was then dissolved in de-ionised water and the resulting solution acidified to approximately pH 3 using 0.1 N HCl. The solution was then purified/de-salted by dialysing against de-ionised water for 2 days (Visling dialysis tubing, Medicell International Ltd, MWCO 3500). Freeze-drying of the dialysed solution afforded the protonated dendrimer as a clear glassy solid.

The protonated dendrimer (150 mg), N-hydroxysuccinimide (9.6 mg), glucosamine hydrochloride (12.6 mg) and a magnetic stir bar were added to a 1.5 mL vial and the vial sealed with a septum-centred screw cap lid. A nitrogen atmosphere was then introduced into the vial, followed by anhydrous DMSO (0.7 mL) using a syringe. The resulting mixture was allowed to stir until a homogeneous solution had formed. Separately, 1,3-dicyclohexylcarbodiimide (17.1 mg) was dissolved in anhydrous DMSO (0.3 mL) under a nitrogen atmosphere in a 1.5 mL vial. A homogeneous solution was allowed to form which was then added by syringe to the stirred dendrimer reaction solution. The 1,3-dicyclohexylcarbodiimide vial was washed with fresh DMSO (0.1 mL) and this solution was also added to the dendrimer vial. After 15 min, triethylamine (12 μL) was added to the dendrimer solution by syringe and the resulting solution allowed to stir overnight at room temperature. To the reaction mixture was then added 1 N sodium hydroxide (800 μL). The resulting mixture was transferred to a larger vial, diluted with approximately 3 mL of de-ionised water and then filtered through a glass pipette with a piece of cotton-wool to act as a filter. The homogeneous supernatant was diluted to approximately 100 mL with de-ionised water and then dialysed against de-ionised water for 3 d (Visling dialysis tubing, Medicell International Ltd, MWCO 3500) followed by freeze-drying to afford a solid product.

In an alternative procedure, glucosamine hydrochloride (18.0 mg) was added with triethylamine (23 μL) in DMSO (0.2 mL) to a stirred dendrimer (150 mg) and N-hydroxysuccinimide (9.6 mg) solution in DMSO (0.7 mL) that had been activated with 1,3-dicyclohexylcarbodiimide (17.1 mg) for 1 h. This alternative procedure also afforded a solid product after dialysis and freeze-drying. Glucosamine conjugation to the dendrimer gen. 3.5 was conformed and quantified by proton nuclear magnetic resonance spectrometry in deuterium oxide. The mol % glucosamine conjugation was calculated to be 3.8±0.4.

EXAMPLES A 4

Toxicity of Compounds in Human Cell Lines

The compounds synthesised were evaluated for their toxicity in the following cell lines:—the human T-cell line (Sup-T1), a human T-cell line transformed with HTLV-1 (C8166), the human monocytic cell line (U937), the brain cell line transfected with human CD4 and the human chemokine receptor CCR5 (U87-CD4-CCR5), and the murine melanoma cell line (B16P10).

Dendrimers, glucosamine, glucosamine 6-sulfate and dendrimer conjugates were incubated with each cell line. Sup-T1, C8166, U937, U87-CD4-CCR5 and B16F10 cells were seeded at a density of $2\times10^5$ cell/ml and B16F10 cells were seeded at $1\times10^5$ cell/ml in 96 well microtiter plates in medium containing RPMI 1640, 20 mM L-glutamine, penicillin [250 IU/ml], streptomycin [250 μg/ml] and 10% fetal calf serum. The conjugates or controls were incubated for 67 h with the cells at concentrations ranging from 0-5,000 μg/ml. An MTT assay was then used to determine cell viability and the results were expressed as a percentage of that for cells grown in the absence of any compound.

Dextran and poly(L-lysine) were used as negative and positive controls respectively. Glucosamine and glucosamine 6-sulfate showed no toxicity at concentrations up to 1,000 μg/ml. Higher concentrations of these compounds could not be evaluated because glucosamine interferes with the MnT assay above his concentration. Dendrimers gen 3.5 and dendrimers gen 2.5 showed no toxicity up to concentrations of 5,000 μg/ml. The dendrimer gen 3.5-glucosamine conjugate showed $IC_{50}$ values ranging from 1,825 to 3,000 μg/ml in the different cell lines The dendrimer gen 3.5-glucosamine 6-sulfate conjugate had $IC_{50}$ values ranging from 246-307 μg/ml (Table 3).

EXAMPLES A 5

Toxicity of Compounds Against Primary Human Cells In Vitro

The dendrimers and the dendrimer conjugates were incubated with freshly isolated, human peripheral blood mononuclear (PBMN) cells and with freshly isolated human monocyte-derived-macrophages QDM).

Human PBMN cells and human MDMs were separated from buffy coat residues within 24 h of collection by density gradient centrifugation. The cells were then washed with phosphate-buffered saline (PBS), re-suspended in lymphocyte growth medium (RPMI 1640, 20 mM L-glutamine, penicillin [250 IU/ml], streptomycin [250 μg/1 ml] and 15% foetal calf serum) containing human recombinant interleukin 2 (IL2, 20 IU/ml) for 3 days and then plated in a 96 well plate at a density of $1\times10^6$ cells/ml. To separate MDMs, the remaining cells were re-suspended in macrophage-growth medium (RPMI 1640, 20 mM L-glutamine, penicillin [250 IU/ml], streptomycin [250 μg/ml] and 10% human serum) and plated in a plastic dish for 2 h. MDMs were then scraped, washed and plated in a 96 well plate at a density of $1\times10^6$ cells/ml. The monocytes were allowed to differentiate to MDMs by a further 3 days of adherence. The compounds were then added to PBMN cells or to MDMs ($1\times10^6$ cells/ml) and incubated for 67 h. Cell viability was assessed using the MTT assay at 72 h.

Dendrimer gen 3.5 and glucosamine 6-sulfate were not toxic to PBMN cells or to MDMs up to the maximum concentration of 1,000 µg/ml that was evaluated. The $IC_{50}$ value for dendrimer gen 3.5-glucosamine was 340-360 µg/ml in primary cells as determined using an MTT assay. The $IC_{50}$ value for the dendrimer gen 3.5-glucosamine 6-sulfate construct, the dendrimer gen 3.5-glucosamine 3,6-disulfate construct, and the dendrimer gen 3.5-glucosamine 3,4,6-trisulfate conjugate was 230-260 µg/ml in primary cells as determined using an MTT assay.

EXAMPLES A 6

The Effect of the Dendrimer Gen 3.5-Glucosamine and the Dendrimer Gen 3.5 Sulfated Glucosamine Conjugates on the Release of MIP-1β from Single Donor, Human PBMN Cells, MDMs and Peritoneal Macrophages Recent studies have shown that macrophage inflammatory protein-1β (MIP-1β) is the earliest pro-inflammatory chemokine that is released by cells of macrophage origin after they have been exposed to an inflammatory stimulus (Wang Z-M, Liu C & Dziarski R. Chemokines are the main pro-inflammatory mediators in human monocytes activated by *Staphylococcus aureus*, peptidoglycan, and endotoxin. (2000) J. Biological Chemistry 275; 20260-20267). All the polymers that have been studied to date, irrespective of whether they have been derived from a natural source or have been synthetically made have shown a significant ability to induce the release of pro-inflammatory cytokines and chemokines from immune cells. We therefore exposed single donor human PBMN cells, single donor human MDMs, and single donor human peritoneal macrophages to the compounds synthesised in, order to determine whether they induced any pro-inflammatory responses from these cells.

Cells were isolated as previously described within 4 hours of collection and then plated at $1\times10^6$ cells/ml. Dendrimer gen 3.5, dendrimer gen 3.5 glucosamine, dendrimer gen 3.5-glucosamine 6-sulfate, dendrimer gen 3.5-glucosamine 3,6-disulfate, and dendrimer gen 3.5-glucosamine 3,4,6-trisulfate were then added to the cells at a concentration of 50 to 200 µg/ml. Cell free culture supernatants were harvested 36 h later and assayed for MIP-1β.

Figure 11I:
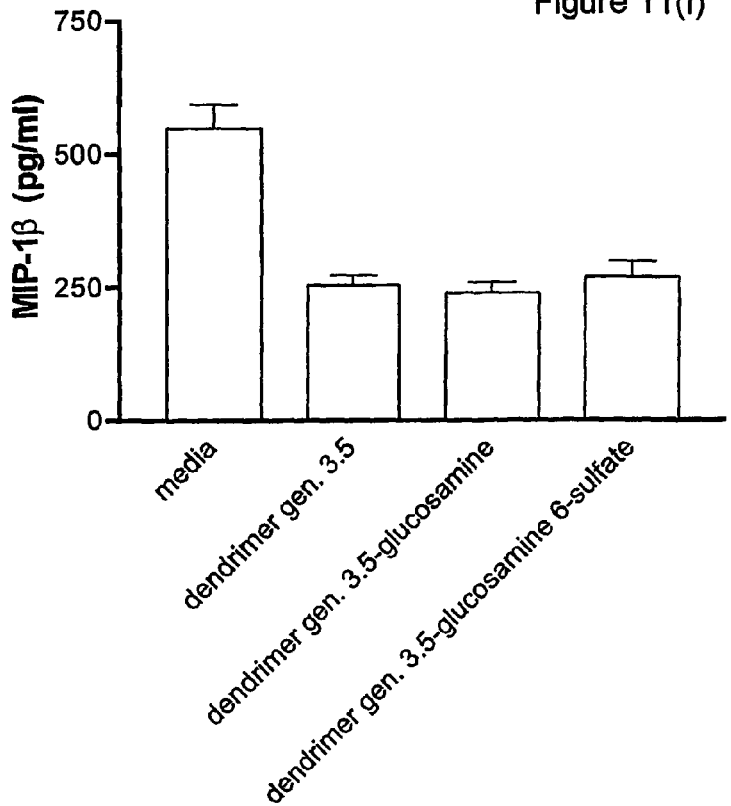
Figure 11:
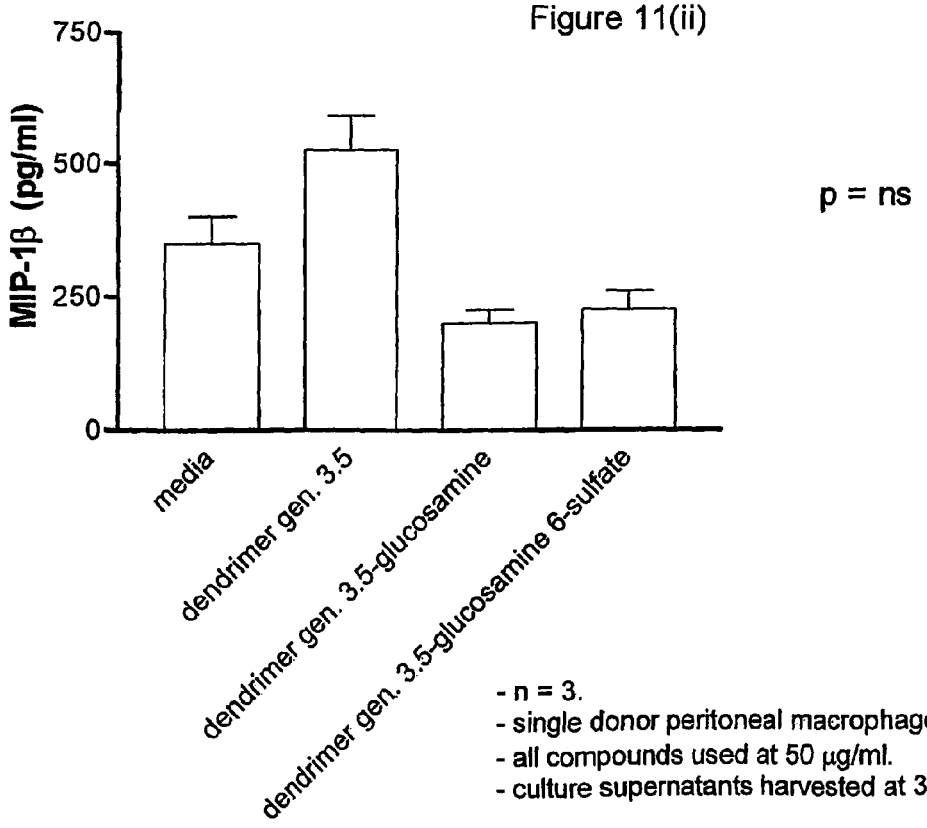

No release of MIP-1β above that seen in the control wells occurred with:
a) PBMN cells and dendrimer gen 3.5, dendrimer gen 3.5 glucosamine, or dendrimer gen 3.5-glucosamine 6-sulfate at 50 µg/ml (FIG. 8(*i*)).
b) MDMs and dendrimer gen 3.5, dendrimer gen 3.5 glucosamine, or dendrimer gen 3.5-glucosamine 6-sulfate at 50 µg/ml (FIG. 8(*ii*) and FIG. 8(*iii*)).
c) MDMs and dendrimer gen 3.5-glucosamine 3,6-disulfate, and dendrimer gen 3.5-glucosamine 3,4,6-trisulfate at 50 µg/ml (FIG. 9).
d) Peritoneal macrophages after 36 h (FIG. 10(*i*) and FIG. 10(*ii*)) and after 72 h (FIG. 10(*iii*)) of culture with dendrimer gen 3.5, dendrimer gen 3.5 glucosamine, or dendrimer gen 3.5-glucosamine 6-sulfate with each molecule at 25 µg/ml.
e) Peritoneal macrophages after 36 h of culture with dendrimer gen 3.5, dendrimer gen 3.5 glucosamine or dendrimer gen 3.5-glucosamine 6-sulfate with each molecule at 50 µg/ml (FIG. 11(*i*) and FIG. 11(*ii*) respectively).
f) Peritoneal macrophages after 36 h of culture with dendrimer gen 3.5-glucosamine 3,6-disulfate or dendrimer gen 3.5-glucosamine 3,4,6-trisulfate with each molecule at 50 µg/ml (FIG. 12(*i*) and FIG. 12(*ii*) respectively).
g) Peritoneal macrophages after 36 h of culture with dendrimer gen 3.5-glucosamine 3,6-disulfate or dendrimer gen 3.5-glucosamine 3,4,6-trisulfate with each molecule at 100 µg/ml (FIG. 13(*i*) and FIG. 13(*ii*)) and at 200 µg/ml (FIG. 13(*iii*) and FIG. 13(*iv*)).

Therefore, in conclusion, it is important to note that dendrimer gen 3.5-glucosamine, dendrimer gen 3.5-glucosamine 6-sulfate, dendrimer gen 3.5-glucosamine 3,6-disulfate, and dendrimer gen 3.5-glucosamine 3,4,6-trisulfate did not affect the release of chemolines or cytokines from immune cells (ie: primary human peripheral blood mononuclear cells, human monocyte derived macrophages or human peritoneal macrophages) that were in their normal resting state. This is the first time that a glycodendrimer has been shown not to affect human primary cells in their normal resting state. Therefore when administered as a medicine, these molecules will only have a drug mediated effect on diseased human cells. These two compounds will not interfere with the routine homeostatic control under which normal human cells operate on a day-to-day basis.

EXAMPLES B

Experiments with Lipopolysacclaride (LPS)

The Effect of the Dendrimer gen 3.5-glucosamine Conjugate on the Release of Chemokines and, in Turn, Cytokines by LPS from Single Donor Human PBMN Cells PBMN cells were isolated from fresh blood from single donors by density gradient centrifugation. The cells were re-suspended in growth medium (RPMI 1640, 20 mM L-glutamine, penicillin [250 IU/ml], streptomycin [250 µg/ml] and 10% endotoxin free human serum) and the cell density adjusted to $2\times10^6$ cells/ml. Aliquots of the cell suspension were transferred to a 12-well tissue culture plate and incubated for 15 min at 37° C. To these PBMN cells, LPS was added (usually at 5 ng/ml) either before or after the addition of the endotoxin free dendrimer gen 3.5-glucosamine. In the first set of experiments, the LPS (*Salmonella minnesota*, Sigma. Catalogue number L9764) was added min to 24 h after the dendrimer gen 3.5-glucosamine conjugate. In the second set of experiments, the LPS was added 30 min, 1 h, 2 h, 3 h or 4 h before the dendrimer gen 3.5-glucosamine. The concentration of dendrimer gen 3.5-glucosamine added was 150-200 µg/ml. The cells were then maintained at 37° C. with 5% $CO_2$. Cell free supernatants were collected at regular time points up to a maximum of 96 h later and assayed for macrophage inflammatory protein-1α (MIP-1α), macrophage inflammatory protein-1β (MIP-1β), Interleukin-8 (IL8), Tumor Necrosis Factor-α (TNF-α), Interleukin-1β (IL-1β) and Interleukin-6 (IL-6).

Figure 14I:
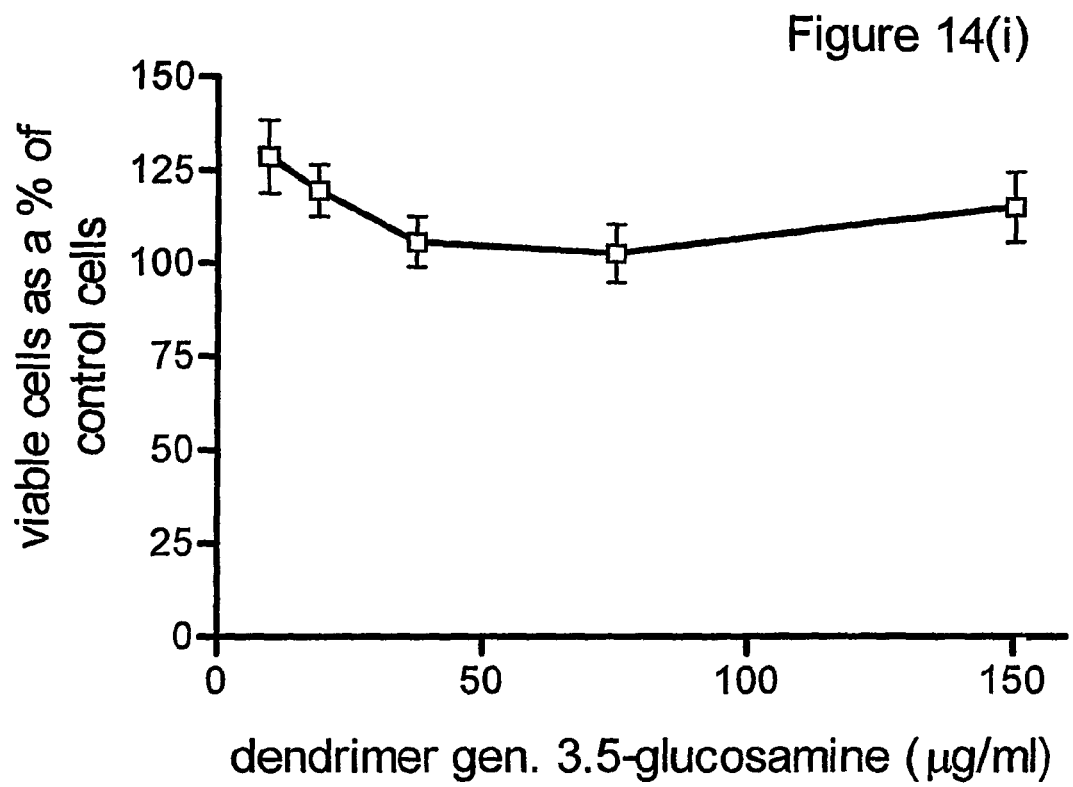
Figure 14:
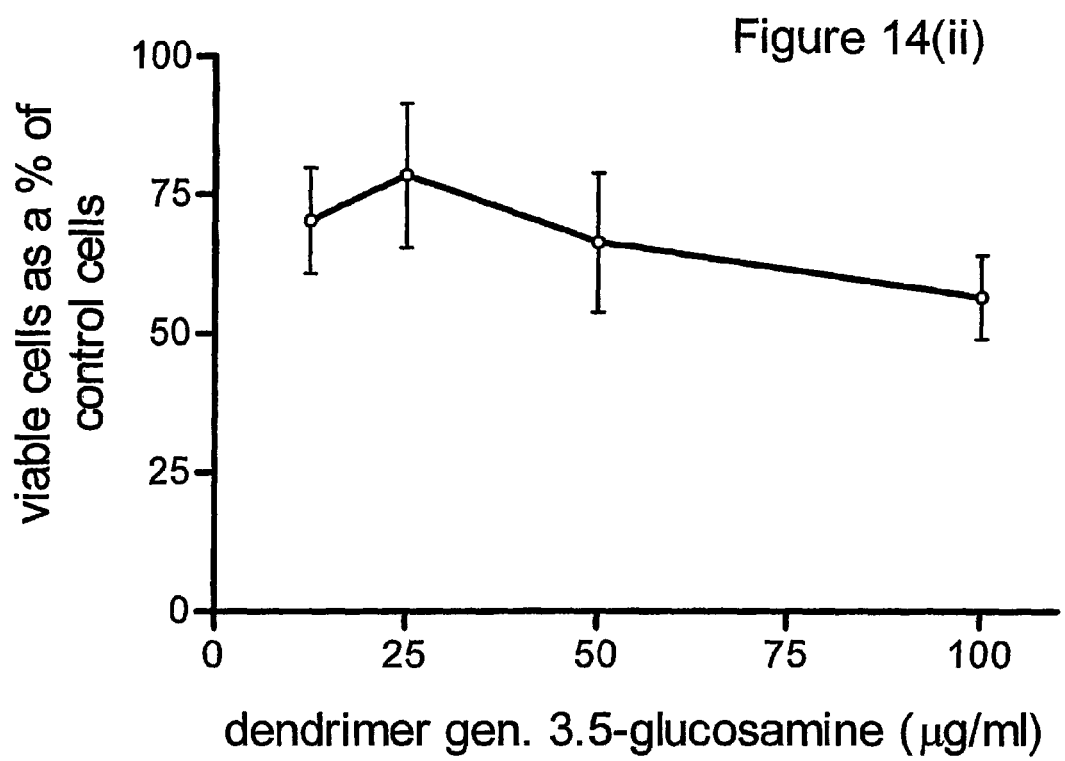

Experiment B 1: Single donor MDMs were prepared as described and cultured with dendrimer gen 3.5-glucosamine up to a concentration of 150 µg/ml for 72 h. No reduction in cell viability was seen when compared to MDMs cultured in media alone over a period of 72 h (FIG. 14(*i*)).

Single donor, human umbilical vein endothelial cells (HU-VECs) were also prepared as follows. Umbilical cords were obtained from placentas from the maternity wards of Hamnmersmith and Queen Charlotte's Hospitals within 4 h of delivery. Excess blood was removed from the cord by massaging the outside. The cord was then sprayed with 70% alcohol and wiped. The ends were cut with sharp scissors and the umbilical vein identified. 14 gauge cannulas with luer lock ends were inserted into each end of the umbilical vein and tied in place. The vein was then flushed through with HBSS (Sigma, Poole, Dorset) using a 20 ml syringe attached to a cannula. Endothelial cells were dislodged from the vein using a solution of 20 mg/ml collagenase A (Sigma) in BBSS (20 ml) and filter sterilised using a 20 μm membrane. Using a second 20 ml syringe, this solution was introduced into the umbilical vein and carefullly agitated by gently applying pressure to each syringe in turn. The cord was then incubated in a water bath at 37° C. for 20 min with a second agitation for 10 min. The collagenase A solution was removed from the cord and added to 20 ml of media containing 20% FCS to quench the enzyme and a further 20 ml of media flushed through the vein to remove any remaining endothelial cells. Cells were pelleted by centrifugation (400 g/5 min), resuspended in 5 ml growth media [WM alpha (Sigma)] containing 20% FCS, L-glutamine (2 mM), 200 IU/ml penicillin, 200 μg/ml streptomycin and 50 μg/ml clinical grade heparin (Leo Laboratories, Bucks). They were then transferred to collagen coated 25 $cm^2$ tissue culture flasks and incubated at 37° C. with 5% $CO_2$. After 48 h incubation, 5 μg/ml endothelial cell growth supplement (ECGS-Sigma) was added.

Cultures were examined daily using an inverted microscope. When confluent, growth medium was aspirated and replaced with an equal volume of HBSS at 37° C. Cells were then removed by trypsinisation. The HBSS was aspirated and replaced with 2 ml trypsin (0.5 mg/ml)/EDTA (0.2 mg/ml) solution in HBSS Wife Technologies, Paisley, UK) and incubated at 37° C. for 5-10 min until all cells had been removed from the bottom of the flask. Cells were then split to a ratio of 1:2 to 1:3 with fresh growth media containing ECGS (5 μg/ml) and transferred to the appropriate flask or tissue culture plate depending upon the assay being performed.

The HUVECs were cultured with dendrimer gen 3.5-glucosamine up to a concentration of 100 μg/ml for 72 h. No reduction in cell viability was seen when compared to HUVECs cultured in media alone over a period of 72 h (FIG. 14(ii)).

Experiment B 2: Single donor PBMN cells were isolated and resuspended in RPMI, L-glutamine, penicillin, streptomycin and 10% human serum at a density of $1\times10^6$ cells/ml.

Figure 15:
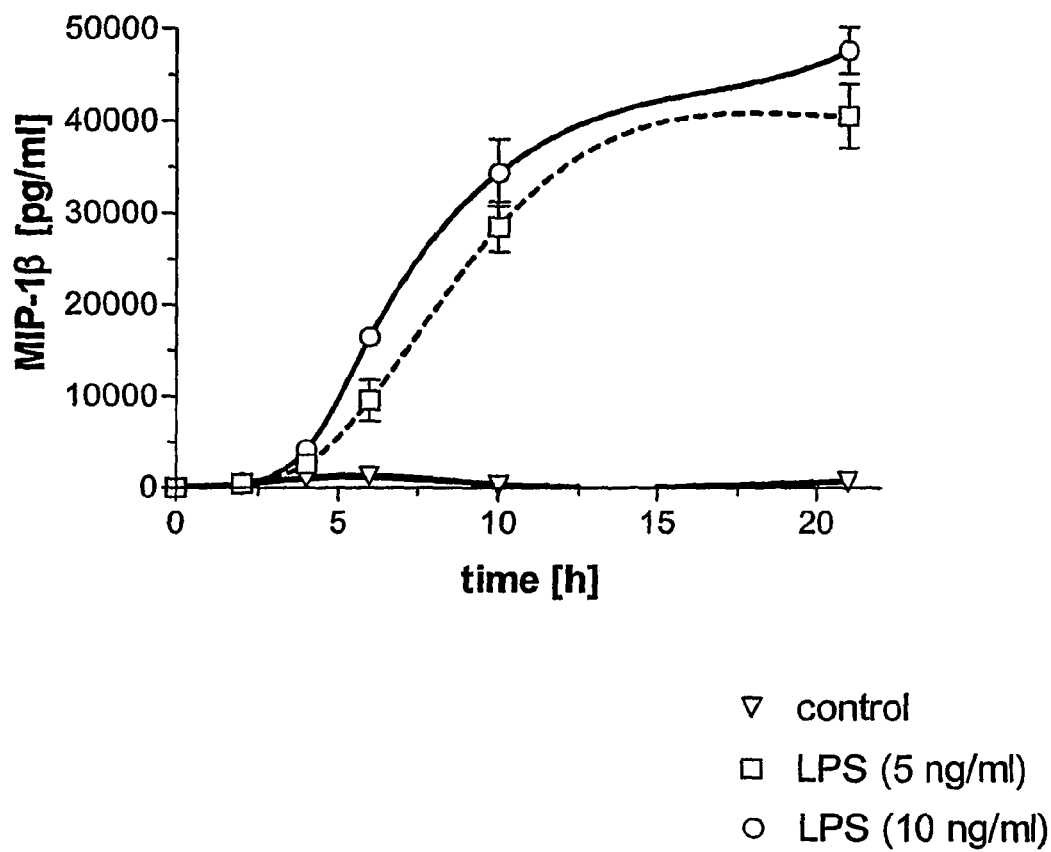

The cells were then plated (1 ml) in 12 well tissue culture plates and then cultured for 15 min at 37° C. in 5% $CO_2$. LPS was then added at 5 ng/ml. Cell free culture supernatants were harvested at regular intervals for up to 21 h and assayed for MIP-1β as shown in FIG. 15.

Experiment B 3: Single donor PBMN cells were isolated from one individual, resuspended in RPMI, L-glutamine, penicillin, streptomycin and 10% human serum at a density of $1\times10^6$ cells/ml. The cells were then plated (1 ml) in 12 well tissue culture plates and cultured for min at 37° C. in 5% $CO_2$. Dendrimer gen 3.5-glucosamine was then added at 100 μg/ml. The cells were cultured for 30 min at 37° C. in 5% $CO_2$ and LPS was then added at 5 ng/ml. Cell free culture supernatants were harvested 21 h later and assayed for MIP-1β as shown in FIG. 16(i). A significant reduction in MIP-1β release was seen when dendrimer gen 3.5-glucosamine was present.

It has been confirmed that dendrimer gen 3.5-glucosamine and dendrimer gen 3.5-glucosamine 6-sulfate are not mediating their activity by binding to the endotoxin used in these experiments.

Experiment B 4: Single donor PBMN cells were isolated and resuspended in RPMI, L-glutamine, penicillin, streptomycin and 10% human serum at a density of $1\times10^6$ cells/ml. The cells were then plated (1 ml) in 12 well tissue culture plates and cultured for 15 min at 37° C. in 5% $CO_2$. Dendrimer gen 3.5-glucosamine was then added at 100 μg/ml. The cells were cultured for 1 hour at 37° C. in 5% $CO_2$ and LPS was then added at 5 ng/ml. Cell free culture supernatants were harvested 21 h later and assayed for MIP-1β as shown in FIG. 16(ii). A significant reduction in MIP-1β, release was seen when dendrimer gen 3.5-glucosamine was present.

Experiment B 5: Single donor PBMN cells were isolated and resuspended in RPMI, L-glutamine, penicillin, streptomycin and 10% human serum at a density of $1\times10^6$ cells/ml. The cells were then plated (1 ml) in 12 well tissue culture plates and cultured for 15 min at 37° C. in 5% $CO_2$. Dendrimer gen 3.5-glucosamine was then added at 100 iug/ml. The cells were cultured for 24 hours at 37° C. in 5% $CO_2$ and LPS was then added at 5 ng/ml. Cell free culture supernatants were harvested 21 h later and assayed for MIP-1β as shown in FIG. 16(iii). A significant reduction in MIP-1β release was seen when dendrimer gen 3.5-glucosamine was present.

Experiment B 6: Single donor PBMN cells were isolated and resuspended in RPMI, L-glutamine, penicillin, streptomycin and 10% human serum at a density of $1\times10^6$ cells/ml. The cells were then plated (1 ml) in 12 well tissue culture plates and cultured for 15 min at 37° C. in 5% $CO_2$. Dendrimer gen 3.5-glucosamine was then added at 100 ag/mnl. The cells were cultured for periods ranging from 30 minutes to 24 hours at 37° C. in 5% $CO_2$ and LPS was then added at 5 ng/ml. Cell free culture supernatants were harvested 21 h later and assayed for MIP-1β as shown in FIG. 16(iv). A significant reduction in MIP-1β release was seen when dendrimer gen 3.5-glucosamine was present at all time points studied.

Figure 17:
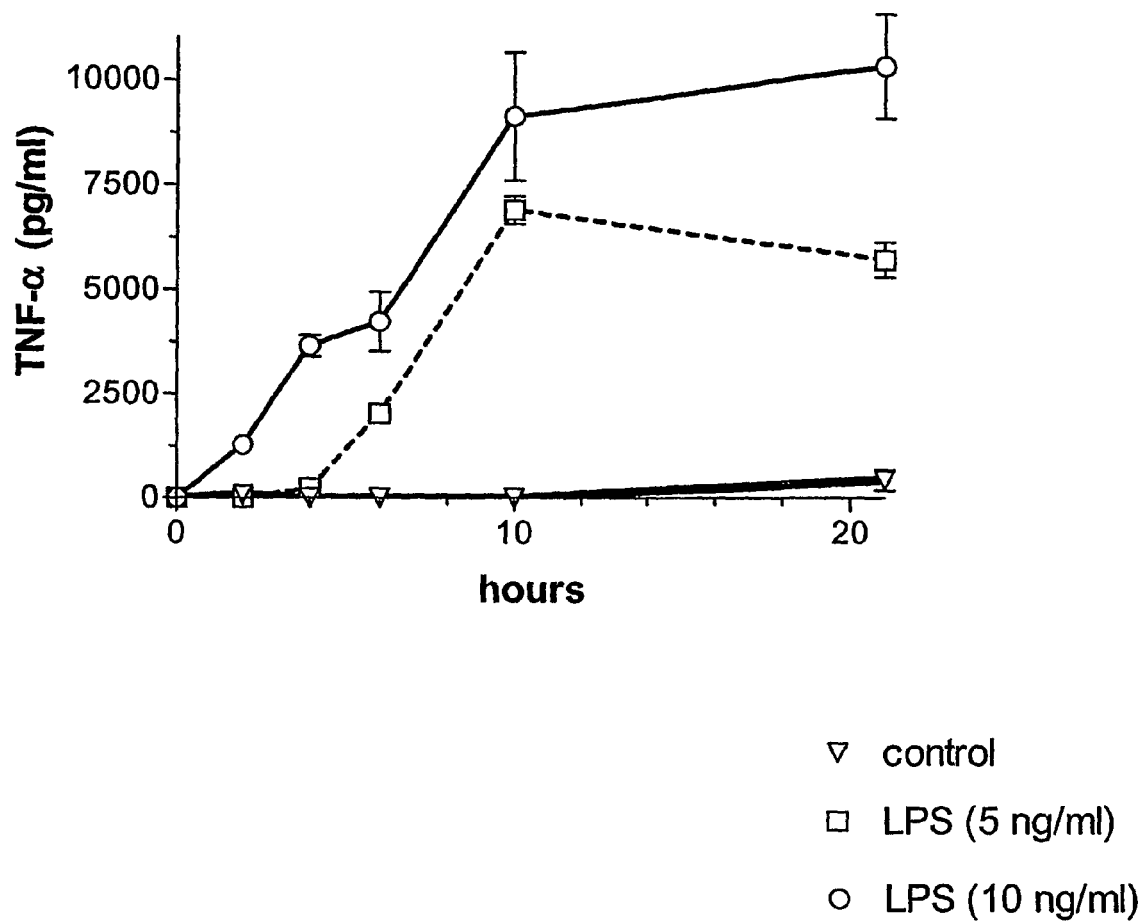

Experiment B 7: Single donor PBMN cells were isolated and resuspended in RPMI, L-glutamine, penicillin, streptomycin and 10% human serum at a density of $1\times10^6$ cells/ml. The cells were plated (1 ml) in 12 well tissue culture plates and then cultured for 15 min at 37° C. in 5% $CO_2$. LPS was then added at 5 ng/ml. Cell free culture supernatants were harvested at regular intervals for up to 21 h and assayed for TNF-α as shown in FIG. 17.

Figure 18:
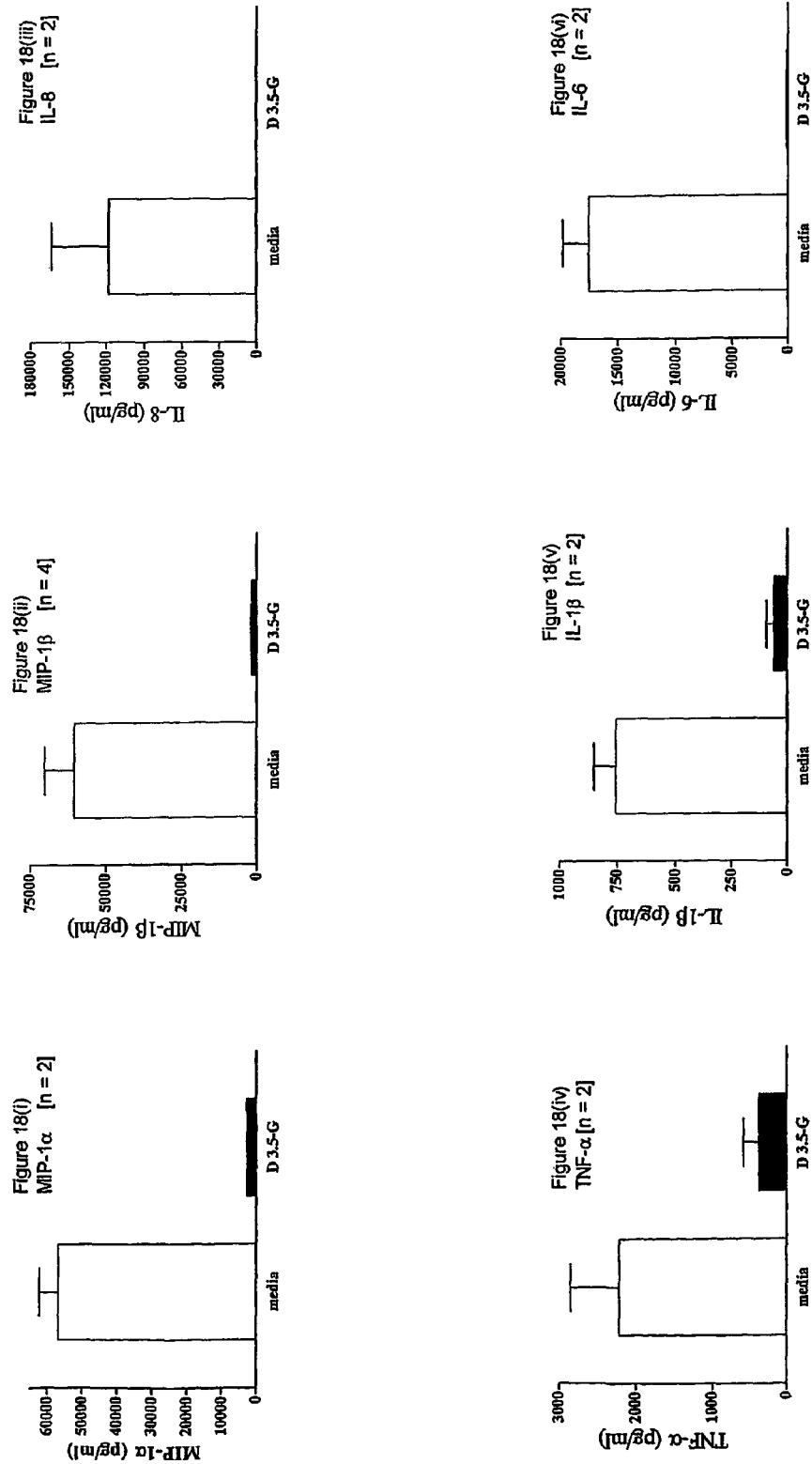

Experiment B 8: Single donor PBMN cells were isolated and resuspended in RPMI, L-glutamine, penicillin, streptomycin and 10% human serum at a density of $1\times10^6$ cells/ml. The cells were then plated (1 ml) in 12 well tissue culture plates and cultured for 15 min at 37° C. in 5% $CO_2$. Dendrimer gen 3.5-glucosamine was then added at 100 μg/ml. The cells were cultured for 30 min at 37° C. in 5% $CO_2$ and LPS was then added at 5 ng/ml. Cell free culture supernatants were harvested 21 h later and assayed for MIP-1β as shown in FIG. 18(i), MIP-1β as shown in FIG. 18(ii), IL-8 as shown in FIG. 18(iii), TNF-α as shown in FIG. 18(iv), IL 1β as shown in FIG. 18(v), and IL6 as shown in FIG. 18(vi). For all of the chemokines and pro-inflammatory cytokines studied, a significant reduction in their release was seen when dendrimer gen 3.5-glucosamine was present.

Figure 19:
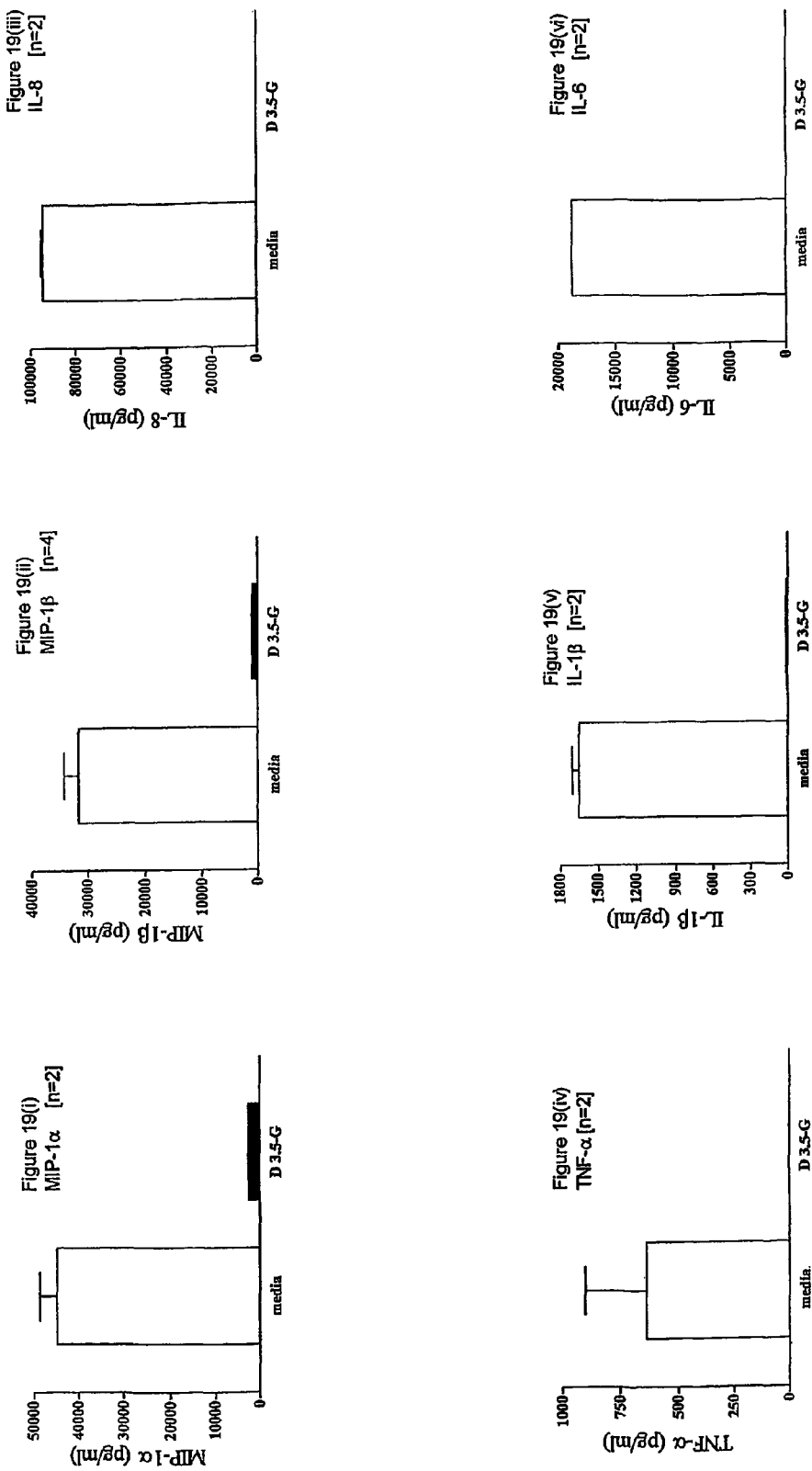

Experiment B 9: Single donor PBMN cells were isolated and resuspended in RPMI, L-glutamine, penicillin, streptomycin and 10% human serum at a density of $1\times10^6$ cells/ml. The cells were then plated (1 ml) in 12 well tissue culture plates and cultured for 15 min at 37° C. in 5% $CO_2$. Dendrimer gen 3.5-glucosamine was then added at 200 μg/ml. The cells were cultured for 30 min at 37° C. in 5% $CO_2$ and LPS was then added at 5 ng/ml. Cell free culture supernatants were harvested 21 h later and assayed for MIP-1α as shown in FIG. 19(i), MIP-1β as shown in FIG. 19(ii), IL8 as shown in FIG. 19(iii), TNF-α as shown in FIG. 19(iv), IL-1β as shown in FIG. 19(v), and IL6 as shown in FIG. 19(vi). For all of the chemokines and pro-inflammatory cytokines studied, a significant reduction in heir release was seen when dendrimer gen 3.5-glucosamine was present.

Also tested was a dendrimer gen 3.5 construct that had been made in aqueous solution by reacting the dendrimer gen 3.5 with the EDC linker but then omitting the addition of glucosamine or glucosamine sulphate. This dendrimer gen 3.5-EDC construct did not reduce the release of chemokines (MIP-1β) or TNF-α from peripheral blood mononuclear cells when they were challenged with lipopolysaccharide at 5 ng/ml. This means that the reduction in chemokine and cytokine release that was seen with the dendrimer-glucosamine construct was not due to side reactions of the dendrimer itself with the EDC linker group.

In further experiments, the dendrimer gen 3.5 that was conjugated to glucosamine using DMSO as the reaction solvent was also evaluated. This dendrimer gen 3.5-glucosamine construct did not reduce the release of chemokines (MW-1β) or cytokines (TNF-α) from peripheral blood mononuclear cells when they were challenged with lipopolysaccharide at 5 ng/ml. Therefore, the synthesis of the dendrimer gen 3.5-glucosamine in an aqueous solution was an important component of the process for making biologically active molecules.

Figure 20:
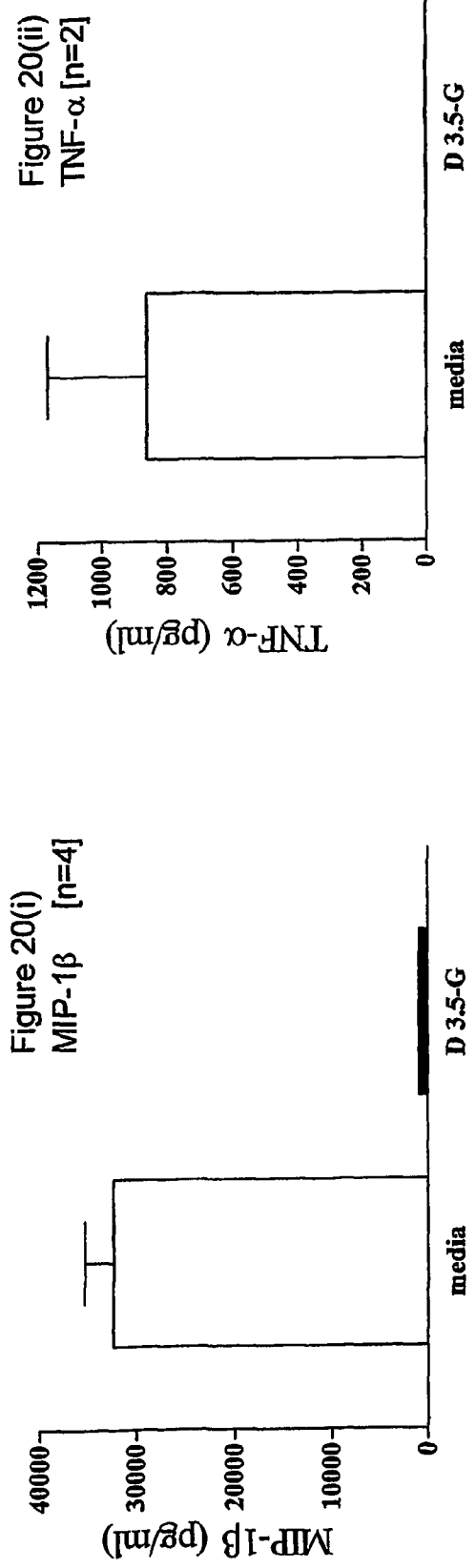

Experiment B 10: Single donor PBMN cells were isolated and resuspended in RPMI, L-glutamine, penicillin, streptomycin and 10% human serum at a density of $1 \times 10^6$ cells/ml. The cells were then plated (1 ml) in 12 well tissue culture plates and cultured for 15 min at 37° C. in 5% $CO_2$. Dendrimer gen 3.5-glucosamine was then added at 200 μg/ml. The cells were cultured for 1 hour at 37° C. in 5% $CO_2$ and LPS was then added at 5 ng/ml. Cell free culture supernatants were harvested 21 h later and assayed for MIP-1β as shown in FIG. 20(i) and TNF-α as shown in FIG. 20(ii). For all of the chemokines and pro-inflammatory cytokines studied, a significant reduction in their release was seen when dendrimer gen 3.5-glucosamine was present.

Figure 21V:
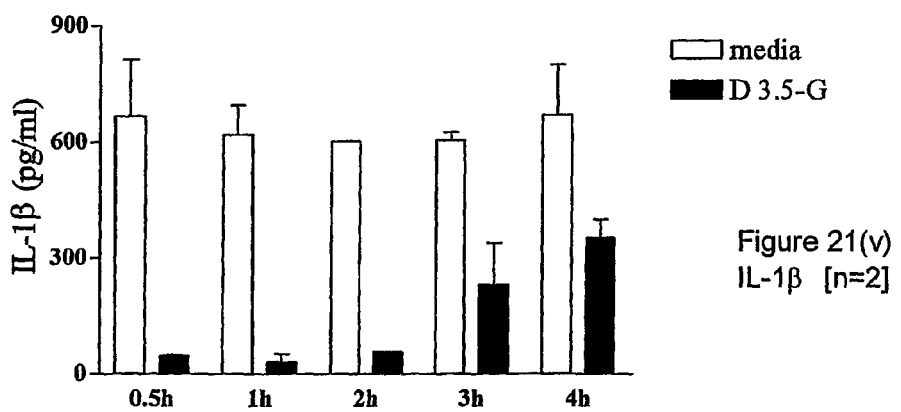
Figure 21:
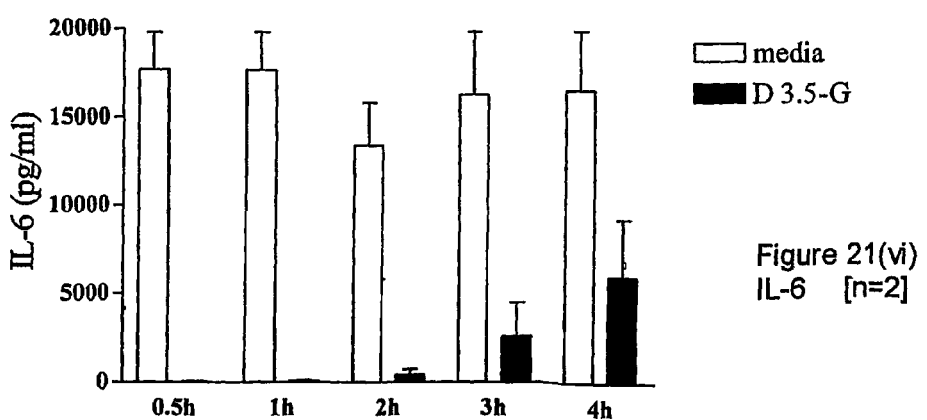

Experiment B 11: Single donor PBMN cells were isolated and resuspended in RPMI, L glutamine, penicillin, streptomycin and 10% human serum at a density of $1 \times 10^6$ cells/ml. The cells were then plated (1 ml) in 12 well tissue culture plates and cultured for 15 min at 7° C. in 5% $CO_2$. LPS was then added at 5 ng/ml and the cells were cultured for 30 min, or 1 our, or 2 hours, or 3 hours, or 4 hours at 37° C. in 5% $CO_2$ before adding dendrimer gen 3.5-lucosamine at 100 μg/ml. Cell free culture supernatants were harvested 21 h after the addition of the LPS and assayed for MIP-1α as shown in FIG. 21(i), MIP 1β as shown in FIG. 21(ii), IL8 as shown in FIG. 21(iii), TNF-α as shown in FIG. 21(iv), IL1 as shown in FIG. 21(v), and IL-6 as shown in FIG. 21(vi). For all of the chemokines and pro-inflammatory cytokines studied, a significant reduction in their release was seen when dendrimer gen 3.5-glucosamine was present.

Figure 22I:
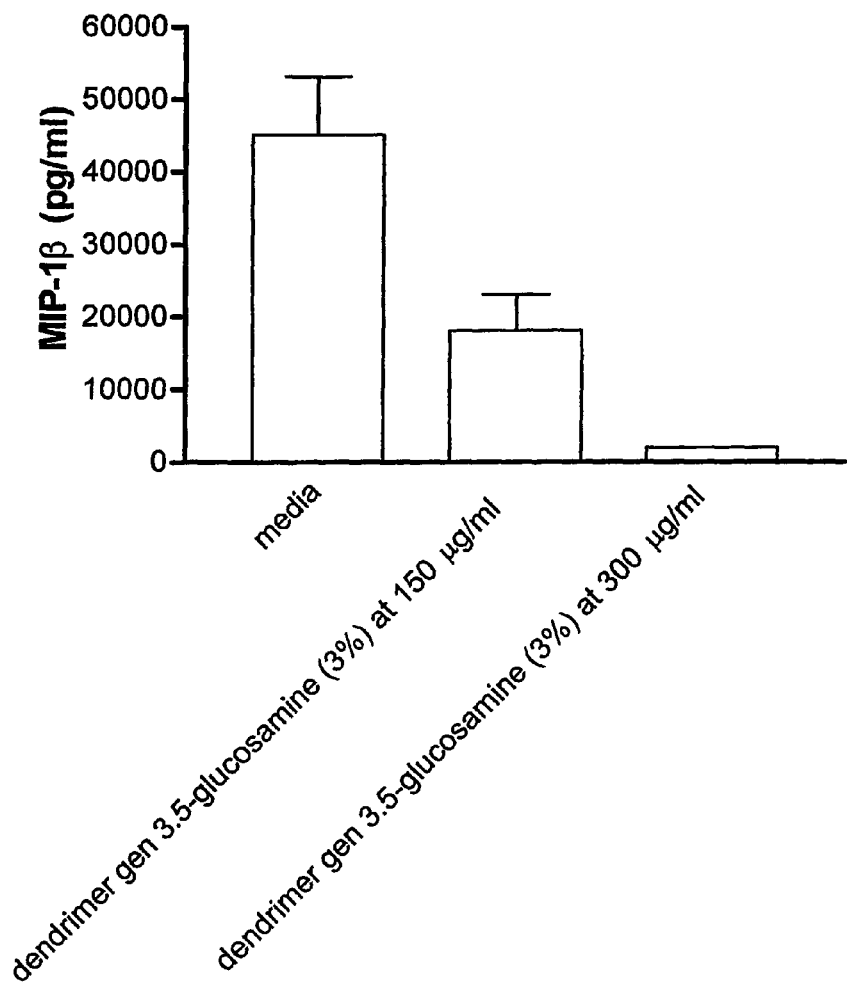
Figure 22:
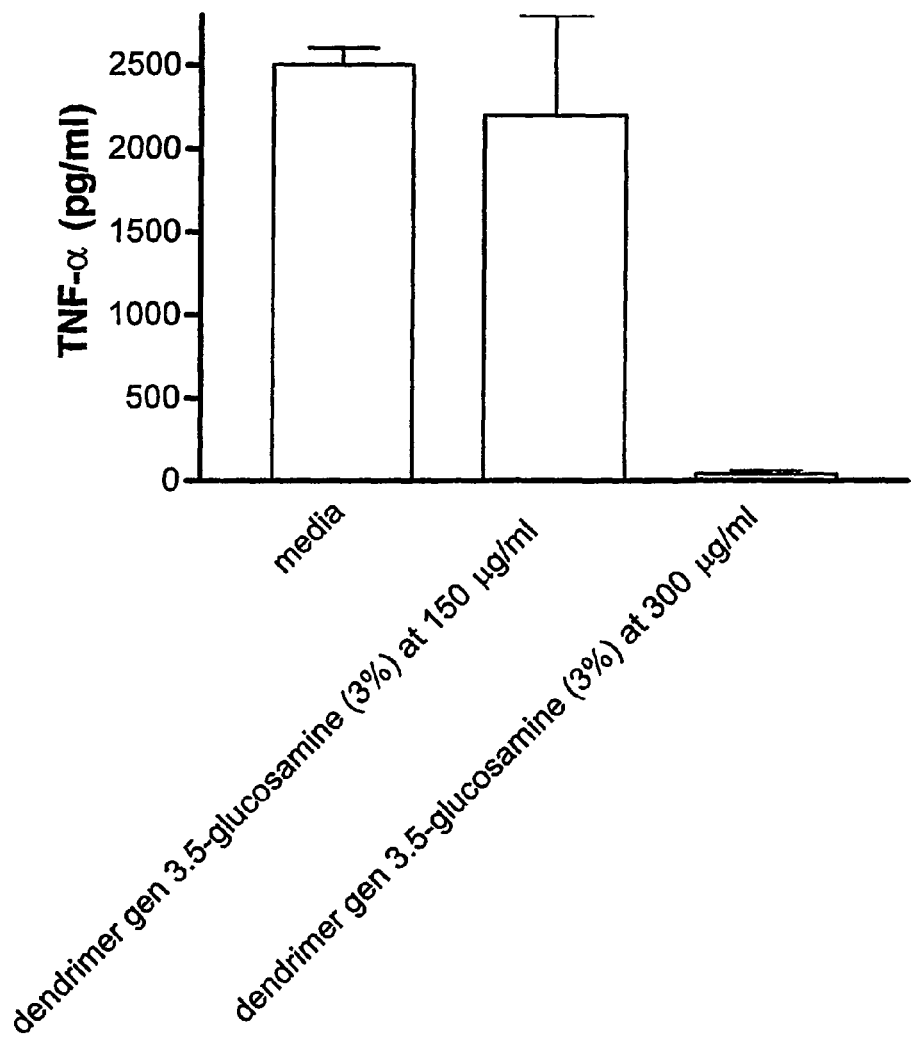

Experiment B 12: Single donor PBMN cells were isolated and resuspended in RPMI, L-glutamine, penicillin, streptomycin and 10% human serum at a density of $1 \times 10^6$ cells/ml. The cells were then plated (1 ml) in 12 well tissue culture plates and cultured for 15 min at 37° C. in 5% $CO_2$. Dendrimer gen 3.5-glucosamine in which the loading of glucosamine on the generation 3.5 dendrimer was 3% (rather than the 7% loading used in all the other experiments described) was then added at a concentration of 150 μg/ml or 300 μg/ml. The cells were cultured for 30 min at 37° C. in 5% $CO_2$ and LPS was then added at 5 ng/ml. Cell free culture supernatants were harvested 22 h later and assayed for MIP-1β as shown in FIG. 22(i), or for TNF-α as shown in FIG. 22(ii). For all of the chemokines and pro-inflammatory cytokines studied, a significant reduction in their release was seen when dendrimer gen 3.5-glucosamine was present.

EXAMPLES C

Experiments with the Mixing of Human Cells From Different Donors

Figure 23I:
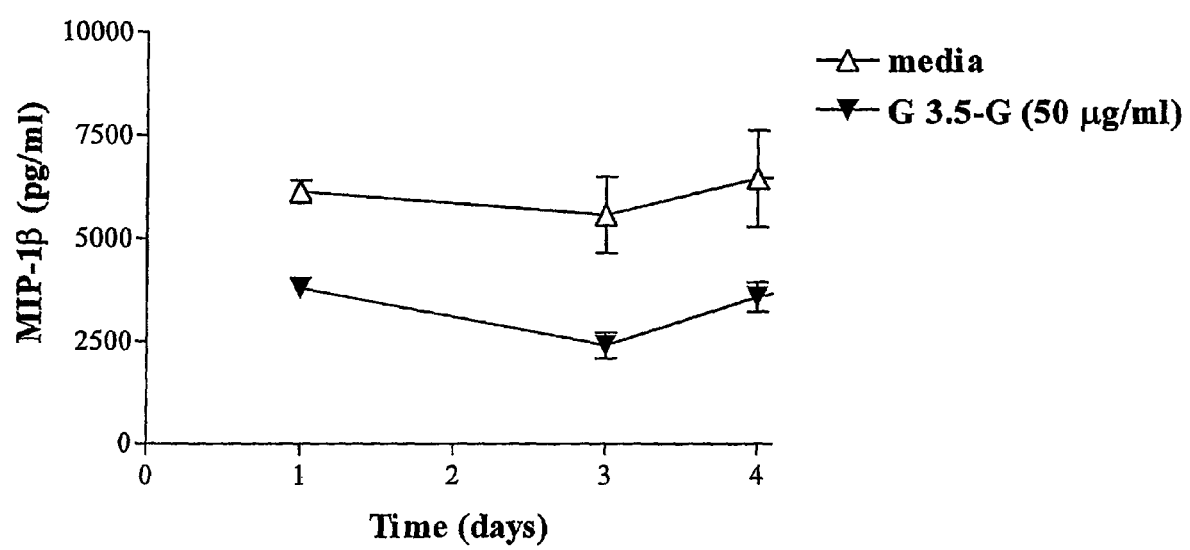
Figure 23:
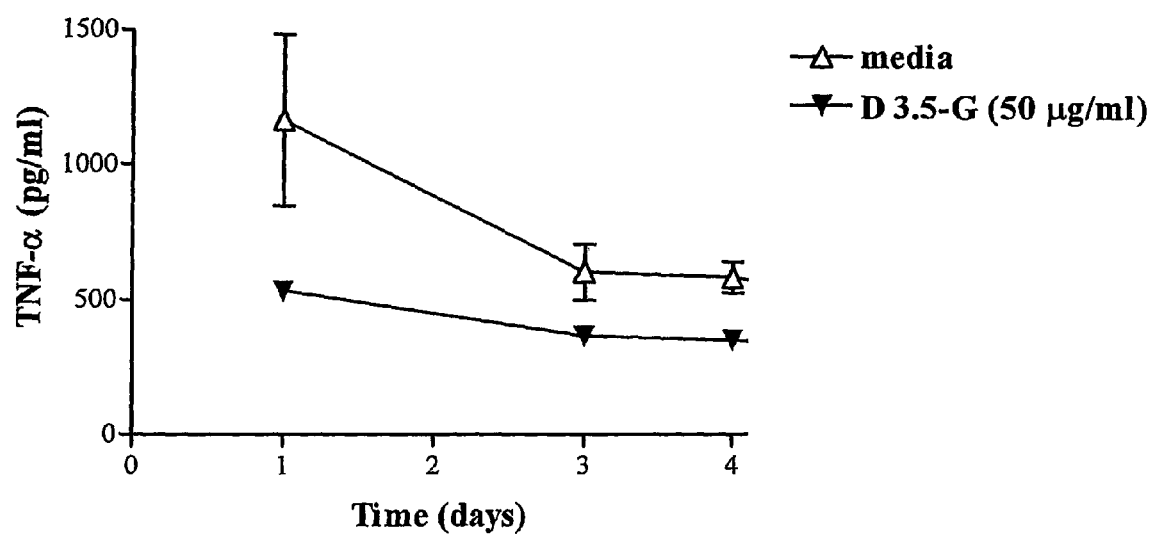

The Effect of the Dendrimer Gen 3.5-Glucosamine Conjugate on the Release of Chemokines and, in Turn, Cytokines after the Mixing of Human PBMN Cells from Several Donors:

Experiment C 13: Single donor PBMN cells were isolated from 3 individuals and the cell density adjusted to $1 \times 10^6$ cells/ml. The cells from all 3 donors were then mixed together for 72 h in a 12-well tissue culture plate. The dendrimer gen 3.5-glucosamine was then added at 50 μg/ml. Cell free culture supernatants were harvested 1 day, 3 days and 4 days later and assayed for MIP-1β and TNF-α. A significant reduction in MIP-1β and TNF-α release into the culture supernatant was seen at all 3 time points assayed as shown in FIGS. 23(i) and 23 (ii) respectively.

Experiment C 14: Single donor PBMN cells were isolated from 2 individuals and the cell density adjusted to $1 \times 10^6$ cells/ml. The cells were cultured separately for 24 h and then mixed together for 72 h in a 12-well tissue culture plate. The dendrimer gen 3.5-glucosamine was then added at 50 ttg/ml. Cell free culture supernatants were harvested 1 day, 3 days and 4 days later and assayed for MIP-1β. A significant reduction in MW-1β release into the culture supernatant was seen at all 3 time points assayed as shown in FIG. 23(iii).

Figure 24I:
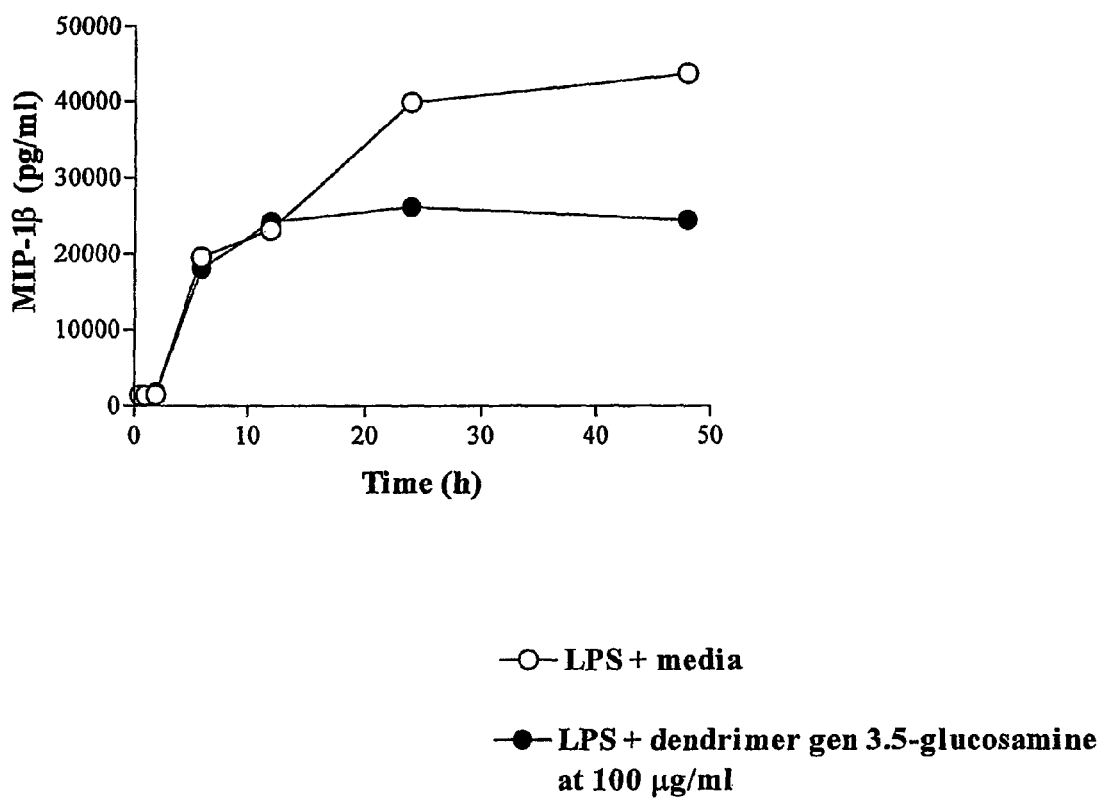

Experiment C 15: Single donor PBMN cells were isolated from 2 individuals and the cell density adjusted to $1 \times 10^6$ cells/ml. The cells were mixed together and dendrimer gen 3.5-glucosamine added at 100 μg/ml. LPS was added immediately afterwards at 10 ng/ml and cell free culture supernatants harvested at regular intervals for up to 48 h. A significant reduction in MIP-1β release into the culture supernatant was seen from 24 h onwards as shown in FIG. 24(i).

Experiment C 16: Single donor PBMN cells were isolated from 2 individuals and the cell density adjusted to $1 \times 10^6$ cells/ml. The cells were mixed together and dendrimer gen 3.5-glucosamine added at 100 μg/ml. LPS was added 24 hours later at a concentration of 5 ng/ml. Cell free culture supernatants were harvested at regular intervals for up to 96 h. A significant reduction in MIP-1β release into the culture supernatant was seen from 24 h onwards as shown in FIG. 24(ii).

EXAMPLES D

Cytokine and Chemokine Assays

Quantitation of MIP-1β and Other Chemokines and Cytokines in Tissue Culture Supernatants:

Levels of MIP-1β were measured in cell free culture supernatants using a commercially available enzyme immuno-assay (EIA; Quantiklne, R&D Systems). Dendrimers gen 3.5-glucosamine conjugates were first confirmed not to interfere with the assay by mixing rhMIP-1β at a final concentration of 125 μg/ml with the dendrimer gen 3.5-glucosamine conjugate at a final concentration of 200 μg/ml in growth medium. The solutions were incubated for 4 h at 37° C. and then run as samples in the EIA. There was no interference of the dendrimer gen 3.5-glucosamine with the M-1β assay (Table 4a).

There was no interference of the dendrimer gen 3.5-glucosamine with the MIP-1α, IL-8, IL-1β and IL-6 assays (Table 4a). In the case of TNF-α a low level interference was seen and this has been corrected for in the results shown in the figures (Table 4b).

EXAMPLES E

Other Biological Data

EXAMPLES E1

Preliminary Animal Toxicology

Anionic dendrimers gen. 3.5 are not toxic to mice at 90 mg/kg. Four Wistar rats were injected intravenously with dendrimer gen 3.5-glucosamine at a concentration of 30 mg/kg. This is equivalent to 6 mg/200 g rat. All animals were healthy at 24 h. They were then killed and examined. No gross pathology was seen in any of the organs.

EXAMPLES E 2

Anticoagulant Activity

The anticoagulant activity of each compound (ie: dendrimer gen 3.5, dendrimer gen 3.5 glucosamine, dendrimer gen 3.5-glucosamine 6-sulfate, dendrimer gen 3.5-glucosamine 3,6-disulfate, and dendrimer gen 3.5-glucosamine 3,4,6-trisulfate) was determined using the following in vitro assays:—kaolin partial thromboplastin time, prothrombin time, thrombin time and a Factor Xa assay. No anticoagulant activity was seen at the maximum concentration of 200 μg/ml that was analysed for all of the compounds tested. For dendrimer gen 3.5 glucosamine, this was also confirmed at a concentration of 300 μg/ml. The results are shown in Table 5. This is the first time that a sulphated polysaccharide has been made which has biological activity but no anticoagulant activity.

EXAMPLES E 3

Anti-HIV-1 Activity of Dendrimer-Sulfated Glucosamine Constructs

The anti-HIV-1 activity of dendrimers gen 3.5 glucosamine and the sulfated glucosamine conjugates synthesised was determined using C8166 cells and the HIV-1.IIIb virus up to a concentration of 100 μg/ml. No anti-MV-1 activity was seen.

EXAMPLES F

Biological Activity of Dendrimer Sulphated Glucosoamine

EXAMPLES F 1

Figure 25I:
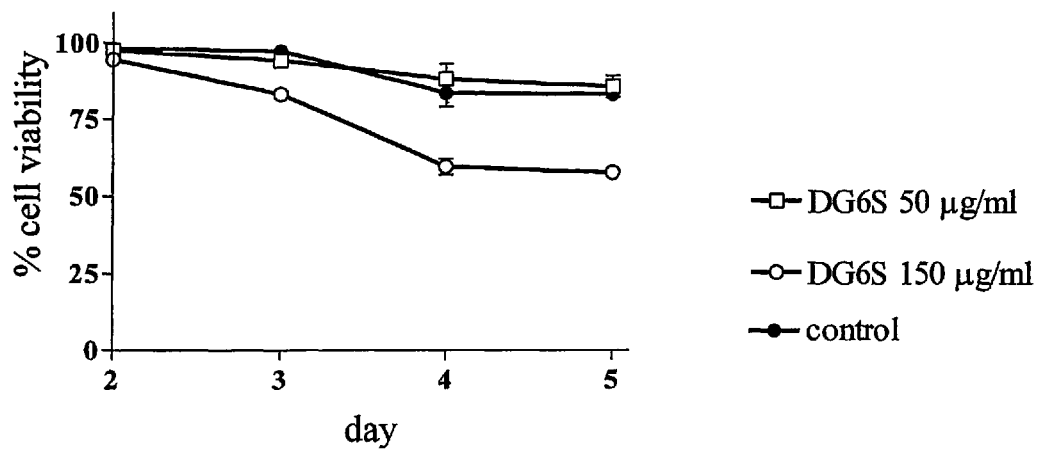
Figure 25:
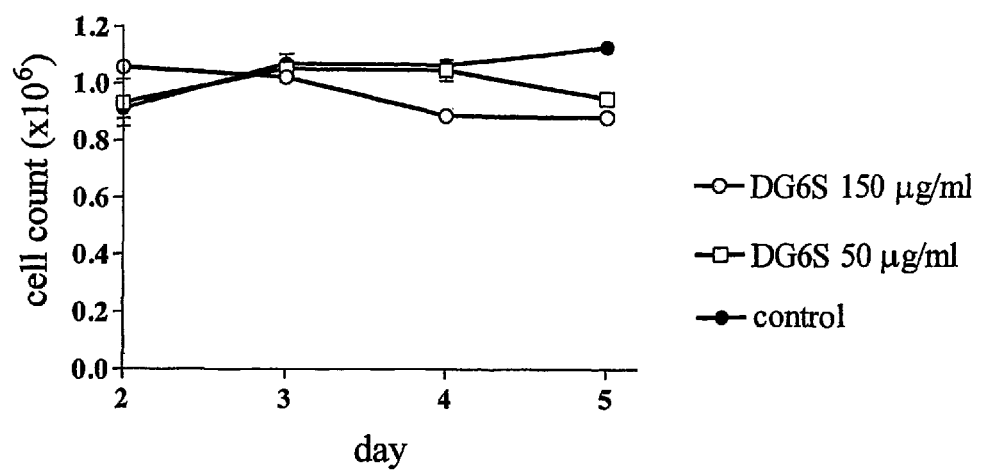
Figure 26:
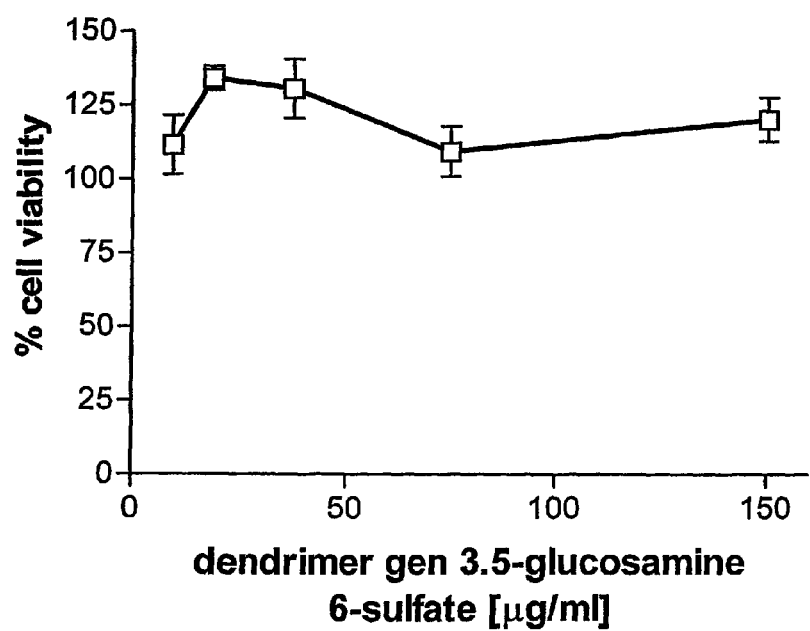

Dendrimer gen 3.5-Glucosamine 6-Sulfate Does Not Affect the Growth Characteristics of Human PBMN, Cells, Human MDMs or HUVECs at the Concentrations Used The dendrimer gen 3.5-glucosamine 6-sulfate did not affect cell viability or the growth characteristics of PBMN cells (FIG. 25(i) and FIG. 25(ii)), or of MDMs (FIG. 26) when present at a concentration of up to 150 μg/ml in cultures maintained for up to 5 days. Cell viability was determined by Trypan blue exclusion and an MTT assay. Furthermore, the dendrimer gen 3.5-glucosamine 6-sulfate construct was not toxic to HUVECs when added to cultures of these cells up to a concentration of 100 μg/ml for up to 72 hours (FIG. 27(i) and FIG. 27(ii) and FIG. 27(iii)).

EXAMPLES F 2

Figure 28I:
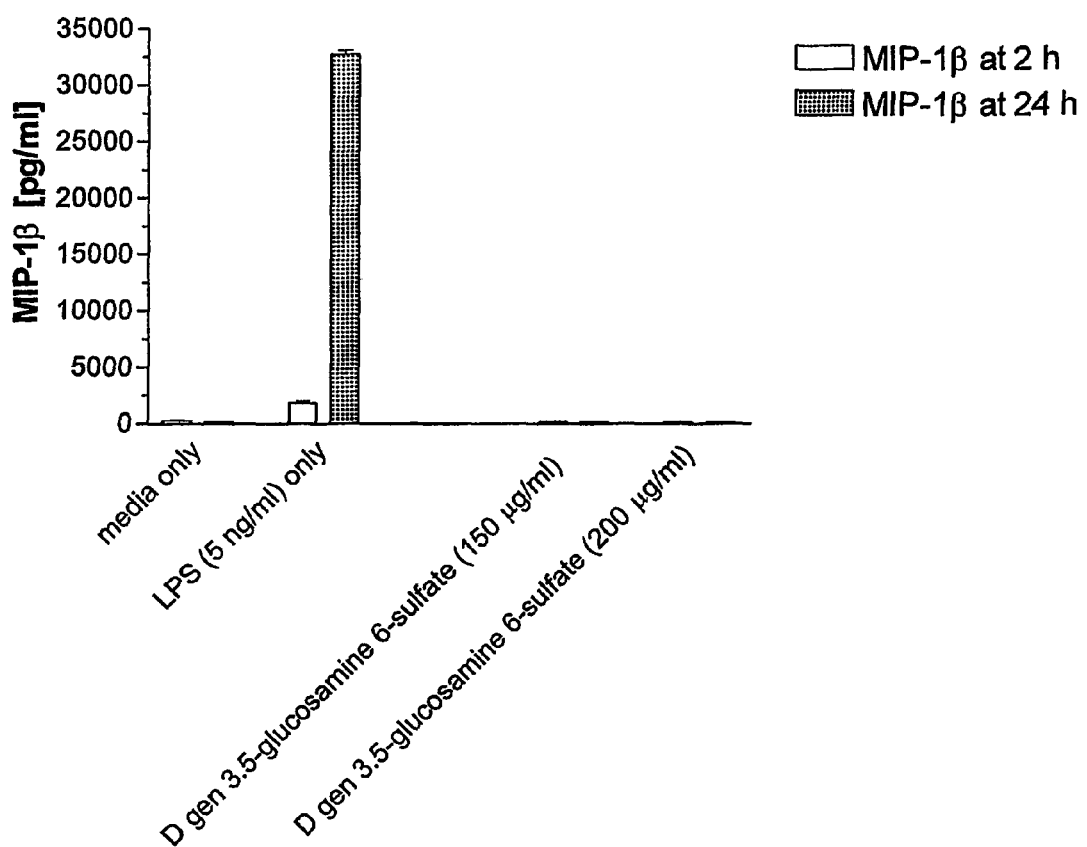

The Effect of Dendrimer Gen 3.5-glucosamine 6-sulfate on the Release of Chemokines and Cytokines by LPS from Single Donor Human PBMN Cells Single donor PBMN cells were isolated, resuspended in RPMI, L-glutamine, penicillin, streptomycin and 10% human serum at a density of $1\times10^6$ cells/ml. The cells were then plated (1 ml) in 12 well tissue culture plates and cultured for 15 min at 37° C. in 5% $CO_2$. Dendrimer gen 3.5-glucosamine 6-sulfate was then added at 150 μg/ml or at 200 μg/ml. The cells were cultured for 30 min at 37° C. in 5% $CO_2$ and LPS (5 ng/ml) added. Cell free culture supernatants were harvested 24 h later and assayed for MP-1β as shown in FIG. 28(i). A significant reduction in MIP-1β release was seen when dendrimer gen 3.5-glucosamine 6-sulfate was present.

Figure 28:
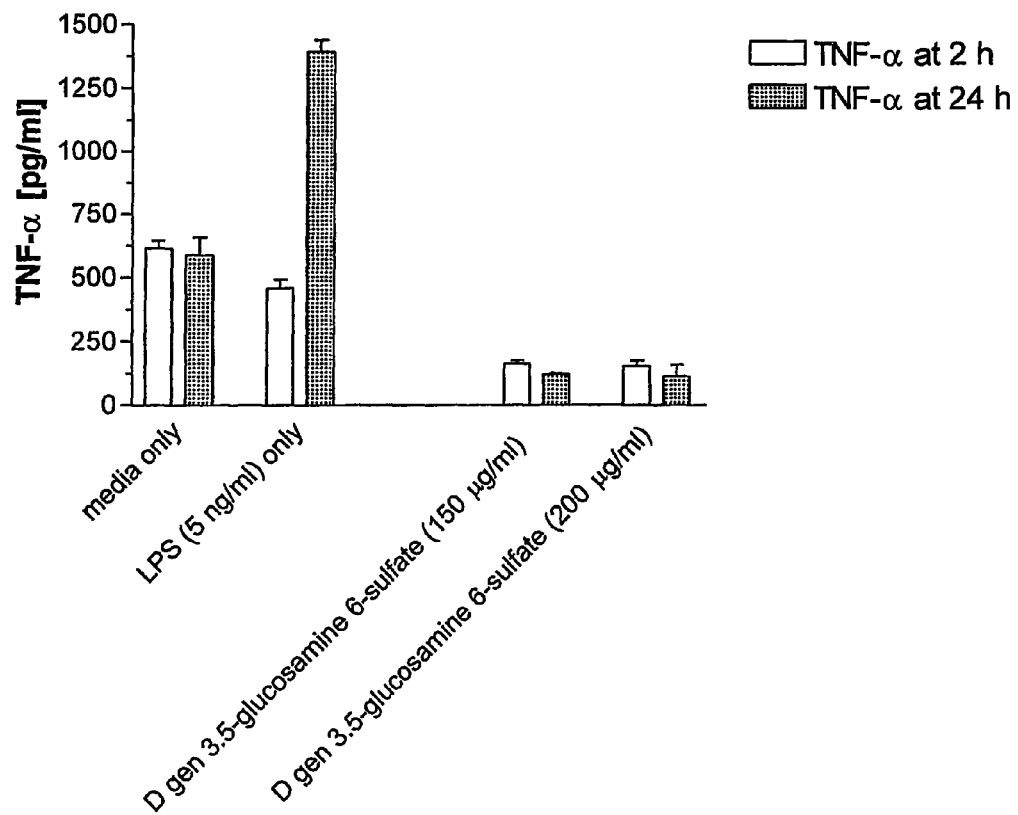

Cell free culture supernatants were also harvested and assayed for TNF-α as shown in FIG. 28(ii). A significant reduction in TNF-α release was seen when dendrimer gen 3.5-glucosamine 6-sulfate was present at 150 μg/ml or at 200 μg/ml.

EXAMPLES F 3

Figure 29:
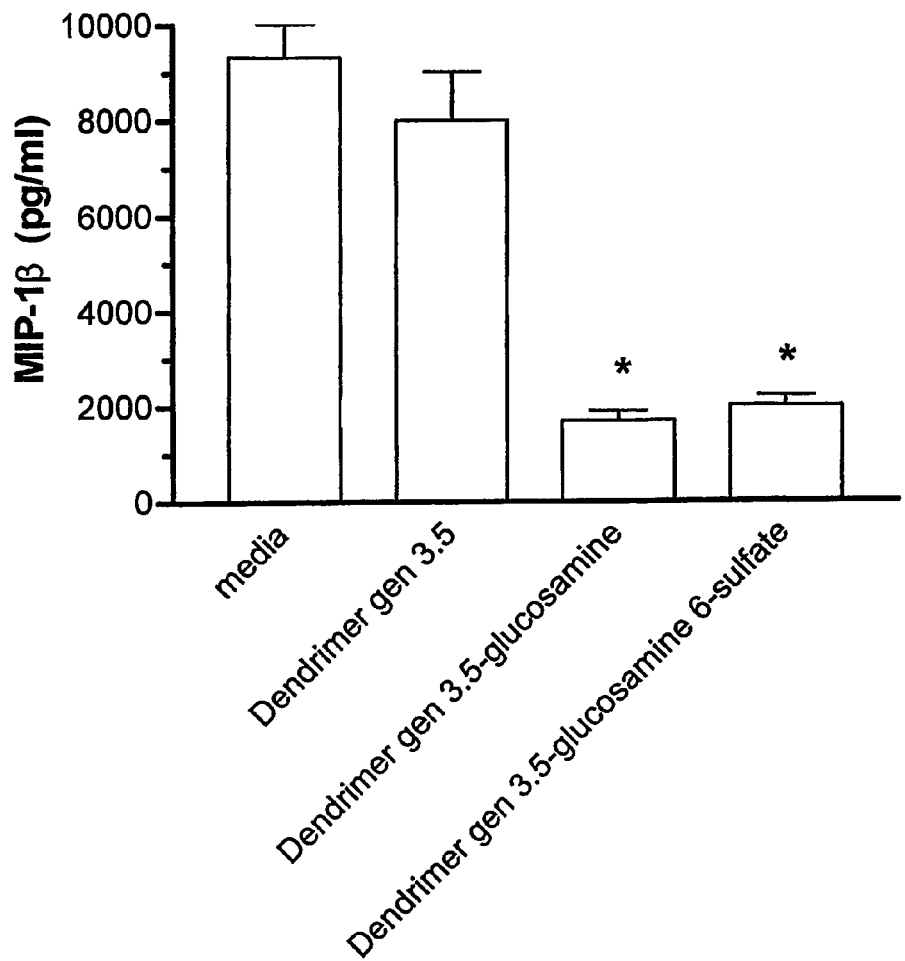

The Effect of Dendrimer Gen 3.5-Glucosamine 6-Sulfate on the Release of Chemokines and Cytokines after the Mixing of Human MDMs from Four Donors Single donor PBMC cells were isolated from 4 individuals by density gradient centrifugation and then mixed together for 24 h. The cells were re-suspended in growth medium (RPMI 1640, 20 mM L-glutamine, penicillin [250 IU/ml], streptomycin [250 μg/ml] and 10% human serum) and the cell density adjusted to $2\times10^6$ cells/ml. To separate MDMs, the cells were plated in a plastic dish for 2 h and the MDMs then scraped, washed, and resuspended in growth medium. They were then re-plated at a density of $1\times10^6$ cells/ml and left in culture for 72 hours before adding either dendrimer gen 3.5-glucosamine or dendrimer gen 3.5-glucosamine 6-sulfate at a concentration of 25 μg/ml. Cell free culture supernatants were harvested 36 h later and assayed for MIP-1β as shown in FIG. 29. A significant reduction in MIP-1β release was seen when dendrimer gen 3.5-glucosamine was present as well as when dendrimer gen 3.5-glucosamine 6-sulfate was present.

EXAMPLES F 4

Endothelial Microtubule Formation Assay to Determine the Anti-Angiogenic Activity of Compounds Kubota et al. reported that human umbilical vein endothelial cells undergo morphological differentiation with tube formation when cultured on a reconstituted gel composed of basement membrane proteins (Matrigel; Beckton-Dickinson)

(Kubota, Y., H. K. Kleinman, G. R. Martin, and T. J. Lawley. 1988. Role of laminin and basement membrane in the morphological differentiation of human endothelial cells into capillary-like structures. J. Cell. Biol. 107: 1589-1598). This has parallels with the in vivo situation where endothelial cells line the lumen of blood vessels and are in contact with the extracellular matrix of basement membranes that are composed of collagen IV, heparan sulphate proteoglycan and the glycoproteins laminin and nidogen/entactin.

Due to the ability of basement membranes to stimulate differentiation, cells plated onto the gel attach rapidly. Within one to two hours, elongated processes are observed. After eight hours, the endothelial cell cultures show abundant networks of branching and anastomosing of cords of cells. By eighteen hours, the endothelial cells have formed an interconnected network of anastomosing cells which, by low power light microscopy, have a honeycomb appearance. The tube like structures formed by endothelial cells on Matrigel persist for several days. The formation of the tube structures is not dependent on extracellular growth factors or the presence of heparin in the culture media. Tube formation also seems to be relatively specific for endothelial cells because neither human dermal fibroblasts nor human smooth muscle cells form tubes when cultured on Matrigel.

Ultrastructural EM studies have confirmed that the anastomosing cytoplasmic extensions of the morphologically differentiated endothelial cells contain a lumen that is completely encircled by one or two endothelial cells in cross section. The lumen contains various amounts of degenerated cytoplasm, suggesting that very rapid remodelling of the cell takes place during tube formation. Viability studies of endothelial cells cultured on Matrigel do not indicate that cell death plays an important role in tube formation. Moreover, these differentiated cells retain the characteristic Weibel-Palade bodies of endothelial cells.

The endothelial microtubule formation assay was performed by isolating human umbilical vein endothelial cells from umbilical cords within 6 h of delivery by caesarean section. The embilical vein was cannulated and 0.1% collagenase in phosphate buffered saline was introduced and incubated for 20 minutes. The endothelial cells liberated by the collagenase were obtained by washing the umbilical vein with Medium 199. The cells were washed three times with Medium 199 and then cultured in tissue culture flasks coated with fibronectin. Growth media consisted of Medium 199 with 20% foetal bovine serum, 30 µg/ml endothelial cell growth supplement, 10 IU/ml heparin, 100 IU/ml penicillin, 100 µg/1 ml streptomycin and 2 mM L-glutamine. Human umbilical vein endothelial cells were passaged at confluence after treatment with trypsin-EDTA. All cells were used at passages to 6.

Aliquots of Matrigel were dispensed into 35 mm diameter tissue culture dishes on ice and then incubated at 37° C. for 10 min to allow the gel to set. Dendrimer gen 3.5-glucosamine 6-sulfate was prepared in HUVEC growth medium and added to the dishes at several different concentrations. HUVEC's at passage 3 to 6 were harvested using trypsin and suspended in growth medium at a density of $2-3\times10^5$ cells/ml. One ml aliquots of the cell suspension were added to the plates containing the dendrimer gen 3.5-glucosamine 6-sulfate and incubated at 37° C., 5% $CO_2$. At various time points from 8-24 hours, the plates were examined and scored using a published scheme from 0-4, where 0=all adherent cells remain single, and 4=all adherent cells involved in tubular structures. New vessel formation was quantified blind by three different observers at 18 h. The within-observer and between-observer variability was <10% (n=4). The results are shown in Table 6 and photographs of the assay in FIGS. 30 to 32. Dendrimer gen 3.5-glucosamine 6-sulfate significantly reduced the level of tube formation at 12 µg/ml and abolished it completely at 75 µg/ml to 100 µg/ml.

The in vitro model of migration and microvessel formation used for testing dendrimer gen 3.5-glucosamine 6-sulfate fulfilled the two hallmarks of angiogenesis; ie: endothelial cell proliferation and capillary sprouting. Our in vitro observations show that dendrimer gen 3.5-glucosamine 6-sulfate inhibits new vessel formation by normal endothelial cells and that this prevents new blood vessel formation; ie: angiogenesis.

EXAMPLES F 5

In Vitro Angiogenesis Assay

Blood vessels (approximately 1-2 mm diameter) were excised from the apical surface of human placentas within 6 h of an elective Caesarian birth. The use of the placentas was approved by the Ethics Committee of Hammersmith Hospitals Trust, London. The blood vessels were placed in Hank's balanced salt solution and cut into 1-2 mm fragments using fine dissecting forceps and iridectomy scissors. Residual clots were removed and the blood vessels then soaked in Hank's balanced salt solution.

The effect of each compound on new blood vessel formation was determined by culturing the blood vessels within a fibrin clot in 24-well tissue culture plates. Thirty µl of bovine thrombin (50 NIH U/ml in 0.15 M sodium chloride) was added to each well followed by 1 ml/well of 3 mg/ml bovine fibrinogen in Medium 199. The thrombin and fibrinogen were rapidly mixed and a blood vessel fragment placed in the centre of the well. Fibrin gel formation occurred rapidly and left the vessel suspended within the gel. One ml/well of Medium 199 supplemented with 20% foetal calf serum, 250 IU/ml penicillin and 250 U/ml streptomycin was then added to each well. $\epsilon$-amino-n-caproic acid was also added (300 µg/ml) for the first 4 days and twice weekly thereafter (50 µg/ml) in order to prevent dissolution of the fibrin clot. The vessels were cultured at 37° C. in a humidified incubator for 25 days with the media being changed twice weekly.

The degree of new vessel formation was quantified blind twice a week by three different observers using a visual analogue scale in which 0=no growth, 1=very little new vessel formation, 2=significant new vessel formation and 3=dense new vessel formation. An angiogenesis score was derived from the counts undertaken for each well by dividing the total score by the maximum score possible and then expressing the result as a percentage. On 2 separate occasions, each compound was tested in quadruplicate replicate wells. Experiments in which blood vessels were cultured in MCDB 131 (i.e.: serum free media) showed that serum factors were not necessary for new blood vessel formation. Some of the fibrin clots were fixed overnight in 10% formalin, paraffin embedded, sectioned for histology and then stained for the endothelial cell markers Factor VIR and CD31.

Over the 28 day course of the assay, a complex arcade of microvessels emerged from the cut section of the blood vessel embedded within a fibrin clot. Very little growth of new vessels was seen from those areas of the vessel which had not been sectioned. The first blood vessels appeared by day 4 and were usually blunt-ended. Over the next 18 days, they went on to branch and give rise to complex arcades of vessels. Growth was rapid for the first 2 weeks and then slowed considerably. These new vessels were lined by endothelial cells as shown by positive immunohistochemistry for Factor VIf and CD31.

In six experiments performed, there was a reduction in the number of new vessels that were formed when dendrimer gen 3.5-glucosamine 6-sulfate was present at 25 µg/ml (FIG. 33). The inhibition of new vessel formation was more marked and significant (p<0.05) when the dendrimer gen 3.5-glucosamine 6-sulfate was present at 50 µg/ml. This effect was first seen at day 18 with the difference persisting and becoming greater until day 28. The experiment was terminated on day 32.

EXAMPLE G

Model System for a Mixed Lymphocyte Reaction

The present invention also provides a model system for the mixed lymphocyte reaction that can be used to evaluate compounds that inhibit the complex process of allograft organ rejection. The results from these experiments are shown in FIG. 23(i), FIG. 23 (ii), FIG. 23 (iii), FIG. 24(i), and FIG. 24 (ii). Using our experimental model system, we have evaluated the anti-inflammatory activity of dendrimer gen. 3.5-glucosamine and by dendrimer gen. 3.5-glucosamine 6-sulfate. Our results show that the mixed lymphocyte reaction can be successfully inhibited by dendrimer gen. 3.5-glucosamine as well as by dendrimer gen. 3.5-glucosamine 6-sulfate, and that they could therefore be of therapeutic use in preventing the inflammatory response seen when rejection of a syngeneic, autologous, allogeneic or or xenogenic organ transplant occurs. It may also be effective in maintaining the counter inflammatory environment that is required to prevent the rejection of the transplanted organ, as well as the development of graft-versus-host disease.

The mixed lymphocyte reaction can be used to test the responsiveness of recipient lymphocytes to antigens expressed on donor cells. Low recipient anti-donor mixed lymphocyte reaction responses are associated with excellent transplant survival. The test is especially important in bone marrow transplantation, because it also assesses whether the donor bone marrow cells can respond to recipient antigens and cause graft-versus-host disease.

EXAMPLE H

The Biological Activity of Dendrimer Gen 3.5 Glucosamine on Cells of Dendritic Cell Origin Immature monocyte derived dendritic cells were prepared as follows. Freshly isolated PBMN cells from a single donor were obtained and the monocytes isolated by adhesion to gelatin coated flasks for 1 hour. The isolated monocytes were cultured for 5 days in RPMI containing penicillin and streptomycin and L-glutamine and 10% autologous heat inactivated human serum with Interleukin-4 (1,000 IU/ml) and GM-CSF (150 µu/ml). These cells were confirmed to be immature monocyte derived dendritic cells because of the following phenotype on FACS analysis: CD3-, CD4-, CD14-, CD16-, CD25-, CD80-, CD83- and HLA-DR+. Tissue derived, human peritoneal dendritic cells were isolated using the Milteny Biotech CD1c isolation kit. These cells were confirmed to be immature tissue derived dendritic cells because of the following phenotype on FACS analysis: CD3-, CD4-, CD14-, CD16-, CD25-, CD80-, CD83- and HLA-DR+. The blood—or tissue-derived human dendritic cells (i.e stimulator cells) were then irradiated to prevent their proliferation by exposing them to 30 Gy γ irradiation.

For the mixed lymphocyte reaction, responder cells were prepared from single donor PBMN cells by first allowing them to adhere to plastic for 1.5 hours. The non-adherent fraction from these PBMN cells is rich in T cells and they were used as the responder cells. The cells were cultured in RPMI and penicillin and streptomycin and L-glutamine and 10% heat inactivated human serum. The irradiated stimulator cells were mixed with the responder lymphocytes. The allogeneic mixed lymphocyte reaction was incubated at 37° C. for 5 days and it was then pulsed with [$^3$H] thymidine (1 µCu/well) and incubated at 37° C. for another 18 hours. The cells were then harvested and the [$^3$H] thymidine incorporated measured.

Experiment H1

Figure 35:
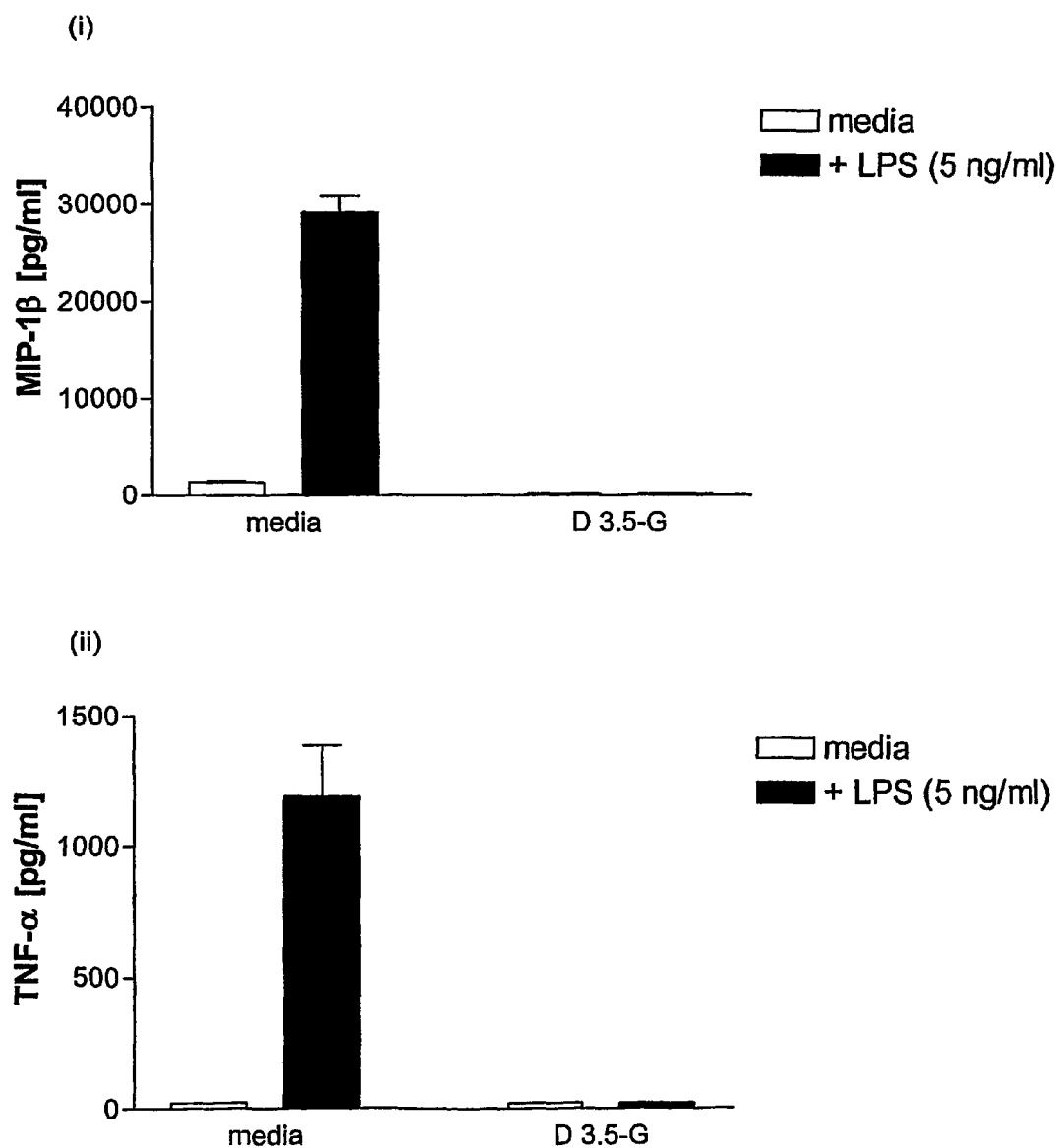

Lipopolysaccharide leads to the immunological stimulation of immature dendritic cells. Monocyte derived dendritic cells were prepared as described and plated at 1×10$^5$/well. Dendrimer gen 3.5-glucosamine (200 µg/ml) was added for 1 hour followed by LPS (5 ng/ml). Cell free culture supernatants were harvested 21 h later and assayed for MIP-1β as shown in FIG. 35(i) and for TNF-α as shown in FIG. 35(ii). For the cheinokine and the cytokine studied, a significant reduction in their release was seen when dendrimer gen 3.5-glucosamine was present.

Experiment H2

Figure 36:
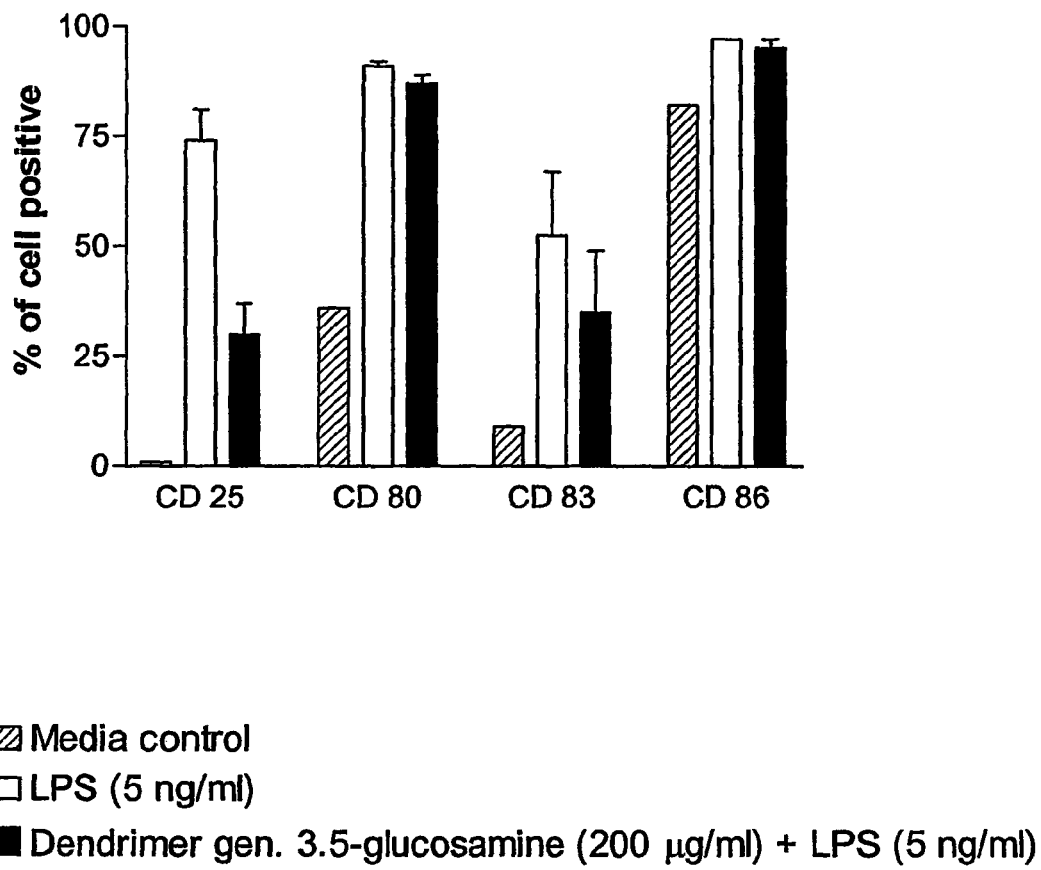

Lipopolysaccharide leads to the maturation of immature dendritic cells as demonstrated by their increased expression of cell surface CD25, CD80, CD83 and CD86. The ability of dendrimer gen. 3.5-glucosamine to interfere with this LPS induced maturation of dendritic cells was determined. Immature monocyte derived dendritic cells were prepared as described and plated at 1×10$^6$/well. Dendrimer gen 3.5-glucosamine (200 µg/ml) was added for 1 hour followed by LPS (5 ng/ml). The cells were cultured for 21 hours and then harvested for FACS analysis. As shown in FIG. 36, dendrimer gen. 3.5-glucosamine significantly reduced LPS induced upregulation of CD25 on the dendritic cells.

Experiment H3

Co-culture of dendritic cells and T lymphocytes leads to a mixed lymphocyte reaction as measured by [$^3$H] thymidine uptake. Additional proliferation occurs if lipopolysaccharide (LPS) is also added. Gamma irradiated purified monocyte derived dendritic cells were incubated in round-bottomed 96 well culture plates in triplicate in aliquots ranging from 64,000 to 32 dendritic cells/well in RPMI 1640 supplemented with 330 µg/ml L-glutamine, 200 IU/ml penicillin, 200 µg/ml streptomycin and 10% heat inactivated human serum with dendrimer gen. 3.5 glucosamine (200 µg/ml) for 1 hour at 37° C. with 5% CO$_2$. The control wells contained media only. Allogeneic peripheral blood lymphocytes (100,000/well) were then added. Other control wells contained only the peripheral blood lymphocytes. The total volume per well was 250 µl. The plates were incubated for 5 days at 37° C. with 5% CO$_2$. In addition, prior to adding the peripheral blood lymphocytes, the plates (with and without dendrimer gen. 3.5 glucosamine) were incubated with lipopolysaccharide at a concentration of 5 ng/ml for 21 hours. The cells were then washed three times. Dendrimer gen. 3.5 glucosamine was then added back at a concentration of 200 µg/mil. Peripheral blood lymphocytes were added at 100,000 cells/well and the plates incubated for 5 days at 37° C. with 5% $CO_2$. To these cultures, [$^3$H]-Thymidine (1 µCi/well) was then added for a further 18 hours and the cells cultured. After this time, the cells were harvested and proliferation measured using a liquid scintillation counter. The counts per minute (cpm) for the peripheral blood lymphocyte control well were subtracted from the actual cpm of each experiment in order to determine the mean cpm of [$^3$H]-Thymidine incorporation. FIG. 37 shows the results from three experiments. In each case, the proliferation caused by the mixed lymphocyte reaction as well as the proliferation caused by LPS at 5 ng/ml was significantly inhibited.

Experiment H4

Gamma irradiated purified monocyte derived dendritic cells were incubated in round-bottomed 96 well culture plates in triplicate in aliquots ranging from 64,000 to 32 dendritic cells per well in RPMI 1640 supplemented with 330 µg/ml L-glutamine, 200 IU/ml penicillin, 200 µg/ml streptomycin and 10% heat inactivated human serum with dendrimer gen. 3.5 glucosamine (200 µg/ml) for 1 hour at 37° C. with 5% $CO_2$. The control wells contained media only. Allogeneic peripheral blood lymphocytes (100,000/well) were then added. Other control wells contained only peripheral blood lymphocytes. The total volume per well was 250 iii. The plates were incubated for 5 days at 37° C. with 5% $CO_2$. In addition, prior to adding the peripheral blood lymphocytes, the plates (with and without dendrimer gen. 3.5 glucosamine) were incubated with lipopolysaccharide at a concentration of 20 ng/ml for 21 hours. The cells were then washed three times. Dendrimer gen. 3.5 glucosamine was then added back at a concentration of 200 µg/ml. Peripheral blood lymphocytes were added at 100,000 cells/well and the plates incubated for 5 days at 37° C. with 5% $CO_2$. To these cultures, [$^3$H]-Thymidine (1 µCi/well) was then added for a further 18 hours and the cells cultured. After this time, the cells were harvested and proliferation measured using a liquid scintillation counter. The counts per minute (cpm) for the peripheral blood lymphocyte control well were subtracted from the actual cpm of each experiment in order to determine the mean cpm of [$^3$H]-Thymidine incorporation. FIG. 38 shows the results from two experiments. In each case, the proliferation caused by the mixed lymphocyte reaction as well as the proliferation caused by LPS at 20 ng/ml was significantly inhibited.

Experiment H5

The ability of dendrimer gen. 3.5-glucosamine to reduce proliferation was determined. Gamma irradiated isolated, purified peritoneal dendritic cells were incubated in round bottomed 96-well tissue culture plates in triplicate in aliquots ranging from 64,000 to 32 dendritic cells/well in RPMI 1640 supplemented with 330 µg/ml L-glutamine, 200 IU/ml penicillin 200 µg/ml streptomycin and 10% heat inactivated human serum with dendrimer gen. 3.5 glucosamine (200 µg/ml) for 1 hour at 37° C. with 5% $CO_2$. The control wells contained media only. Allogeneic peripheral blood lymphocytes (100,000/well) were then added. Other control wells contained only the peripheral blood lymphocytes. The total volume per well was 250 µl. The plates were incubated for 5 days at 37° C. with 5% $CO_2$. In addition, prior to adding the peripheral blood lymphocytes, the plates (with and without dendrimer gen. 3.5 glucosamine) were incubated with lipopolysaccharide at a concentration of 5 ng/ml for 21 hours. The cells were then washed three times. Dendrimer gen. 3.5 glucosamine was then added back at a concentration of 200 µg/ml. Peripheral blood lymphocytes were added at 100,000 cells/well and the plates incubated for 5 days at 37° C. with 5% $CO_2$. To these cultures, [$^3$H]-Thydine (1 µCi/well) was then added for a further 18 hours and the cells cultured. After this time, the cells were harvested and proliferation measured using a liquid scintillation counter. The counts per minute (cpm) for the peripheral blood lymphocyte control well were subtracted from the actual cpm of each experiment in order to determine the mean cpm of [$^3$H]-Thymidine incorporation. FIG. 39 shows the results from three experiments. In each case, the proliferation caused by the mixed lymphocyte reaction as well as the proliferation caused by LPS at 5 ng/ml was significantly inhibited.

Experiment H6

Gamma irradiated isolated, purified peritoneal derived dendritic cells were incubated in round bottomed 96-well culture plates in triplicate in aliquots ranging from 64,000 to 32 dendritic cells/well in RPMI 1640 supplemented with 330 µg/ml L-glutamine, 200 IU/ml penicillin, 200 µg/ml streptomycin and 10% heat inactivated human serum with dendrimer gen. 3.5 glucosamine (200 µg/ml) for 1 hour at 37° C. with 5% $CO_2$. The control wells contained media only. Allogeneic peripheral blood lymphocytes (100,000/well) were then added. Other control wells contained only peripheral blood lymphocytes. The total volume per well was 250 µl. The plates were incubated for 5 days at 37° C. with 5% $CO_2$. In addition, prior to adding the peripheral blood lymphocytes, the plates (with and without dendrimer gen. 3.5 glucosamine) were incubated with lipopolysaccharide at a concentration of 20 ng/ml for 21 hours. The cells were then washed three times. Dendrimer gen. 3.5 glucosamine was then added back at a concentration of 200 µg/ml. Peripheral blood lymphocytes were added at 100,000 cells/well and the plates incubated for 5 days at 37° C. with 5% $CO_2$. To these cultures, [$^3$H]-Thymidine (1 µCi/well) was then added for a further 18 hours and the cells cultured. After this time, the cells were harvested and proliferation measured using a liquid scintillation counter. The counts per minute (cpm) for the peripheral blood lymphocyte control well were subtracted from the actual cpm of each experiment in order to determine the mean cpm of [$^3$H]-Thymidine incorporation. FIG. 40 shows the results from two experiments. In each case, the proliferation caused by the mixed lymphocyte reaction as well as the proliferation caused by LPS at 20 ng/ml was significantly inhibited.

Experiment H7

In this experiment, the effect of dendrimer gen. 3.5 glucosamine on the release of IL-2 and γ-interferon during the mixed lymphocyte reaction in the presence of lipopolysaccharide was determined. Gamma irradiated purified monocyte derived dendritic cells or gamma irradiated isolated, purified peritoneal dendritic cells were incubated in round bottomed 96-well culture plates in duplicate in aliquots ranging from 32,000 to 2,000 dendritic cells/well in RPMI 1640 supplemented with 330 µg/ml L-glutamine, 200 IU/ml penicillin, 200 µg/ml streptomycin and 10% heat-inactivated human serum. Dendrimer gen. 3.5 glucosamine (200 µg/ml) was added for 1 hour at 37° C. and 5% $CO_2$. Lipopolysaccharide (20 ng/ml) was then added for 21 hours. The cells were then washed three times with media and the dendrimer gen. 3.5 glucosamine (200 jLg/ml) replaced. Allogeneic lymphocytes (100,000/well) were then added and this was defined as day 0. The plates were incubated at 37° C. and 5% $CO_2$ and cell free culture supernatants were collected at day 3 and day 5 for the measurement of interleukin-2 and γ-interferon (EIA; R&D Systems).

FIG. 41(i) shows the results for gamma irradiated purified monocyte derived dendritic cells, and FIG. 41(ii) shows the results for gamma irradiated isolated, purified peritoneal dendritic cells. With each cell type, the dendrimer gen. 3.5 glucosamine caused a significant reduction in the release of interleukin-2 and of γ-interferon.

EXAMPLE J

Experiments with Superantigen Toxins

Bacterial superantigens are amongst the most lethal of toxins. Superantigens produced by *Staphylococcus aureus* and *Streptococcus pyogenes* trigger an excessive cellular immune response that can lead to lethal toxic shock. The family of superantigens includes staphylococcal enterotoxins SEA-SEE (among which SEB is most prominent), toxic shock syndrome toxin 1 (TSST-1) and the streptococcal pyrogenic exotoxins SPEA and SPEC. In the case of SEB, it can activate 30-40% of T cells to divide and produce cytokines. Toxicity results from the massive induction of chemokines and cytokines from cells of the immune system. The aim of the experiments that are described was to try and block these lethal effect of the superantigen toxin with dendrimer gen. 3.5-glucosamine at the beginning of this cascade; i.e. before activation of T cells can take place. The clinical rationale for doing this is that patients who produce higher levels of inflammatory cytokines in response to streptococcal superantigen toxins develop significantly more severe clinical manifestations of the disease than do patients who produce lower levels of these inflammatory cytokines in response to superantigen toxins (A. Norrby-Teglund et al. European Journal of Immunology, 2000; 30: 3247-3255).

Figure 42:
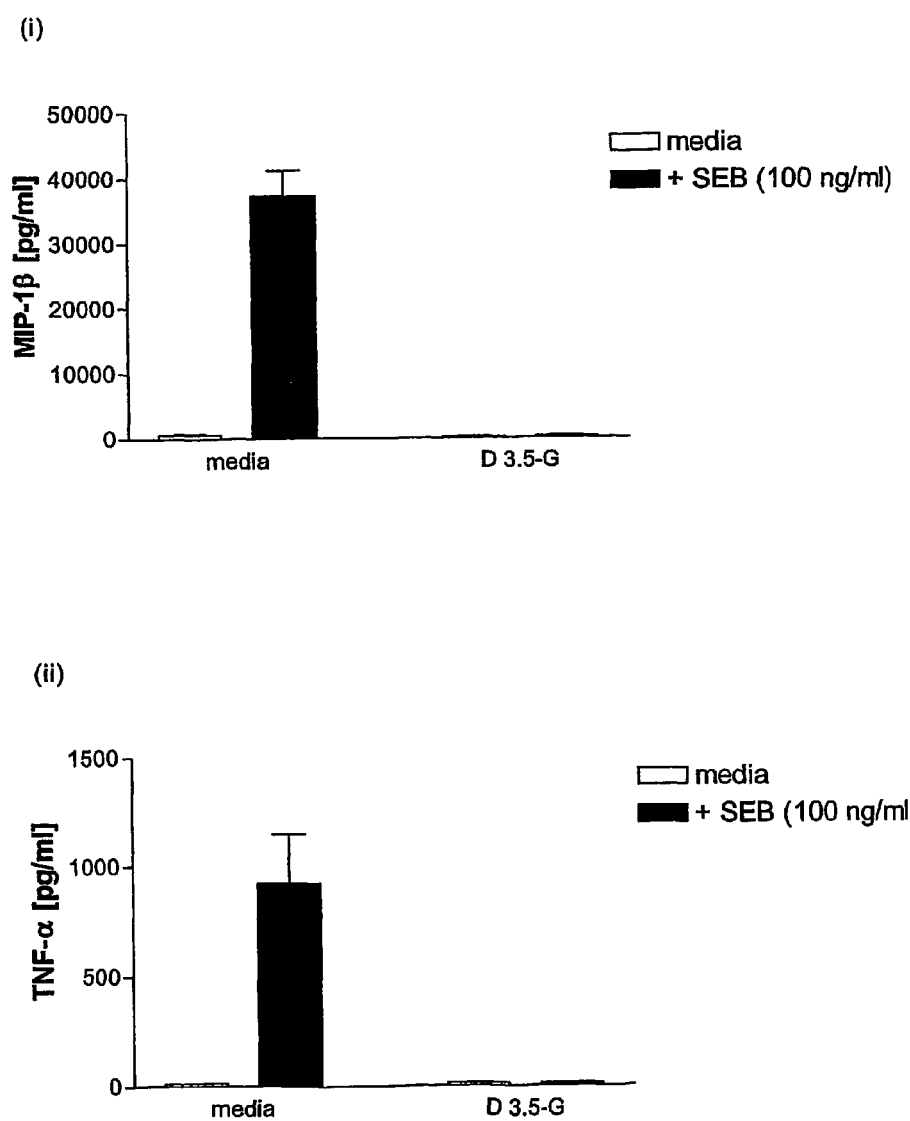

Experiment J1: Single donor PBMN cells were isolated and resuspended in RPM, L glutamine, penicillin, streptomycin and 10% human serum at a density of $1 \times 10^6$ cells/ml. The cells were then plated (1 ml) in 12 well tissue culture plates and cultured for 15 min at 37° C. in 5% $CO_2$. Dendrimer gen 3.5-glucosamine was then added at 200 μg/ml. The cells were cultured for 30 rin at 37° C. in 5% $CO_2$ and the superantigen SEB was then added at 100 ng/ml. Prior to using the SEB, it was confirmed that the SEB did not contain any LPS using the *limulus* assay. Cell free culture supernatants were harvested 21 h later and assayed for MIP-1β as shown in FIG. 42(i) and for TNF-α as shown in FIG. 42(ii). For both the chemokine and the cytokine a significant reduction in their release was seen when dendrimer gen 3.5-glucosamine was present.

Figure Legends: (All Results Are Expressed As The Mean±Sem.)

FIGS. 1a and 1b:
Structures of PAMAM anionic dendrimers gen 2.5 (a) and PAMAM anionic dendrimers gen 3.5 (b).
Dendrimers gen 2.5: MWt=6,011 Daltons; 32 carboxylic surface groups.
Dendrimers gen 3.5: MWt=12,419 Daltons; 64 carboxylic surface groups.

FIG. 2:
Schematic representation of the conjugation of glucosamine or sulfated glucosamine to PAMAM anionic dendrimers.
1 represents glucosamine (R=H, $R_1$=H, $R_2$=H) or glucosamine 6-sulfate (R=$SO_3H$, $R_1$=H, $R_2$=H) or glucosamine 3,6-disulfate (R=$SO_3H$, $R_1$=$SO_3H$, $R_2$=H) or glucosamine 3,4,6-trisulfate (R=$SO_3H$, $R_1$=$SO_3H$, $R_2$=$SO_{31}$).
2 represents PAMAM anionic dendrimers gen 2.5 (x equal 32) or PAMAM anionic dendrimers gen 3.5 (x equal 64).
3 represents 1-ethyl-3-(3-dimethylaminopropyl)carbodiimide hydrochloride used as the condensing agent. y molecules of glucosamine or sulfated glucosamine bound to the dendrimers.

FIG. 3:
Gel filtration of dendrimers gen 3.5-glucosamine mixture.
At the end of the reaction time 0.5 ml of the mixture (closed circles) was passed through a PD-10 column and the fractions collected read using a β-counter. Free glucosamine (open triangles), passed through a PD-10 column and the fractions collected read using a β-counter. Similar results were obtained for dendrimer gen 2.5-glucosamine.

FIG. 4:
FT-IR spectra of dendrimers gen 3.5 (a),
glucosamine (b),
and dendrimers gen 3.5-glucosamine (c).

FIG. 5:
Schematic representation of dendrimers gen 3.5-glucosamine.

Figure 6:
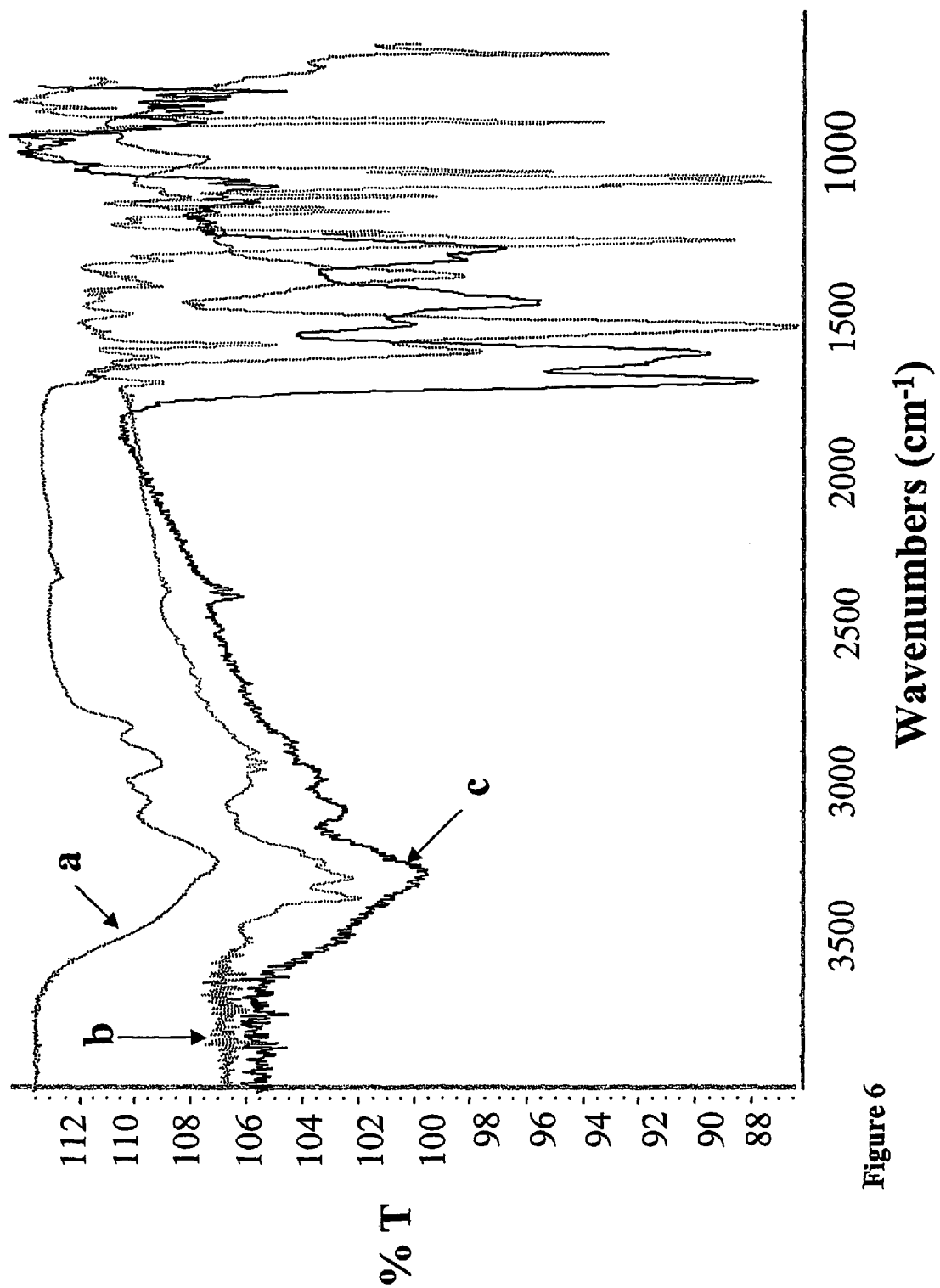

FIG. 6:
FT-IR spectra of dendrimers gen 3.5 (a),
glucosamine 6-sulfate (b),
and dendrimer gen 3.5-glucosamine 6-sulfate (c).

Figure 7I:
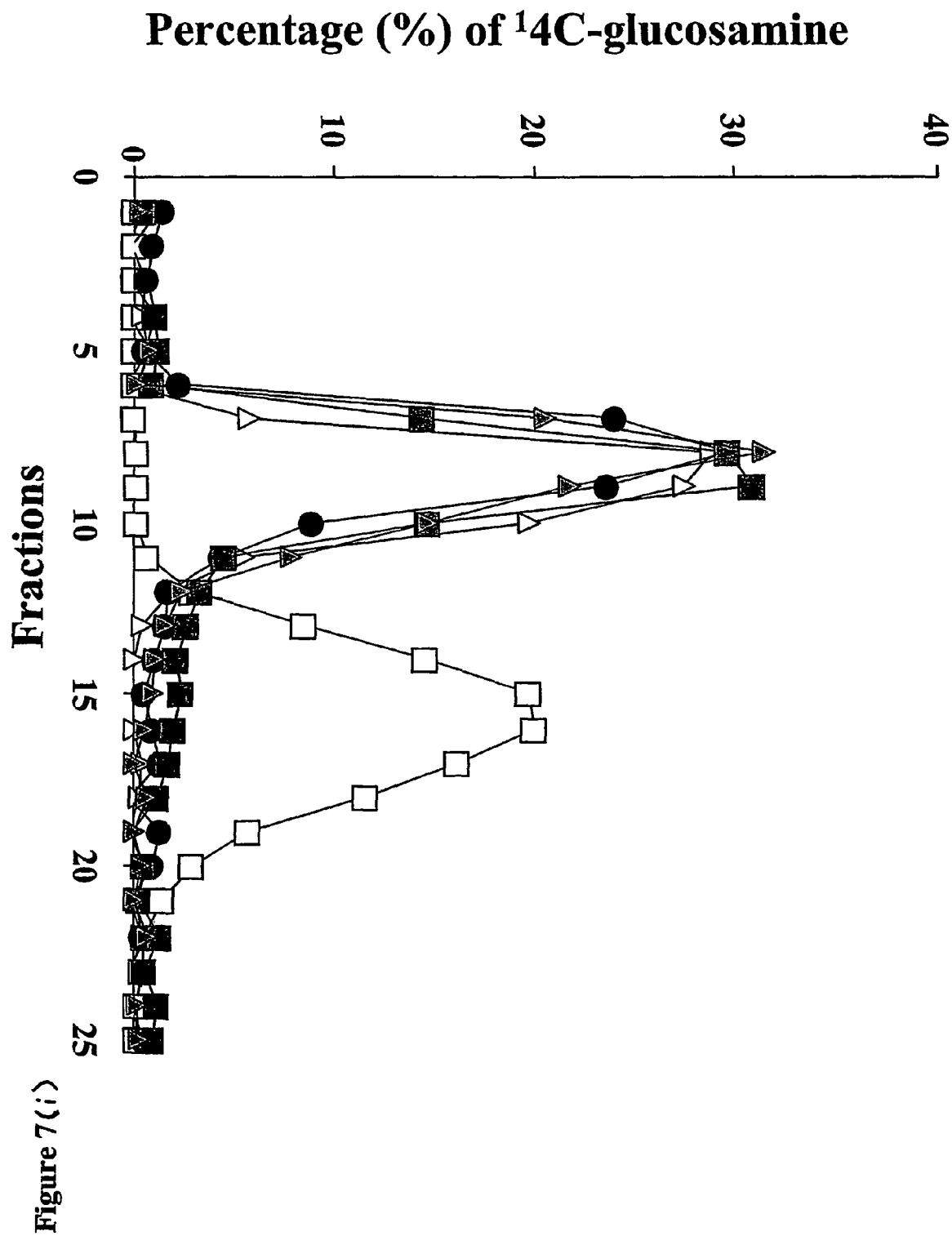
Figure 7:
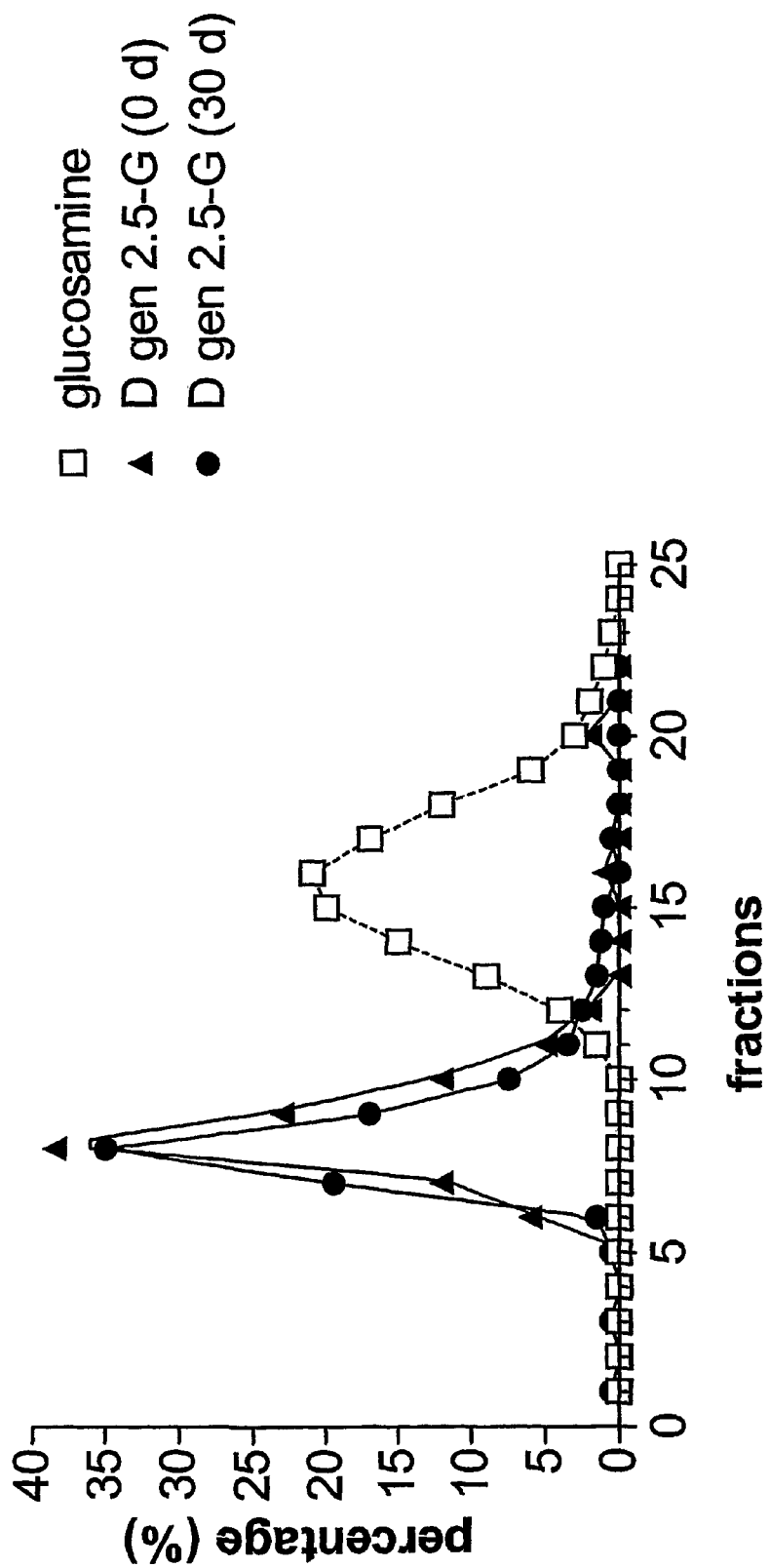

FIG. 7(i):
Stability of the dendrimers gen 3.5-glucosamine during storage.
Dendrimers gen 3.5-glucosamine was stored as an aqueous solution. An aliquot of the aqueous solution was taken at day 0 (open triangles), day 7 (filled circles), day 15 (filled squares), day 90 (filled triangles) passed through a PD-10 column and the fractions collected read using a β-counter. Free giucosamine (open squares) passed through the PD-10 column and the fractions collected were read using a β-counter.

FIG. 7(ii):
Stability of the dendrimers gen 2.5-glucosamine during storage.
Dendrimers gen 2.5-glucosamine was stored as an aqueous solution. An aliquot of the aqueous solution was taken at day 0 (filled triangles) and day 30 (filled circles), passed through a PD-10 column and the fractions collected read using a β-counter. Free glucosamine (open squares) passed through the PD-10 column and the fractions collected were read using a β-counter.

FIG. 8(i):
No release of MIP-1β above that seen in the control wells occurred with PBMN cells and dendrimer gen 3.5, dendrimer gen 3.5-glucosamine, or dendrimer gen 3.5-glucosamine 6-sulfate at 50 μg/ml.

FIG. 8(ii) and 8(iii):
No release of MIP-1β above that seen in the control wells occurred with MDMs and dendrimer gen 3.5, dendrimer gen 3.5-glucosamine, or dendrimer gen 3.5-glucosamine 6-sulfate at 50 μg/ml.

Figure 9:
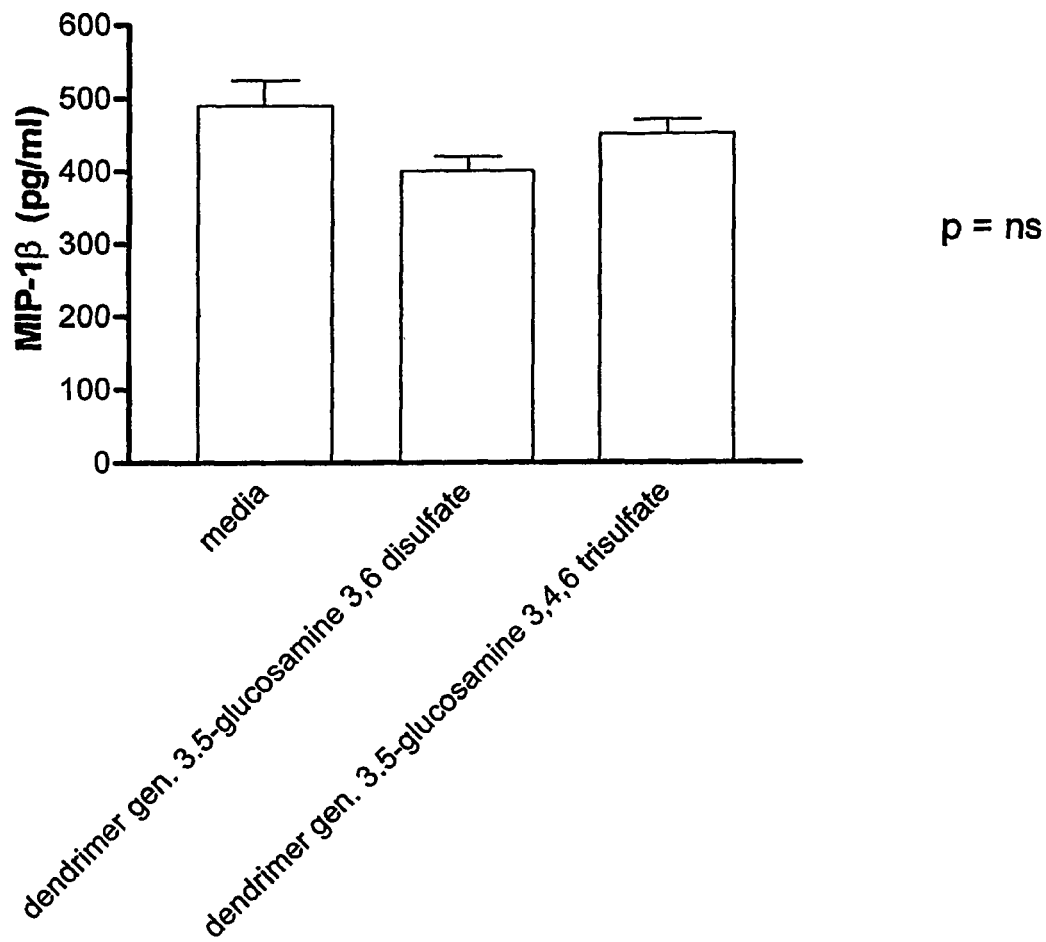

FIG. 9:
No release of MIP-1β above that seen in the control wells occurred with MDMs and dendrimer gen 3.5-glucosamine 3,6-disulfate, or dendrimer gen 3.5-glucosamine 3,4,6-trisulfate at 50 μg/ml.

FIG. 10(i) and (ii):
No release of MIP-1β above that seen in the control wells occurred with peritoneal macrophages after 36 h of culture with dendrimer gen 3.5, dendrimer gen 3.5-glucosamine, or dendrimer gen 3.5-glucosamine 6-sulfate with each molecule at 25 µg/ml:

FIG. 10(iii):

No release of MIP-1β above that seen in the control wells occurred with peritoneal macrophages after 72 h of culture with dendrimer gen 3.5, dendrimer gen 3.5-glucosamine, or dendrimer gen 3.5-glucosamine 6-sulfate with each molecule at 25 µg/ml.

FIG. 11(i) and (ii):

No release of MIP-1β above that seen in the control wells occurred with peritoneal macrophages after 36 h of culture with dendrimer gen 3.5, dendrimer gen 3.5-glucosamine, or dendrimer gen 3.5-glucosamine 6-sulfate with each molecule at 50 µg/ml.

FIG. 12(i) and (ii):

No release of MIP-1β above that seen in the control wells occurred with peritoneal macrophages after 36 h of culture with dendrimer gen 3.5-glucosamine 3,6-disulfate, or dendrimer gen 3.5-glucosamine 3,4,6-trisulfate with each molecule at 50 µg/ml:

FIG. 13(i) and (ii):

No release of MIP-1β above that seen in the control wells occurred with peritoneal macrophages after 36 h of culture with dendrimer gen 3.5-glucosamine 3,6-disulfate, or dendrimer gen 3.5-glucosamine 3,4,6-trisulfate with each molecule at 100 µg/ml.

FIG. 13(iii) and (iv):

No release of MIP-1β above that seen in the control wells occurred with peritoneal macrophages after 36 h of culture with dendrimer gen 3.5-glucosamine 3,6-disulfate, or dendrimer gen 3.5-glucosamine 3,4,6-trisulfate with each molecule at 200 µg/ml.

FIG. 14(i):

The dendrimer gen 3.5-glucosamine was cultured with MDMs for 72 h up to a concentration of 150 µg/ml. No reduction in cell count or viability (as determined by Trypan blue and MTT assay) was found.

FIG. 14(ii):

The dendrimer gen 3.5-glucosamine was cultured with HUVECs for 72 h up to a concentration of 100 µg/ml. No reduction in cell count or viability (as determined by Trypan blue and MTT assay) was found.

FIG. 15:

Single donor PBMN cells were isolated and cultured with LPS at 5 ng/ml. Cell free culture supernatants were harvested at regular intervals for up to 21 h and assayed for MIP-1β.

FIG. 16(i)

Single donor PBMN cells were cultured with dendrimer gen 3.5-glucosamine (100 µg/ml) for 30 min and LPS was then added at 5 ng/ml. Cell free culture supernatants were harvested 21 h later and assayed for MIP-1β. A significant reduction in MIP-1β release was seen.

FIG. 16(ii)

Single donor PBMN cells were cultured with dendrimer gen 3.5-glucosamine (100 tug/ml) for 1 h and LPS was then added at 5 ng/ml. Cell free culture supernatants were harvested 21 h later and assayed for MIP-1β. A significant reduction in MIP-1β release was seen.

FIG. 16(ii):

Single donor PBMN cells were cultured with dendrimer gen 3.5-glucosamine (100 µg/ml) for 24 hours and LPS was then added at 5 ng/ml. Cell free culture supernatants were harvested 21 h later and assayed for MIP-1β. A significant reduction in MIP-1β release was seen.

FIG. 16(iv):

Single donor PBMN cells were cultured with dendrimer gen 3.5-glucosamine (100 µg/ml) for periods of 30 minutes or 1 hour or 3 hours or 6 hours or 24 hours and LPS was then added at 5 ng/ml. Cell free culture supernatants were harvested 21 h later and assayed for MIP-1β.

A significant reduction in MIP-1β release was seen at all of the time points studied.

FIG. 17:

Single donor PBMN cells were isolated and cultured with LPS at 5 ng/ml. Cell free culture supernatants were harvested at regular intervals for up to 21 h and assayed for TNF-α.

FIGS. 18(i) to (vi):

Single donor PBMN cells were cultured with dendrimer gen 3.5-glucosamine (100 µg/ml) for 30 min and LPS was then added at 5 ng/ml. Cell free culture supernatants were harvested 21 h later and assayed for MIP-1α as shown in FIG. 18(i), MIP-1β as shown in FIG. 18(ii), IL-8 as shown in FIG. 18(iii), TNF-α as shown in FIG. 18(iv), IL-1β as shown in FIG. 18(v), and IL6 as shown in FIG. 18(vi). For all of the chemolines and pro-inflammatory cytokines studied, a significant reduction in their release was seen when dendrimer gen 3.5-glucosamine was present.

FIGS. 19(i) to (vi):

Single donor PBMN cells were cultured with dendrimer gen 3.5-glucosamine (200 µg/ml) and LPS was then added at 5 ng/ml. Cell free culture supernatants were harvested 21 h later and assayed for MIP-1α as shown in FIG. 19(i), MIP-1β as shown in FIG. 19(ii), IL-8 as shown in FIG. 19(iii), TNF-α as shown in FIG. 19(iv), IL-1β as shown in FIG. 19(v), and IL-6 as shown in FIG. 19(vi). For all of the chemokines and pro-inflammatory cytokines studied, a significant reduction in their release was seen when dendrimer gen 3.5-glucosamine was present.

FIGS. 20(i) and (ii):

Single donor PBMN cells were cultured with dendrimer gen 3.5-glucosamine (200 µg/ml) for 1 hour and LPS was then added at 5 ng/ml. Cell free culture supernatants were harvested h later and assayed for MIP-1β as shown in FIG. 20(i) and TNF-α as shown in FIG. 20(ii). For all of the chemokines and pro-inflammatory cytokines studied, a significant reduction in their release was seen when dendrimer gen 3.5-glucosamine was present.

FIG. 21:

Single donor PBMN cells were isolated and resuspended in RPMI, L-glutamine, penicillin, streptomycin and 10% human serum at a density of $1 \times 10^6$ cells/ml. The cells were then plated (1 ml) in 12 well tissue culture plates and cultured for 15 ml at 37° C. in 5% $CO_2$. LPS was then added at 5 ng/ml and the cells were cultured for 30 min, or 1 hour, or 2 hours, or 3 hours, or 4 hours at 37° C. in 5% $CO_2$ before adding dendrimer gen 3.5-glucosamine at 100 µg/ml. Cell free culture supernatants were harvested 21 h after the addition of the LPS and assayed for MIP-1α as shown in FIG. 21(i), MIP-1β as shown in FIG. 21(ii), IL-8 as shown in FIG. 21(iii), TNF-α as shown in FIG. 21(iv), IL-1 as shown in FIG. 21(v), and IL-6 as shown in FIG. 21(vi). For all of the chemokines and pro-inflammatory cytokines studied, a significant reduction in their release was seen when dendrimer gen 3.5-glucosamine was present.

FIG. 22:

Single donor PBMN cells were cultured with dendrimer gen 3.5-glucosamine in which the loading of glucosamine was 3% (rather than the 7% used in all other experiments) at a concentration of 150 µg/ml or 300 µg/ml. The cells were cultured for 30 min at 37° C. in 5% $CO_2$ and LPS was then added at 5 ng/ml. Cell free culture supernatants were harvested 22 h later and assayed for MIP-1β as shown in FIG.

22(*i*), or for TNF-α as shown in FIG. 22(*ii*). For all of the chemolines and pro-inflammatory cytokines studied, a significant reduction in their release was seen when dendrimer gen 3.5-glucosamine was present.

FIG. 23:

Single donor PBMN cells were isolated from 3 individuals and mixed together for 72 h. Dendrimer gen 3.5-glucosamine was then added at 50-100 µg/ml. Cell free culture supernatants were harvested 1 day, 3 days and 4 days later and assayed for MIP-1β and TNF-α. A significant reduction in MIP-1β and TNF-α release into the culture supernatant was seen at all 3 time points assayed as shown in FIGS. 23(*i*) and 23 (*ii*).

Single donor PBMN cells were isolated from 2 individuals and then cultured separately for 24 h. They were then mixed together for 72 h. The dendrimer gen 3.5-glucosamine was then added at 50 µg/ml. Cell free culture supernatants were harvested 1 day, 3 days and 4 days later and assayed for MIP-1β. A significant reduction in MIP-1β release into the culture supernatant was seen at all 3 time points assayed as shown in FIG. 23(*iii*).

FIG. 24:

Single donor PBMN cells were isolated from 2 individuals and mixed together. Dendrimer gen 3.5-glucosamine was then added at 100 µg/ml followed immediately by LPS (10 ng/ml).

Cell free culture supernatants were harvested at regular intervals for up to 50 h. A significant reduction in MIP-1β release into the culture supernatant was seen from 24 h onwards as shown in FIG. 24(*i*).

Single donor PBMN cells were isolated from 2 individuals and mixed together. Dendrimer gen 3.5-glucosamine was added at 100 µg/ml. Twenty-four hours later, LPS was added at a concentration of 5 ng/ml. Cell free culture supernatants were harvested at regular intervals or up to 100 h. A significant reduction in MIP-1β release into the culture supernatant was seen from 24 h onwards as shown in FIG. 24(*ii*).

FIG. 25:

The dendrimer gen 3.5-glucosamine 6-sulfate did not affect the cell viability or the growth characteristics of PBMN cells when present at a concentration of 50 µg/ml (FIG. 25(*i*)) or 150 µg/ml (FIG. 25(*ii*)) in cultures maintained for up to 5 days. Cell viability was determined by Trypan blue exclusion and an MTT assay.

FIG. 26:

The dendrimer gen 3.5-glucosamine 6-sulfate did not affect cell viability or growth characteristics of MDMs when present up to a concentration of 150 µg/ml in cultures maintained for up to 5 days. Cell viability was determined by Trypan blue exclusion and an MTT assay.

FIG. 27(*i*) and (*ii*) & (*iii*):

The dendrimer gen 3.5-glucosamine 6-sulfate construct was also not toxic to HUVECs when added to cultures of these cells up to a concentration of 100 µg/ml for up to 72 hours.

FIG. 28:

PBMN cells were cultured with dendrimer gen 3.5-glucosamine 6-sulfate (150 µg/ml or 200 µg/ml) for 30 min and LPS (5 ng/ml) was then added. Cell free culture supernatants were harvested 24 h later for MIP-1β (FIG. 28(*i*)) and for TNF-α (FIG. 28(*ii*)). A significant reduction in both the chemokine and the pro-inflammatory cytokine was seen when dendrimer gen 3.5-glucosamine 6-sulfate was present at 150 µg/ml and at 200 µg/ml.

FIG. 29:

PBMN cells were isolated from 4 individuals and then mixed together for 24 h. MDMs were separated by adherence to plastic and then cultured with dendrimer gen 3.5-glucosamine or dendrimer gen 3.5-glucosamine 6-sulfate at 125 µg/ml. Cell free culture supernatants were harvested 36 h later and assayed for MIP-1β. A significant reduction in MIP-1β was seen.

FIGS. 30-32:

Endothelial microtubule formation by HUVECs on Matrigel (×40 magnification). A visual analogue scale was used to determine the extent of tube formation and scored on a scale from 0 (all cells remain single) to 4 (all cells involved in tubular structures) as previously described (Bauer J, Margolis M, Schreiner C, Edgell C-J, Azizkhan J, Lazarowski E, & Juliano R L. (1992) In vitro model of angiogenesis using a human endothelium derived permanent cell line: contributions of induced gene expression, G-proteins and integrins. J. Cellular Physiology 153: 437-449; Liaw, L & Schwartz S M. (1993) Microtubule disruption stimulates DNA synthesis in bovine endothelial cells and potentiates cellular response to basic fibroblast growth factor. American Journal of Pathology 143: 937-948).

FIG. 30: Control well,

FIG. 31: Dendrimer gen 3.5-glucosamine 6-sulfate at 12.5 µg/ml,

FIG. 32: Dendrimer gen 3.5-glucosamine 6-sulfate at 50 µg/ml.

FIG. 33:

Dendrimer gen 3.5-glucosamine 6-sulfate (O) reduced the rate of new vessel formation in an in vitro angiogenesis assay when compared to media alone (Δ). The results shown are for dendrimer gen 3.5-glucosamine 6-sulfate at a final concentration of 50 µg/ml. The degree of new vessel formation was quantified blind twice a week using a visual analog scale in which 0=no growth, 1=minimal new vessel formation, 2=significant new vessel formation, and 3=dense new vessel formation. An angiogenesis score was derived from each count by dividing the total score (i.e. the sum of all the wells) by the maximum possible score and then expressing the result as a percentage. A significant reduction in new vessel formation was seen by day 18 ($p<0.05$). This graph is representative of 2 experiments performed in quadruplicate. New vessel formation was quantified blind by 3 different observers twice a week with a within-observer and between-observer variability of <10%.

FIG. 34:

Cartoon describing the pathogenesis of medical disorders in which chemokines and angiogenesis play an important role. It identifies the new targets at which dendrimer gen 3.5-glucosamine and dendrimer gen 3.5-glucosamine 6-sulfate can act either alone or in synergy to produce a clinically useful therapeutic effect.

FIG. 35:

Single donor PBMN cells were cultured with dendrimer gen 3.5-glucosamine (200 µg/ml) for 30 min and the superantigen toxin SEB was then added at 100 ng/ml. Cell free culture supernatants were harvested 21 h later and assayed for MIP-1β as shown in FIG. 35(*i*) and for TNF-α as shown in FIG. 35(*ii*). For the chemokine and the cytokine studied, a significant reduction in their release was seen when dendrimer gen 3.5-glucosamine was present.

FIG. 36:

Immature monocyte derived dendritic cells were prepared and plated at $1 \times 10^6$/well.

Dendrimer gen 3.5-glucosamine (200 µg/ml) was added for 1 hour followed by LPS (5 ng/ml). The cells were cultured for 21 hours and then harvested for FACS analysis. As shown in FIG. 36, dendrimer gen. 3.5-glucosamine significantly reduced LPS induced upregulation of CD25 on the dendritic cells.

FIG. 37:

Gamma irradiated purified monocyte derived dendritic cells were incubated in triplicate in aliquots ranging from 64,000 to 32 dendritic cells per well with dendrimer gen. 3.5 glucosamine (200 μg/ml) for 1 hour at 37° C. Allogeneic peripheral blood lymphocytes (100,000/well) were then added. The plates were incubated for 5 days. In addition, prior to adding the peripheral blood lymphocytes, the plates (with and without dendrimer gen. 3.5 glucosamine) were incubated with LPS at a concentration of 5 ng/ml for 21 hours. The cells were then washed three times. Dendrimer gen. 3.5 glucosamine was then added back at a concentration of 200 μg/ml. Peripheral blood lymphocytes were added at 100,000 cells/well and the plates incubated for 5 days. To these cultures, [$^3$H]-Thymidine (1 μCi/well) was then added for a further 18 hours and the cells cultured. After this time, the cells were harvested and proliferation measured using a liquid scintillation counter. FIG. 37 shows the results from three experiments. In each case, the proliferation caused by the mixed lymphocyte reaction as well as the proliferation caused by LPS at 5 ng/ml was significantly inhibited.

FIG. 38:

Gamma irradiated purified monocyte derived dendritic cells were incubated in triplicate in aliquots ranging from 64,000 to 32 dendritic cells per well. Allogeneic peripheral blood lymphocytes (100,000/well) were then added and the plates incubated for 5 days. In addition, prior to adding the peripheral blood lymphocytes, the plates (with and without dendrimer gen. 3.5 glucosamine) were incubated with lipopolysaccharide at a concentration of 20 ng/ml for 21 hours. The cells were then washed three times. Dendrimer gen. 3.5 glucosamine was then added back at a concentration of 200 μg/ml. Peripheral blood lymphocytes were added at 100,000 cells/well and the plates incubated for 5 days. To these cultures, [$^3$H]-Thymidine (1 μCi/well) was then added for a further 18 hours and the cells cultured. After this time, the cells were harvested and proliferation measured. FIG. 38 shows the results from two experiments. In each case, the proliferation caused by the mixed lymphocyte reaction as well as the proliferation caused by LPS at 20 ng/ml was significantly inhibited.

FIG. 39:

Gamma irradiated isolated, purified peritoneal dendritic cells were incubated in triplicate in aliquots ranging from 64,000 to 32 dendritic cells/well with dendrimer gen. 3.5 glucosamine (200 μg/ml) for 1 hour. Allogeneic peripheral blood lymphocytes (100,000/well) were added and the plates incubated for 5 days. In addition, prior to adding the peripheral blood lymphocytes, the plates (with and without dendrimer gen. 3.5 glucosamine) were incubated with lipopolysaccharide at a concentration of 5 ng/ml for 21 hours. The cells were then washed three times. Dendrimer gen. 3.5 glucosamine was then added back at a concentration of 200 μg/ml. Peripheral blood lymphocytes were added at 100,000 cells/well and the plates incubated for 5 days. To these cultures, [$^3$H]-Thymidine (1 μCi/well) was then added for a further 18 hours and the cells cultured. After this time, the cells were harvested and proliferation measured. FIG. 39 shows the results from three experiments. In each case, the proliferation caused by the mixed lymphocyte reaction as well as the proliferation caused by LPS at 5 ng/ml was significantly inhibited.

FIG. 40:

Gamma irradiated isolated, purified peritoneal derived dendritic cells were incubated in triplicate in aliquots ranging from 64,000 to 32 dendritic cells/well with dendrimer gen. 3.5 glucosamine (200 μg/ml) for 1 hour at 37° C. Allogeneic peripheral blood lymphocytes 100,000/well) were then added. The plates were incubated for 5 days at 37° C. In addition, prior to adding the peripheral blood lymphocytes, the plates (with and without dendrimer gen. 3.5 glucosamine) were incubated with lipopolysaccharide at a concentration of 20 ng/ml for 21 hours. The cells were then washed three times. Dendrimer gen. 3.5 lucosamine was then added back at a concentration of 200 μg/ml. Peripheral blood lymphocytes were added at 100,000 cells/well and the plates incubated for 5 days. To these cultures, [$^3$H]-Thymidine (1 μCi/well) was then added for a further 18 hours and the cells cultured. After this time, the cells were harvested and proliferation measured. FIG. 40 shows the results from two experiments. In each case, the proliferation caused by the mixed lymphocyte reaction as well as the proliferation caused by LPS at 20 ng/ml was significantly inhibited.

FIG. 41:

Gamma irradiated purified monocyte derived dendritic cells or gamma irradiated isolated, purified peritoneal dendritic cells were incubated in aliquots ranging from 32,000 to 2,000 dendritic cells/well with dendrimer gen. 3.5 glucosamine (200 μg/ml) for 1 hour at 37° C. and 5% $CO_2$. Lipopolysaccharide (20 ng/ml) was then added for 21 hours. The cells were then washed three times with media and the dendrimer gen. 3.5 glucosamine (200 μg/ml) replaced. Allogeneic lymphocytes (100,000/well) were then added and this was defined as day 0. The plates were incubated at 37° C. and 5% $CO_2$ and cell free culture supernatants were collected at day 3 and day 5 for the measurement of interleukin-2 and γ-interferon. FIG. 41(*i*) shows that dendrimer gen. 3.5 glucosamine caused a significant reduction in the release of interleukin-2 and interferon from gamma irradiated purified monocyte derived dendritic cells. FIG. 41(*ii*) shows that dendrimer gen. 3.5 glucosamine caused a significant reduction in the release of interleukin-2 and γ-interferon from gamma irradiated isolated, purified peritoneal dendritic cells.

FIG. 42:

Single donor PBMN cells were suspended at 1×10$^6$ cells/ml and dendrimer gen 3.5-glucosamine added at 200 μg/ml. The cells were cultured for 30 min and the superantigen SEB added at 100 ng/ml. Cell free culture supernatants were harvested 21 h later and assayed for MIP-1β as shown in FIG. 42(*i*) and for TNF-α as shown in FIG. 42(*ii*). For both the chemokine and the cytokine a significant reduction in their release was seen when dendrimer gen 3.5-glucosamine was present.

TABLE 1

This table shows the reproducibility of the synthesis of the dendrimer gen 3.5-glucosamine conjugate with a 7% loading of glucosamine that was used for most of the experiments described. Results are also shown for the dendrimer gen 3.5-glucosamine conjugate with a 3% loading of glucosamine that was used for Experiment B 12, FIG. 22.

| | mmol glucosamine used in reaction | % converted carboxylic groups | Unbound glucosamine content (wt %) | Yield (%) |
|---|---|---|---|---|
| 3% glucosamine loading | 0.25 | 3.18 ± 0.46 | 2.3 | 63 |
| 7% glucosamine loading | 0.5 | 7.89 ± 0.27 | 3.1 | 60 |
| 7% glucosamine loading | 0.5 | 7.24 ± 0.51 | 2.8 | 60 |

TABLE 1-continued

This table shows the reproducibility of the synthesis of the dendrimer gen 3.5-glucosamine conjugate with a 7% loading of glucosamine that was used for most of the experiments described. Results are also shown for the dendrimer gen 3.5-glucosamine conjugate with a 3% loading of glucosamine that was used for Experiment B 12, FIG. 22.

| mmol glucosamine used in reaction | % converted carboxylic groups | Unbound glucosamine content (wt %) | Yield (%) |
|---|---|---|---|

The total amount of glucosamine bound to the dendrimers was determined using a β-counter (data shown as mean±SD of 3 replicates). The unbound glucosamine content was determined using a β-counter followed by gel filtration CD-10 column) of the purified conjugate.

TABLE 2

Characterisation of the different batches of dendrimer gen 3.5-sulfated glucosamine conjugates prepared.

| | Sulphur content (% m:m S) | Yield (%) |
|---|---|---|
| 3.5-G6S (batch 1) | 1.76 | 53 |
| 3.5-G6S (batch 2) | 2.79 | 85 |
| 3.5-G3,6S (batch 1) | 5.18 | 70 |
| 3.5-G3,6S (batch 2) | 5.78 | 68 |
| 3.5-G3,4,6S (batch 1) | 7.65 | 81 |
| 3.5-G3,4,6S (batch 2) | 7.93 | 70 |

The amount of sulfated sugar bound to the dendrimer gen 3.5 was determined by sulphur analysis.

'3.5-G6S' stands for dendrimers gen 3.5-glucosamine 6-sulfate,

'3.5-G3,6S' stands for dendrimer gen 3.5-glucosamine 3,6-disulfate,

'3.5-G3,4,6S' stands for dendrimer gen 3.5-glucosamine 3,4,6-trisulfate.

TABLE 3

Toxicity of dendrimers gen 3.5-glucosamine and dendrimers gen 3.5-glucosamine 6-sulfate conjugates in several human cell lines and in a murine melanoma cell line.

| | Sup-T1 | C8166 | U937 | U87-CD4-CCR5 | B16F10 |
|---|---|---|---|---|---|
| DG 3.5-G | 1825 ± 227 | 3000 ± 100 | 2837 ± 107 | 2077 ± 237 | 2894 ± 96 |
| DG 3.5-G6S | 307 ± 29 | 279 ± 7 | 271 ± 19 | 256 ± 21 | 246 ± 17 |
| Dendrimers gen 3.5 | >5000 | >5000 | >5000 | >5000 | >5000 |
| G | >1000 | >1000 | >1000 | >1000 | >1000 |
| G6S | >1000 | >1000 | >1000 | >1000 | >1000 |
| Dextran | >5000 | >5000 | >5000 | >5000 | >5000 |
| Poly(L-lysine) | 25 ± 1 | 28 ± 1 | 28 ± 1 | 28 ± 0 | 28 ± 1 |

The toxicity of the conjugates and reference controls was analysed against the human cell lines Sup-T1, C8166, U937, and U87-CD4-CCR5, and the murine melanoma cell line (B16F10).
The $IC_{50}$ values (μg/ml) ± SEM (n = 16) were determined using the MTT assay.
'DG 3.5-G' stands for dendrimer gen 3.5-glucosamine.
'DG 3.5-G6S' stands for dendrimer gen3.5-glucosamine 6-sulfate.
'G' stands for glucosamine.
'G6S' stands for glucosamine 6-sulfate.

TABLE 4a

Interaction of chemokines and cytokines with dendrimers gen 3.5-glucosamine conjugates:

| | Standard concentration (pg/ml) | Standard Reading (pg/ml) | Standard + Dendrimer gen 3.5-glucosamine (pg/ml) |
|---|---|---|---|
| MIP-1α | 125 | 99.86 | 103.94 |

TABLE 4a-continued

Interaction of chemokines and cytokines with dendrimers gen 3.5-glucosamine conjugates:

| | Standard concentration (pg/ml) | Standard Reading (pg/ml) | Standard + Dendrimer gen 3.5-glucosamine (pg/ml) |
|---|---|---|---|
| MIP-1β | 125 | 112.17 | 100.36 |
| TNF-α | 125 | 123.44 | 63.77 |
| IL-1β | 31.2 | 28.23 | 23.80 |
| IL-6 | 25 | 26.17 | 21.69 |
| IL-8 | 250 | 298.30 | 280.15 |

There was no interference of the dendrimer gen 3.5 glucosamine with the MIP-1α, MIP-1β, IL-1β, IL-6 or IL-8 assays.

TABLE 4b

Interaction of TNF-α with dendrimers gen 3.5-glucosamine conjugates:
In the case of TNF-α assay, a significant degree of interference by dendrimer gen 3.5 glucosamine was seen as illustrated below.

| TNF-α standard (pg/ml) | TNF-α standard (EIA optical density) | TNF-α standard + dendrimer gen 3.5 glucosamine (EIA optical density) |
|---|---|---|
| 15.60 | 0.062 | 0.044 |
| 31.25 | 0.096 | 0.058 |
| 62.50 | 0.169 | 0.090 |
| 125.00 | 0.273 | 0.161 |
| 250.00 | 0.514 | 0.326 |
| 500.00 | 0.935 | 0.596 |

A correction factor has therefore been applied to all of the TNF-α data shown as it relates to dendrimer gen 3.5 glucosamine.

TABLE 5

Anticoagulant activity of dendrimer gen 3.5-glucosamine and dendrimer gen 3.5-sulfated glucosamine conjugates: The compounds were dissolved in phosphate-buffered saline solution (PBS) and tested, or dissolved in RPMI + 15% FCS and tested, or mixed 50:50 with human plasma/veronal buffer and tested. The anti-Xa activity was expressed as units of heparin/ml (HEP (Xa) (V/ml)).

|  | dissolved in | Conc (µg/ml) | PT (sec) | APTT (sec) | TT (sec) | Fibrinogen (g/L) | Anti-Xa (V/ml) |
|---|---|---|---|---|---|---|---|
| Control | PBS |  | 16.0 | 40 | 13.5 | 1.30 | 0 |
|  | RPMI/FCS |  | 16.7 | 40 | 13.8 | 1.30 | 0 |
|  | Plasma/veronal buffer |  | 16.5 | 41 | 13.7 | 1.30 | 0 |
| D gen. 3.5-G | PBS | 200 | 15.8 | 42 | 13.8 | 1.29 | 0 |
|  | RPMI/FCS | 200 | 15.5 | 41 | 13.5 | 1.30 | 0 |
|  | Plasma/veronal buffer | 300 | 15.6 | 42 | 13.7 | 1.31 | 0 |
| D gen. 3.5-G6S | PBS | 50 | 15.8 | 43 | 14.0 | 1.33 | 0 |
|  | RPMI/FCS | 50 | 16.0 | 42 | 13.8 | 1.30 | 0 |
| D gen. 3.5-G3,6S | PBS | 200 | 15.8 | 43 | 14.2 | 1.36 | 0 |

TABLE 6

Endothelial microtubule formation with dendrimer gen, 3.5 glucosamine 6-sulfate and 3,6 disulfate:

| Compound | Tube formation score (n = 4) |
|---|---|
| control | 4 |
| dendrimers gen 3.5 (100 µg/ml) | 4 |
| glucosamine (100 µg/ml) | 4 |
| glucosamine 6-sulfate (100 µg/ml) | 4 |
| glucosamine 3,6-disulfate (100 µg/ml) | 4 |
| dendrimer gen 3.5-glucosamine 6-sulfate | |
| 0 µg/ml | 4 |
| 0.25 µg/ml | 4 |
| 0.5 µg/ml | 4 |
| 0.8 µg/ml | 3 |
| 1.6 µg/ml | 3 |
| 3.125 µg/ml | 3 |
| 6.25 µg/ml | 3 |
| 12 µg/ml | 2 |
| 25 µg/ml | 2 |
| 50 µg/ml | 1 |
| 100 µg/ml | 0 |
| dendrimer gen 3.5-glucosamine 3,6-disulfate | |
| 0 µg/ml | 4 |
| 6.25 µg/ml | 4 |
| 12 µg/ml | 4 |
| 25 µg/ml | 4 |
| 50 µg/ml | 3 |
| 100 µg/ml | 2 |

The invention claimed is:

1. A pharmaceutical formulation comprising a 3.5 generation glycodendrimer of an anion carboxylic terminated poly(amidoamine) core and monosaccharide linked such that a carboxy group on the core forms an amide bond with a nitrogen on the monosaccharide, said glycodendrimer selected from the group consisting of:
   poly(amidoamine)-glucosamine,
   poly(amidoamine)-glucosamine sulfate; and
   a combination thereof
   wherein the amount of glucosamine monosaccharide linked to the dendrimer core expressed as a percentage of converted carboxylic acid groups is in the range 1.5% to 10.1% and wherein the amount of glucosamine sulfate monosacharide linked to the dendrimer core expressed as a percentage of converted carboxylic acid groups is 6% or 7%.

2. A pharmaceutical formulation according to claim 1, wherein the glycodendrimer is present at a concentration in the range 100-200 µg/mL.

3. A pharmaceutical formulation according to claim 1, wherein the glucosamine sulfate is glucosamine-6-sulfate.

* * * * *